US009259198B2

(12) United States Patent
Ohta et al.

(10) Patent No.: US 9,259,198 B2
(45) Date of Patent: Feb. 16, 2016

(54) RADIOLOGICAL IMAGING DEVICE

(75) Inventors: Yasunori Ohta, Kanagawa (JP);
Naoyuki Nishino, Kanagawa (JP);
Haruyasu Nakatsugawa, Kanagawa
(JP); Fumito Nariyuki, Kanagawa (JP);
Shinji Imai, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 543 days.

(21) Appl. No.: 13/581,211

(22) PCT Filed: Feb. 17, 2011

(86) PCT No.: PCT/JP2011/053334
§ 371 (c)(1),
(2), (4) Date: Aug. 24, 2012

(87) PCT Pub. No.: WO2011/105271
PCT Pub. Date: Sep. 1, 2011

(65) Prior Publication Data
US 2012/0318991 A1    Dec. 20, 2012

(30) Foreign Application Priority Data

Feb. 26, 2010  (JP) ................................ 2010-043219
Feb. 26, 2010  (JP) ................................ 2010-043235
Feb. 26, 2010  (JP) ................................ 2010-043512
Mar. 2, 2010   (JP) ................................ 2010-045604
Dec. 10, 2010  (JP) ................................ 2010-275654
Dec. 10, 2010  (JP) ................................ 2010-275656
Dec. 10, 2010  (JP) ................................ 2010-275659
Dec. 10, 2010  (JP) ................................ 2010-275664

(51) Int. Cl.
*A61B 6/00*  (2006.01)
*A61B 6/04*  (2006.01)
*G03B 42/04* (2006.01)

(52) U.S. Cl.
CPC ................ *A61B 6/4283* (2013.01); *A61B 6/00* (2013.01); *A61B 6/4488* (2013.01); *A61B 6/04* (2013.01); *A61B 6/4411* (2013.01); *A61B 6/4423* (2013.01); *A61B 6/56* (2013.01); *G03B 42/04* (2013.01)

(58) Field of Classification Search
CPC .............. G01T 1/20; H05G 1/14; H05G 1/10; A61B 6/00
USPC ............ 250/361 R, 370.09, 370.11; 378/107, 378/101
See application file for complete search history.

(56) References Cited

U.S. PATENT DOCUMENTS 4,835,386 A * 5/1989 Shimura et al. ............... 250/582
5,835,558 A * 11/1998 Maschke ....................... 378/198
(Continued)

FOREIGN PATENT DOCUMENTS

JP    2002-082172 A    3/2002
JP    2004-077641 A    3/2004
(Continued)

OTHER PUBLICATIONS

Rejection of the Application issued by JPO on Apr. 30, 2014 in connection with corresponding Japanese Application No. JP2010-275659.

(Continued)

*Primary Examiner* — Casey Bryant
(74) *Attorney, Agent, or Firm* — Jean C. Edwards, Esq.; Edwards Neils PLLC

(57) ABSTRACT

A radiological imaging device has a panel section which houses radiation conversion panels for converting radiation to a radiological image, and a control section which is disposed on the panel section and which controls the radiation conversion panels. The control section is thicker than the panel section, or protrudes from the panel section.

16 Claims, 69 Drawing Sheets

(56) References Cited

U.S. PATENT DOCUMENTS

| | | | |
|---|---|---|---|
| 2006/0118727 A1* | 6/2006 | Tsuchino | 250/361 R |
| 2008/0240358 A1* | 10/2008 | Utschig et al. | 378/107 |
| 2008/0245968 A1* | 10/2008 | Tredwell et al. | 250/370.09 |
| 2012/0076266 A1* | 3/2012 | Kim et al. | 378/62 |

FOREIGN PATENT DOCUMENTS

| | | |
|---|---|---|
| JP | 2008-256685 A | 10/2008 |
| JP | 2009-080103 A | 4/2009 |
| JP | 2009-139972 A | 6/2009 |
| WO | 2006/035557 A1 | 4/2006 |

OTHER PUBLICATIONS

Rejection of the Application issued by JPO on Jun. 3, 2014 in connection with corresponding Japanese Patent Application No. 2010-275654.

First Office Action issued by SIPO of China on May 22, 2014 in connection with corresponding Chinese Patent Application No. 201180011061.2.

Third Office Action issued by the State Intellectual Property Office of China on Jun. 3, 2015 in connection with Chinese Patent Application No. 201180011061.2.

Second office action issued by SIPO on Dec. 29, 2014 in connection with corresponding Chinese Patent Application No. 201180011061.2.

* cited by examiner

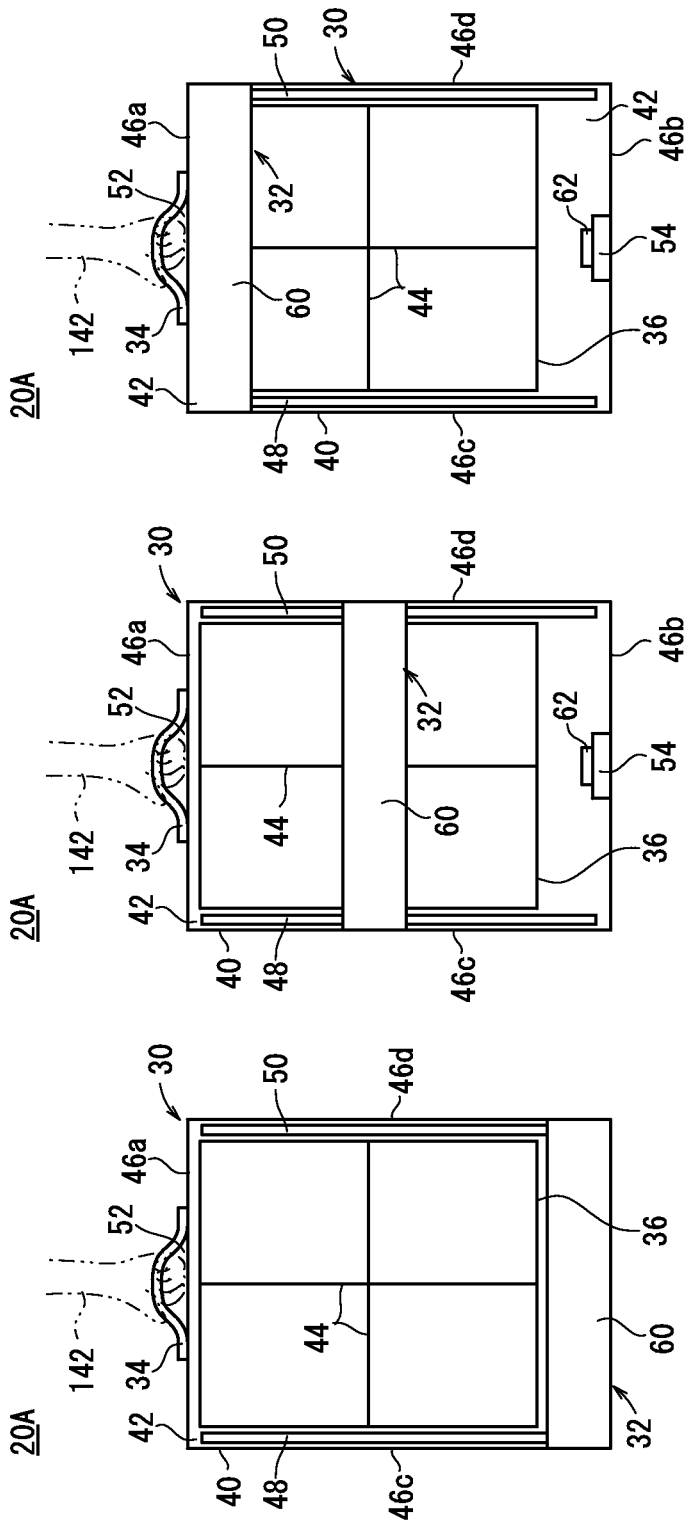

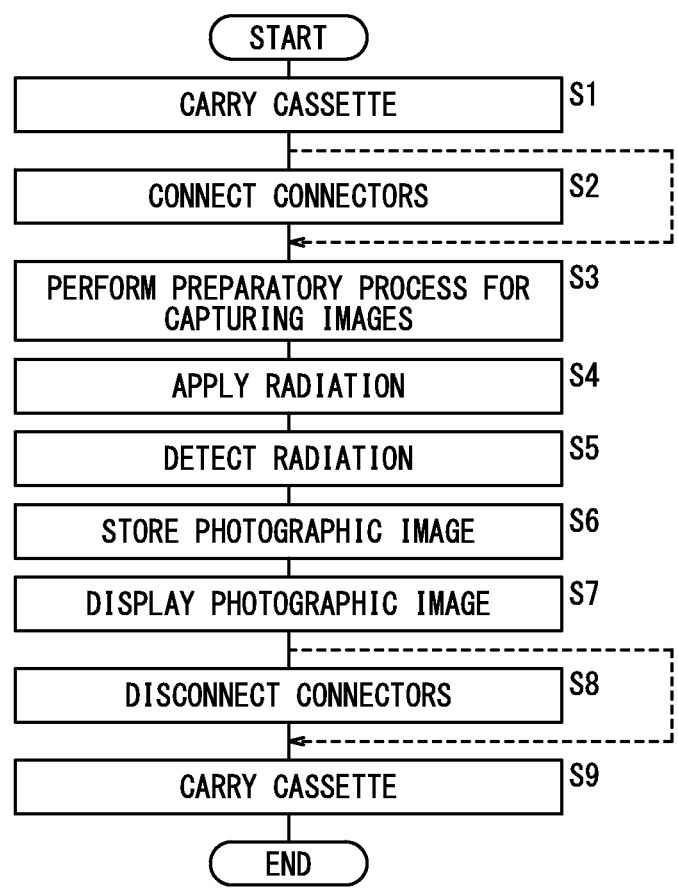

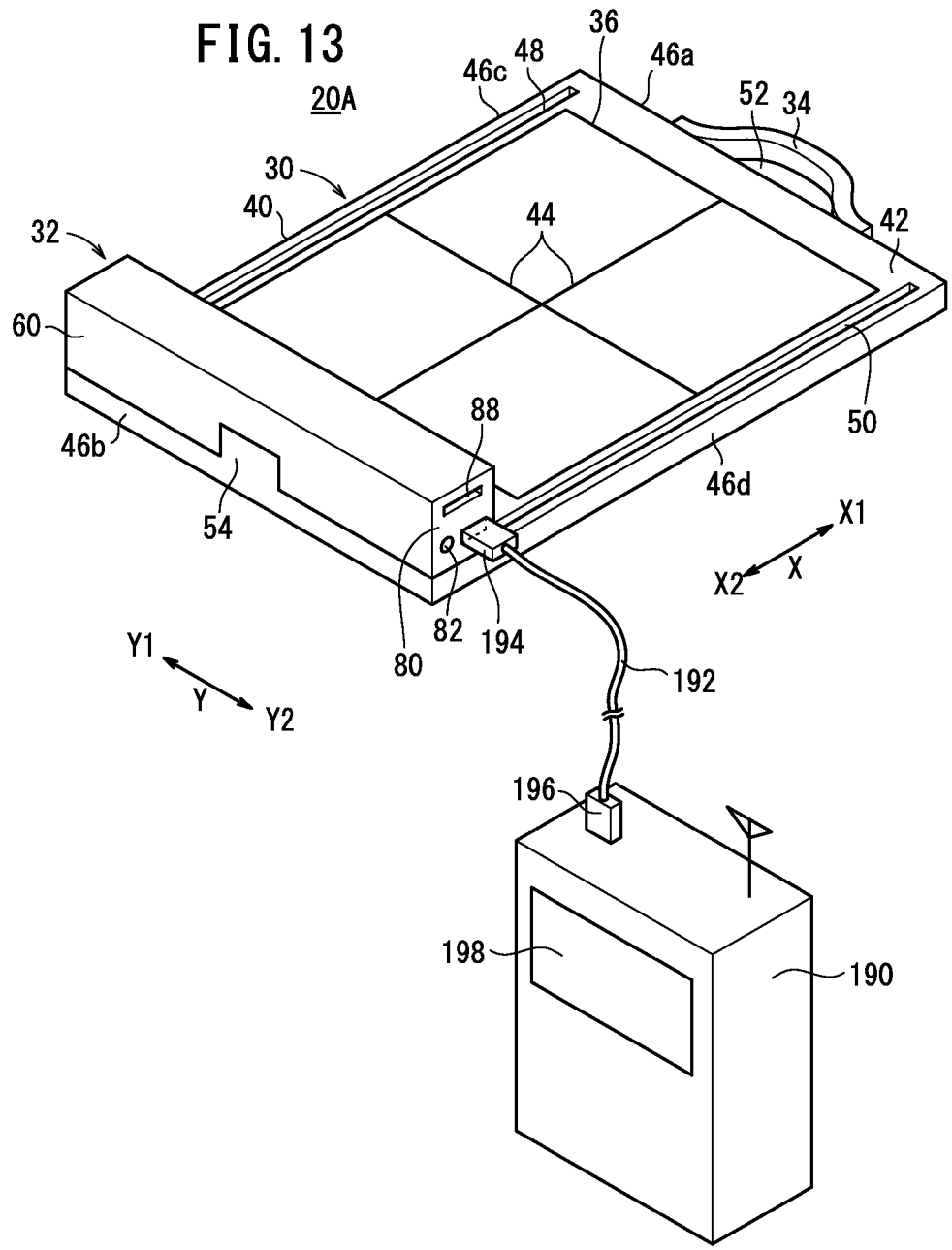

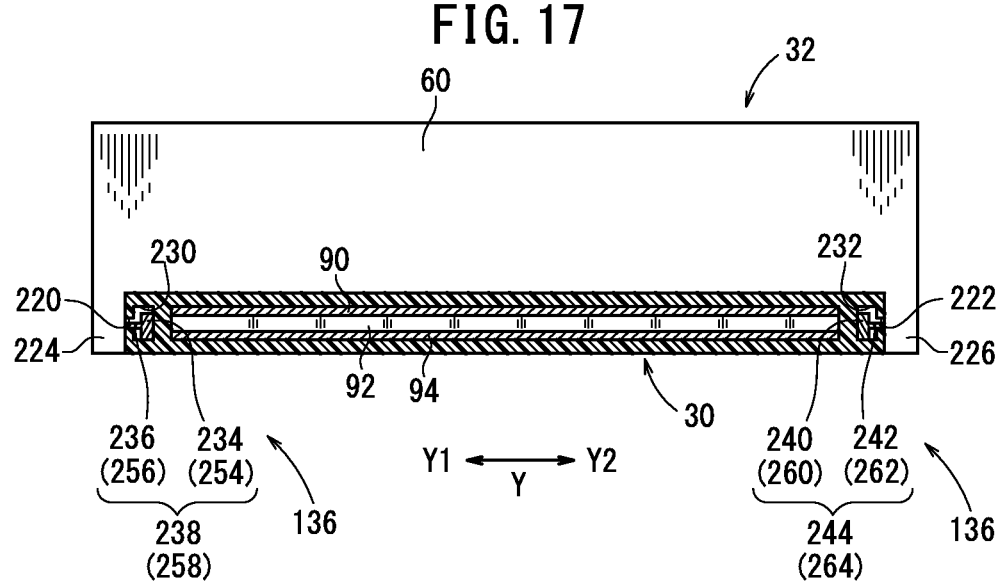

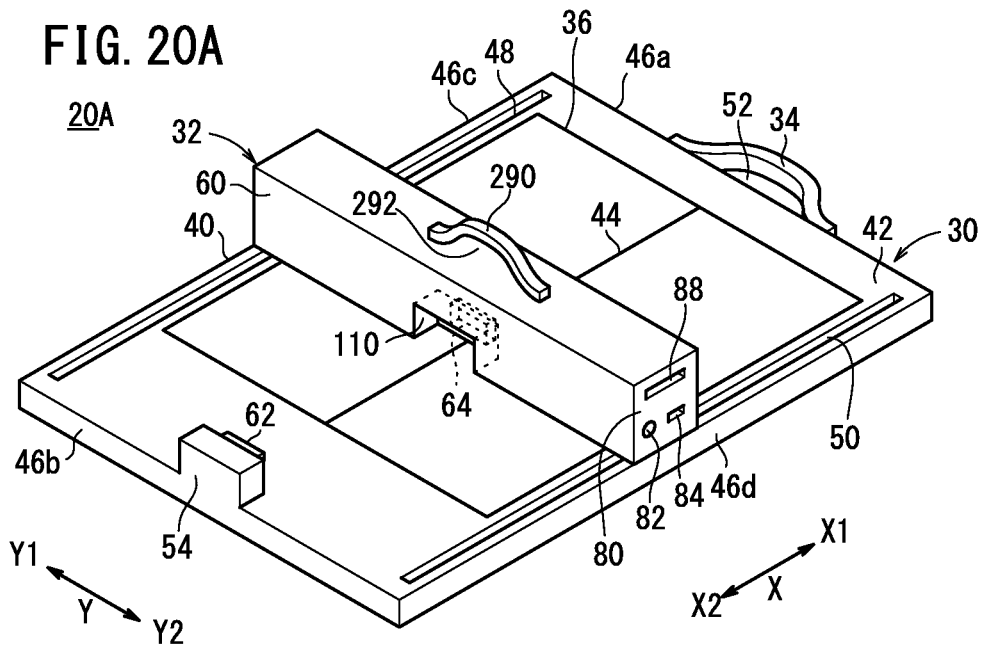
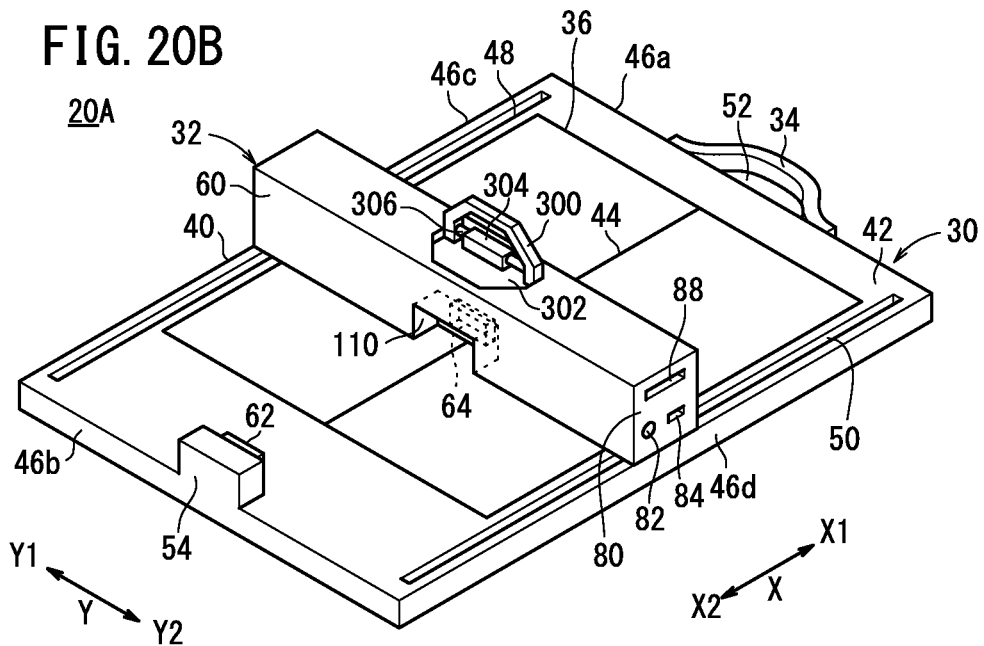

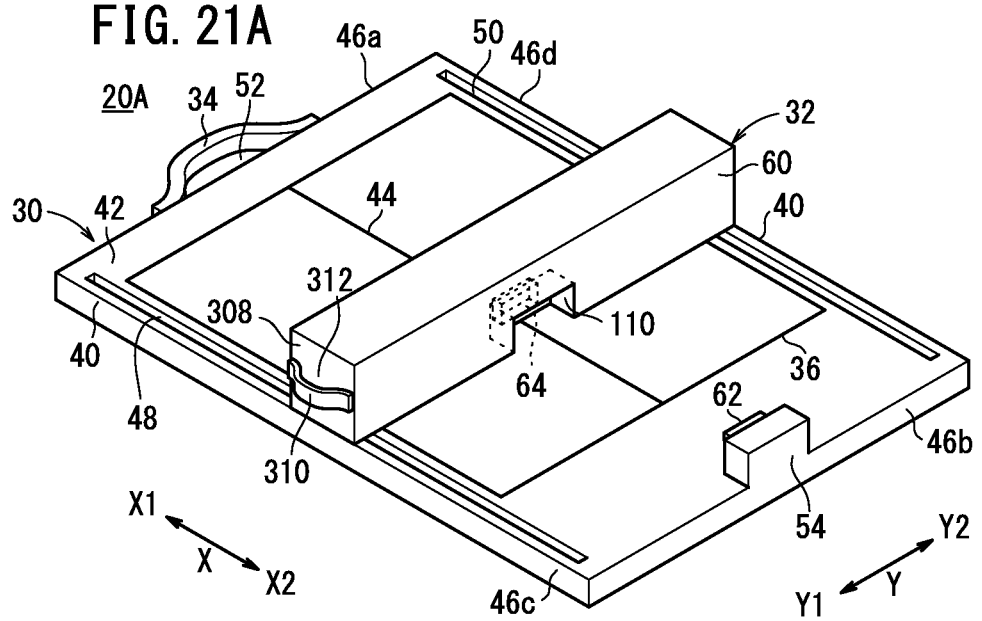
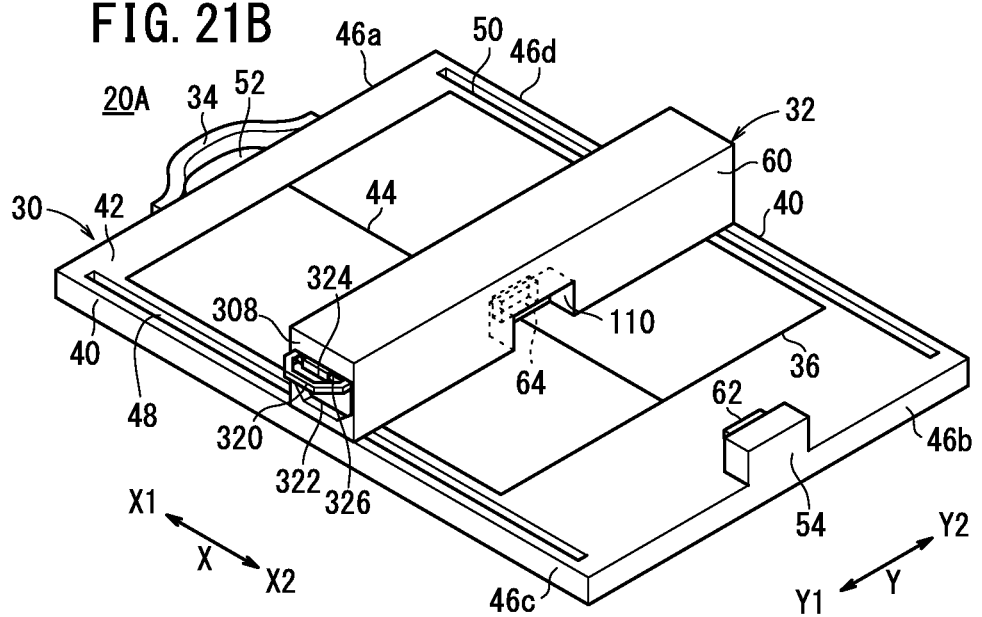

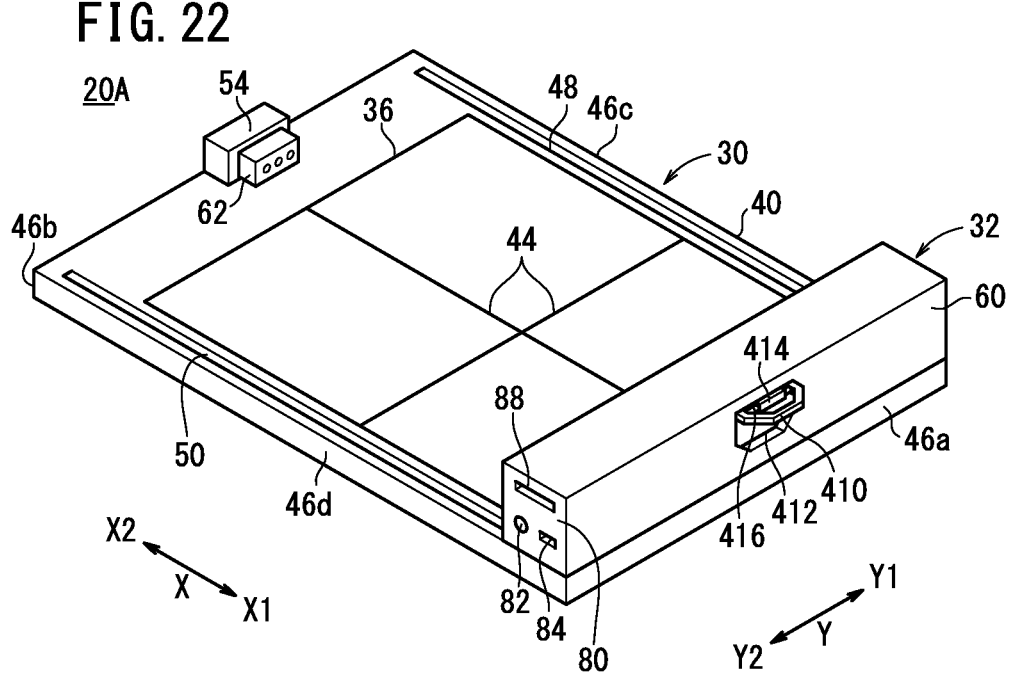

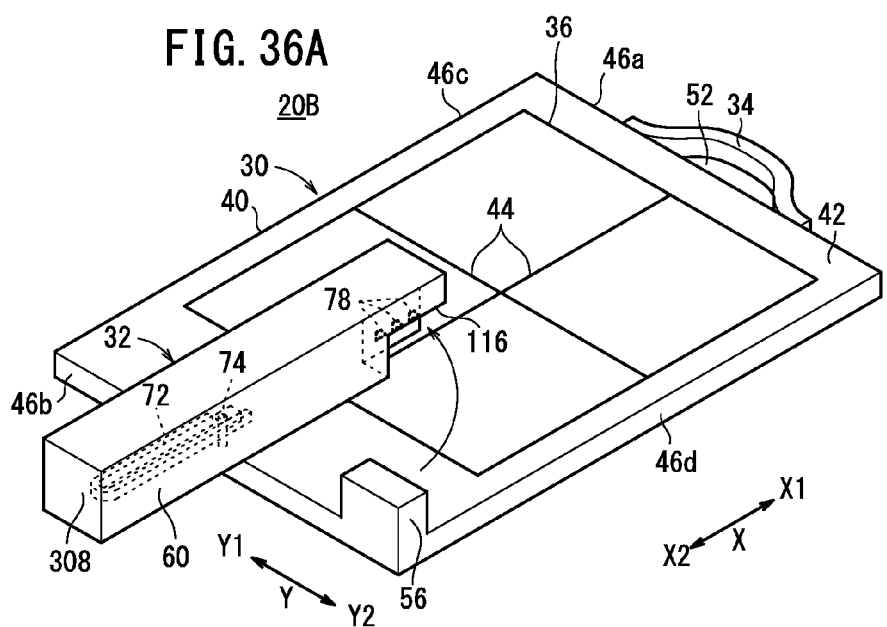
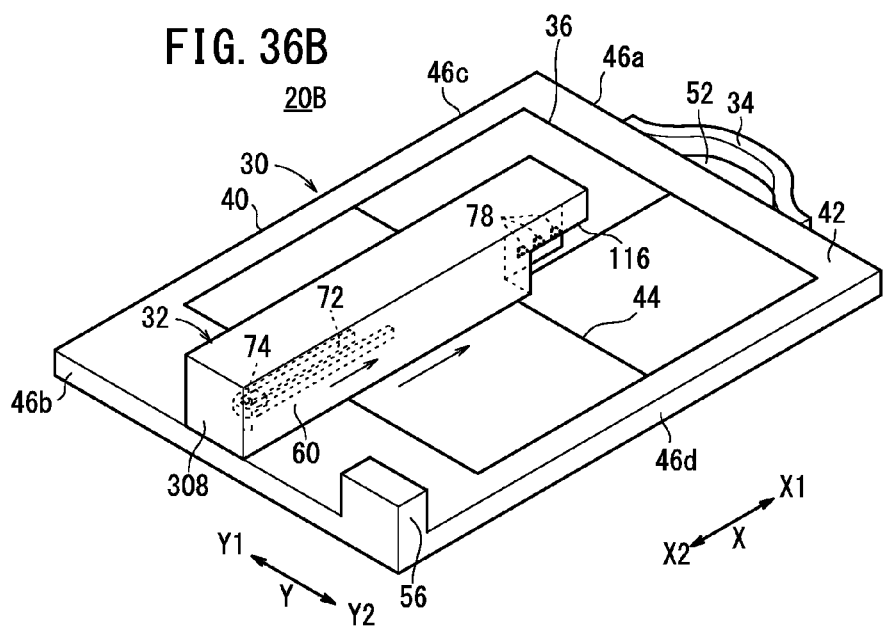

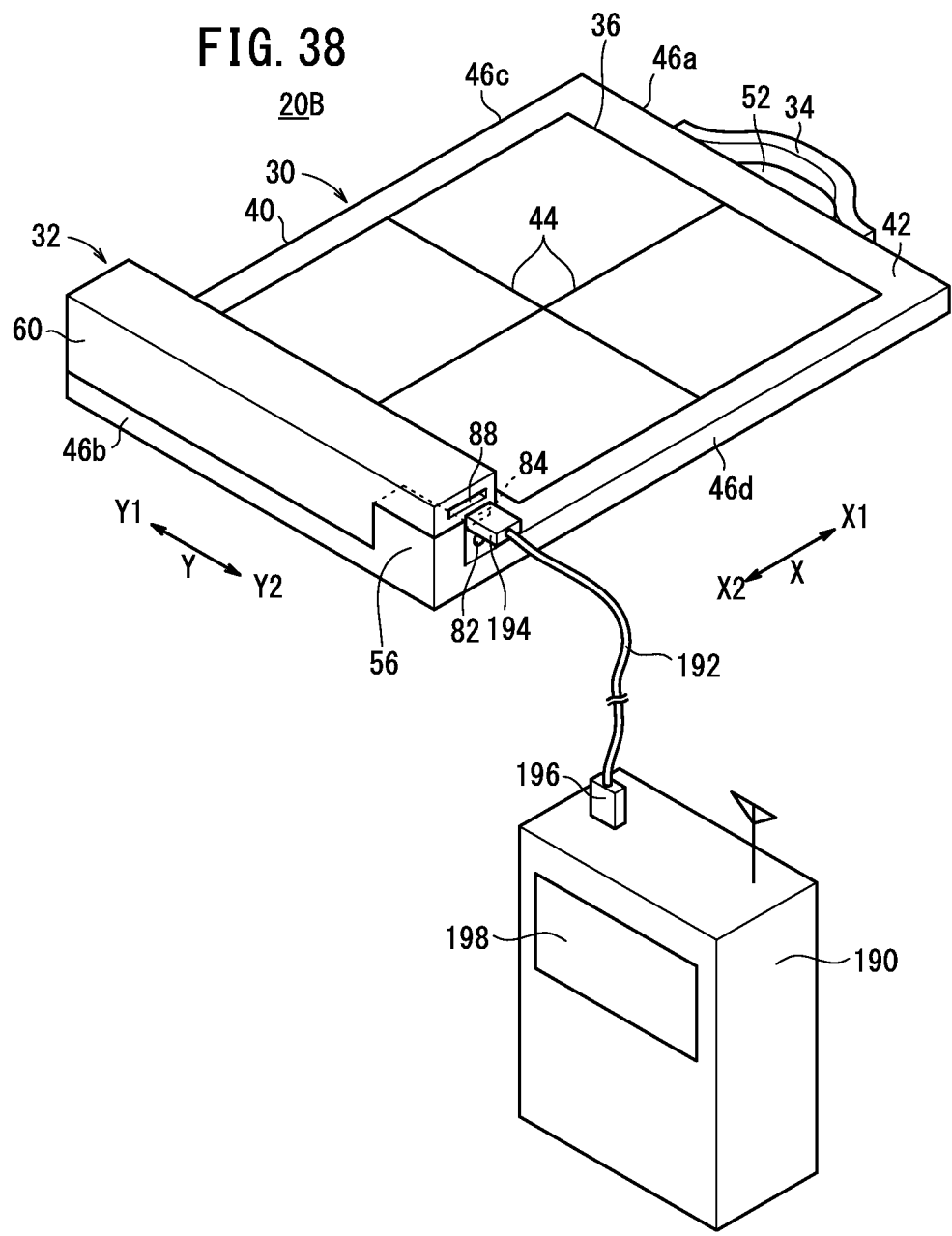

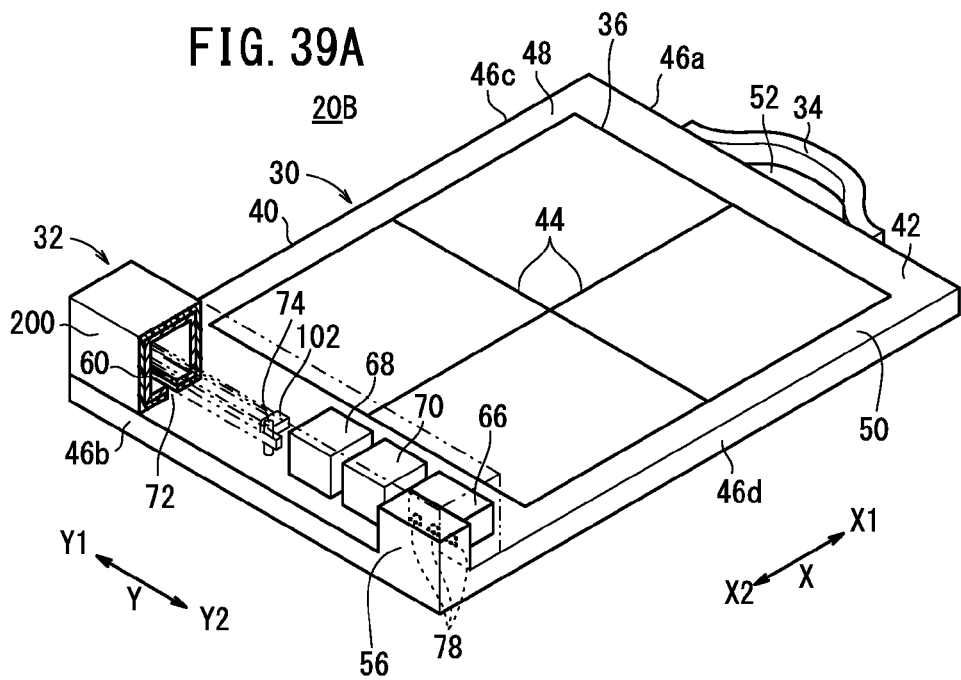
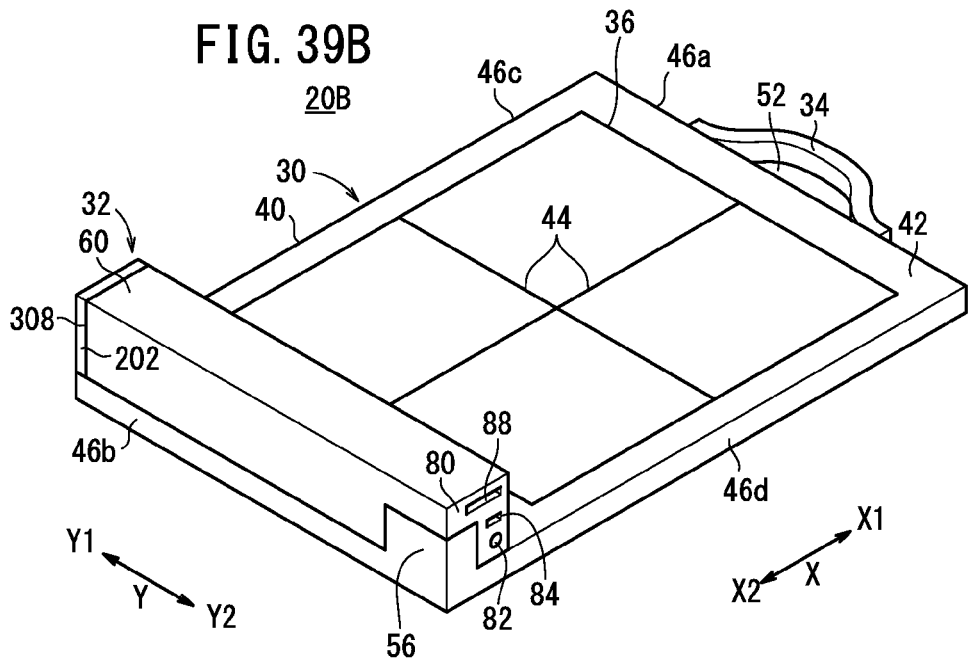

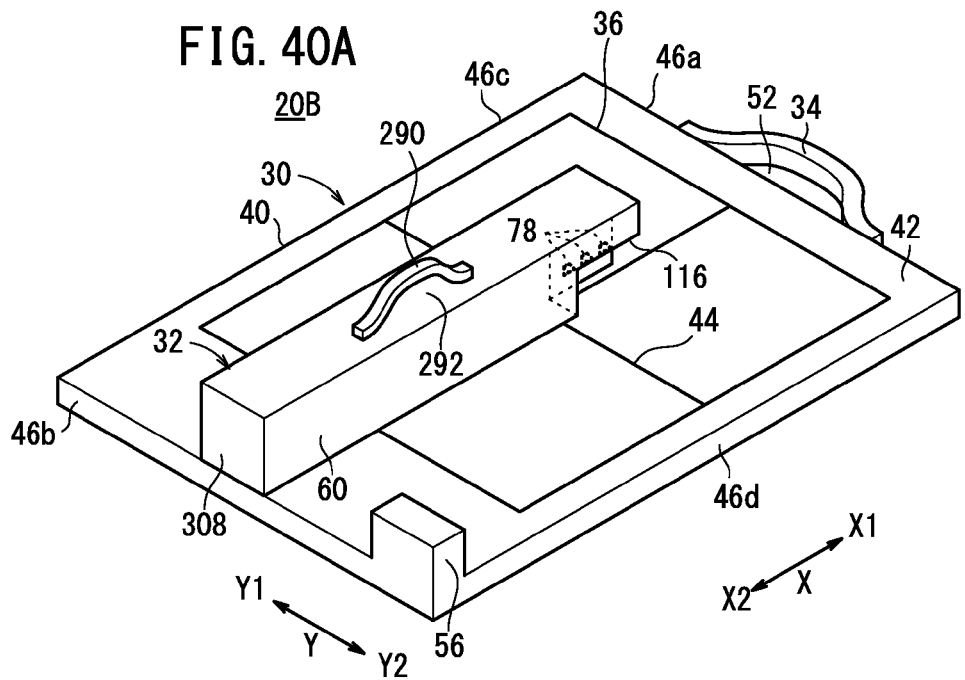
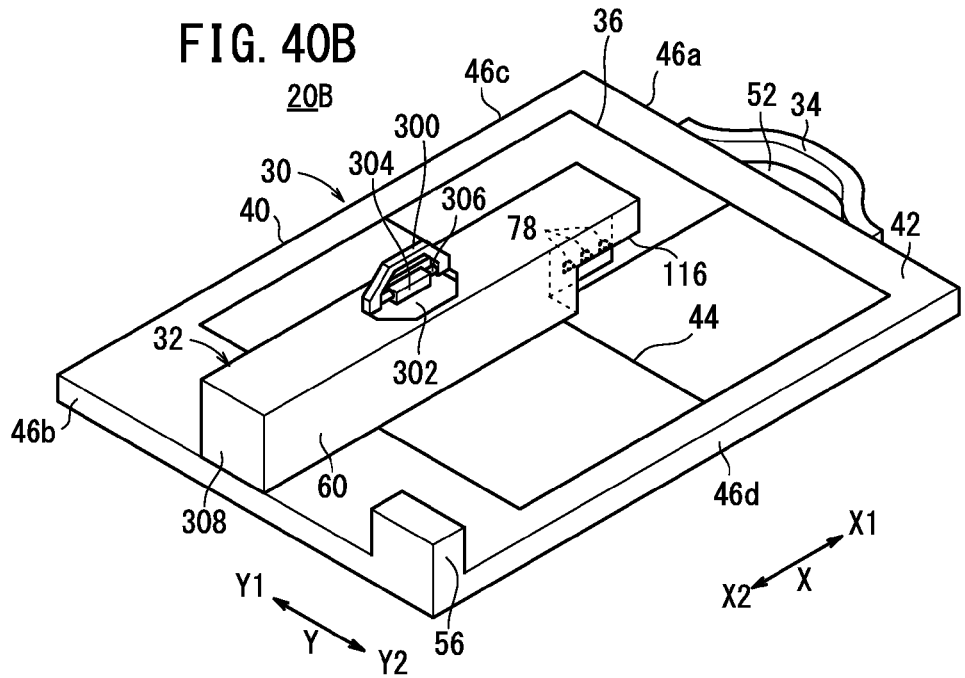

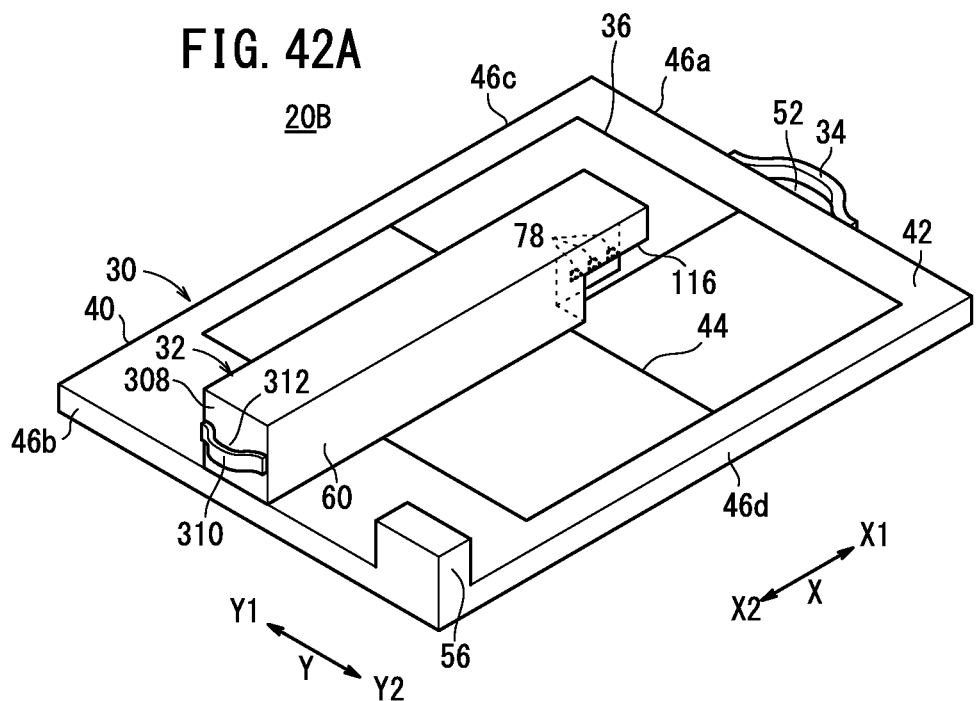
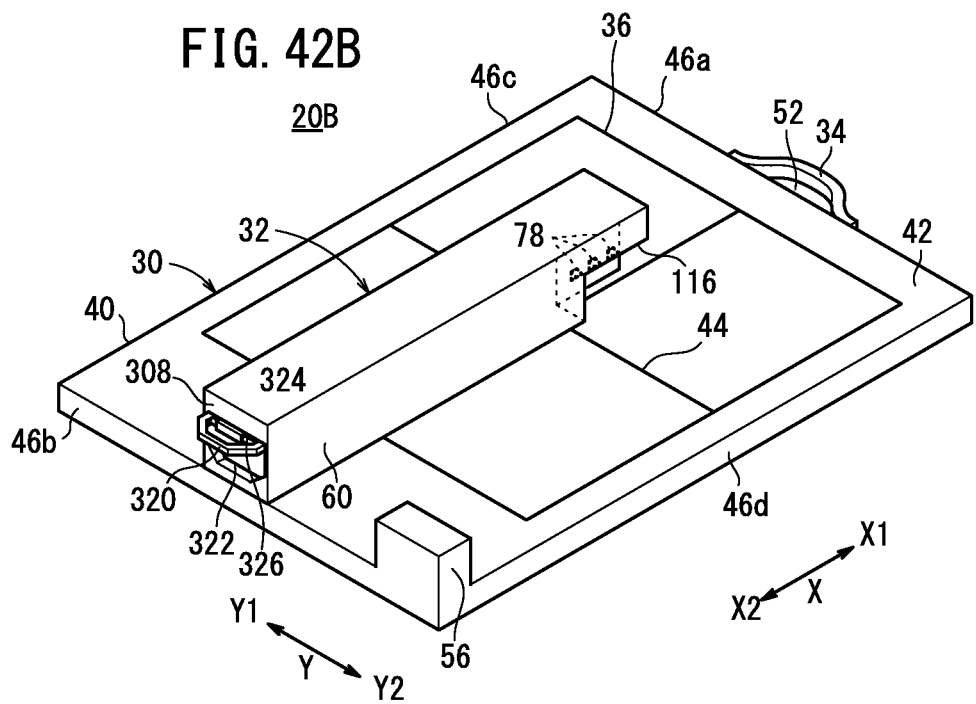

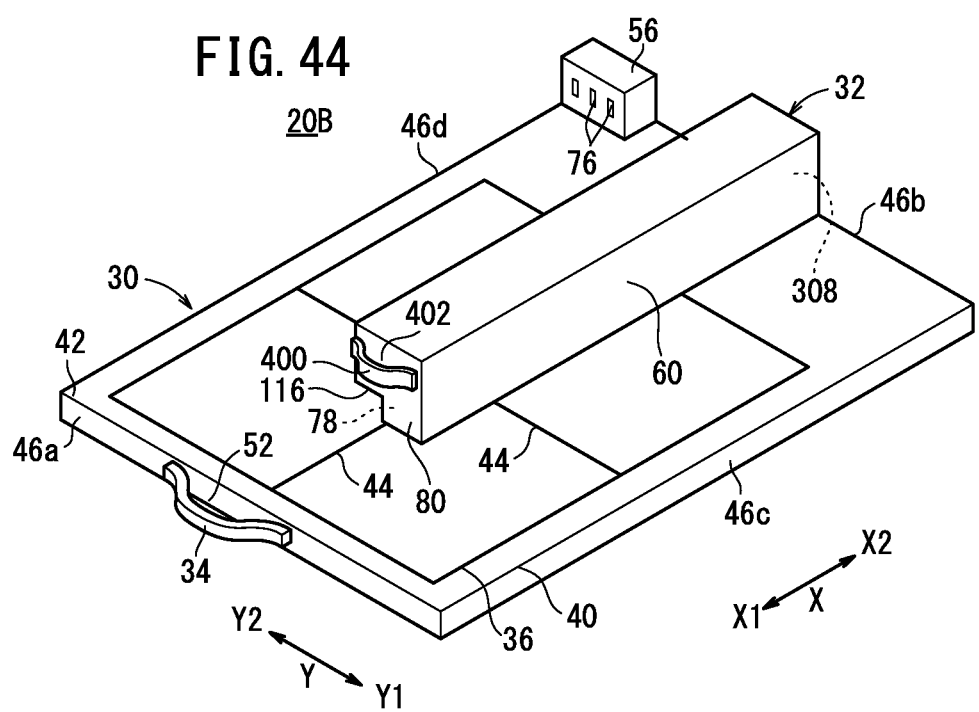

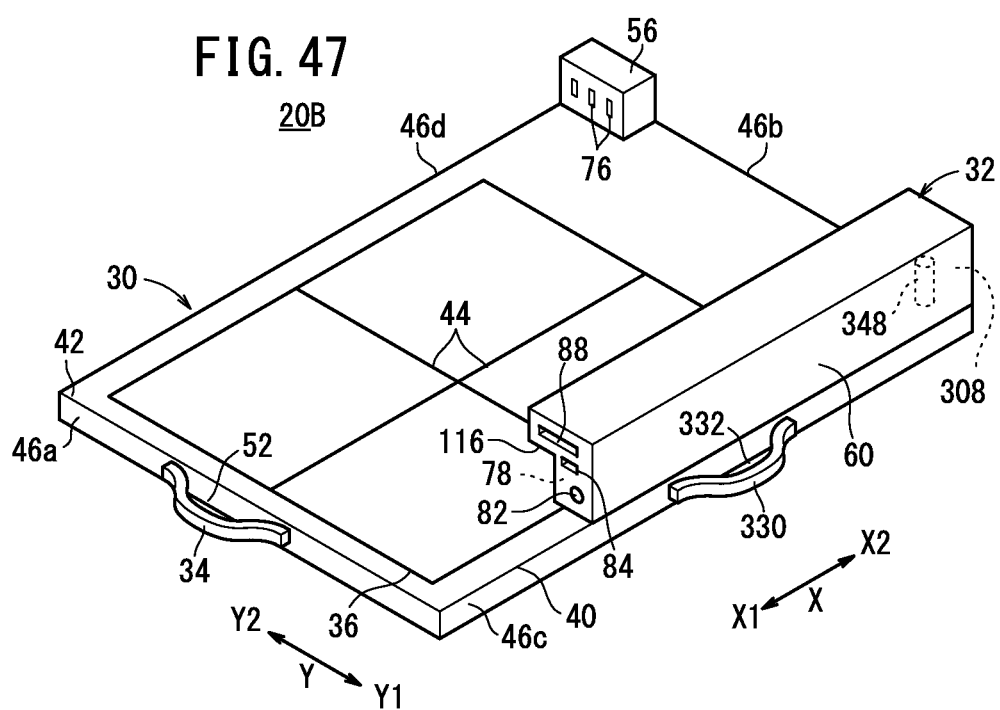

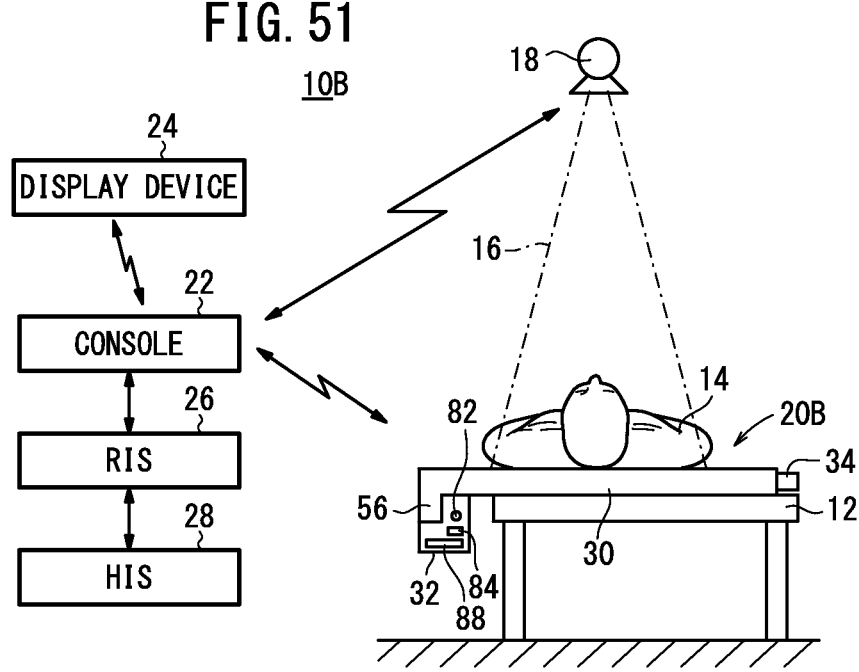

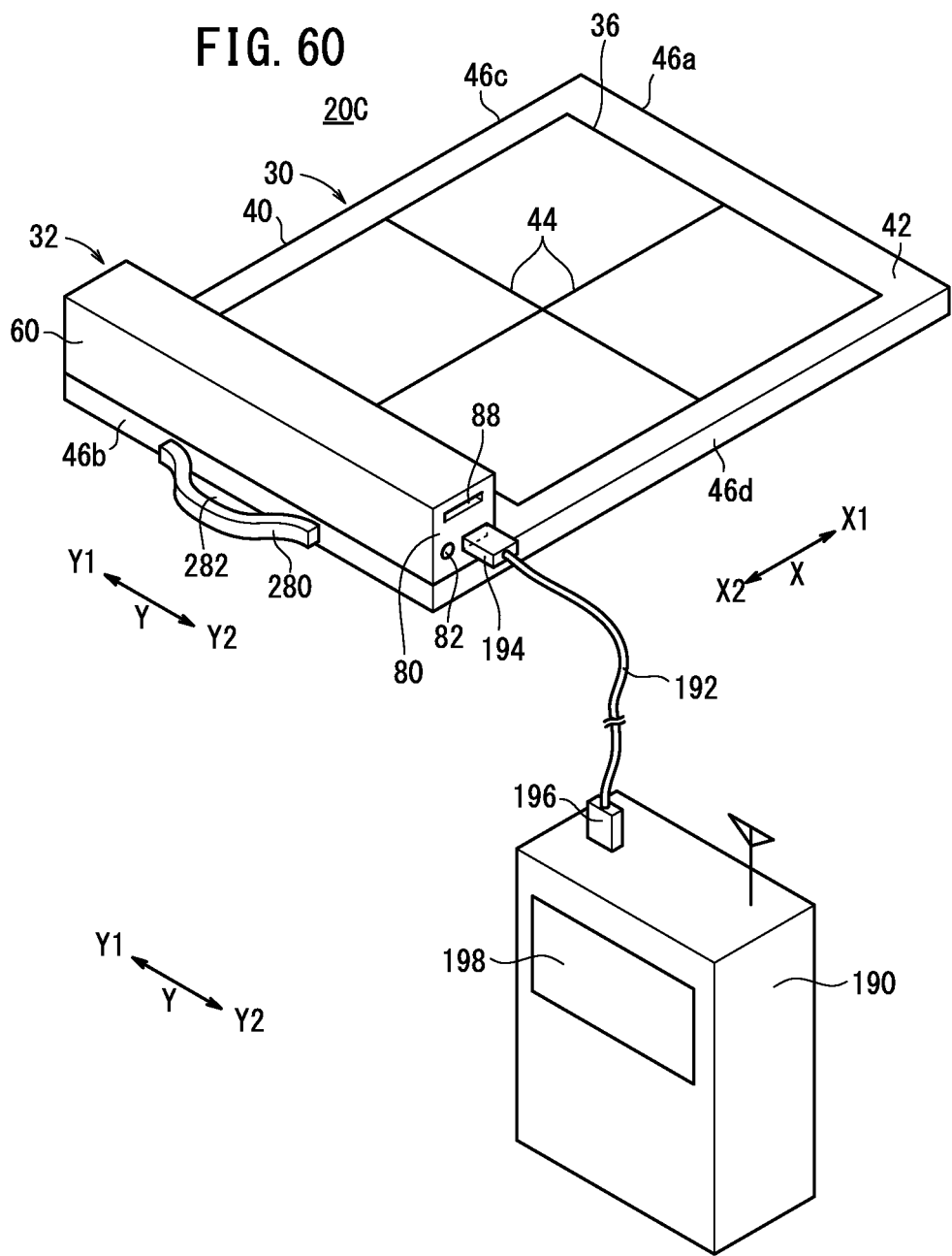

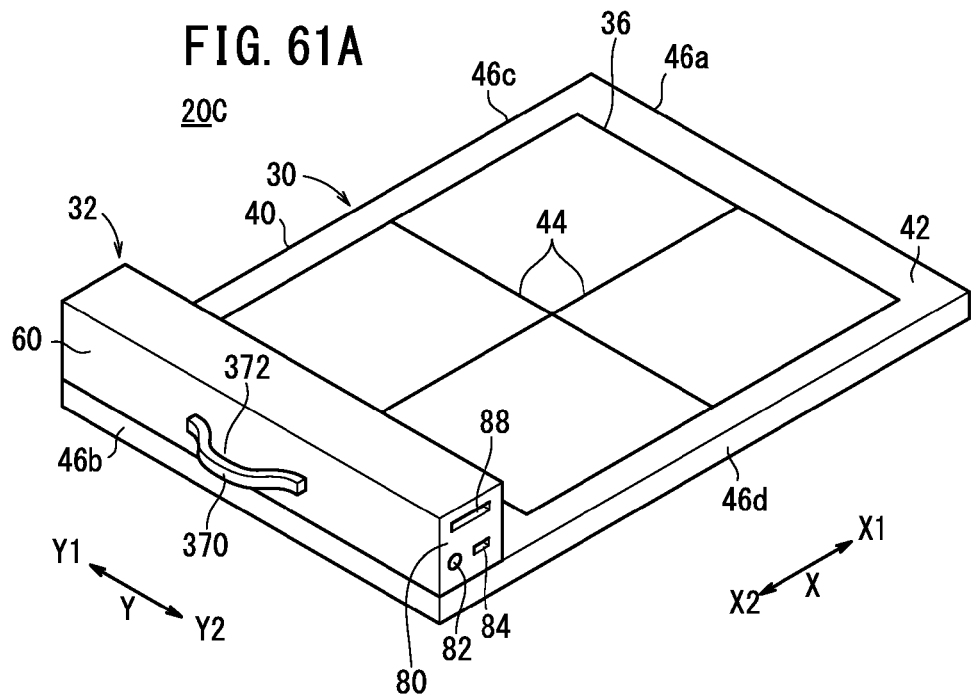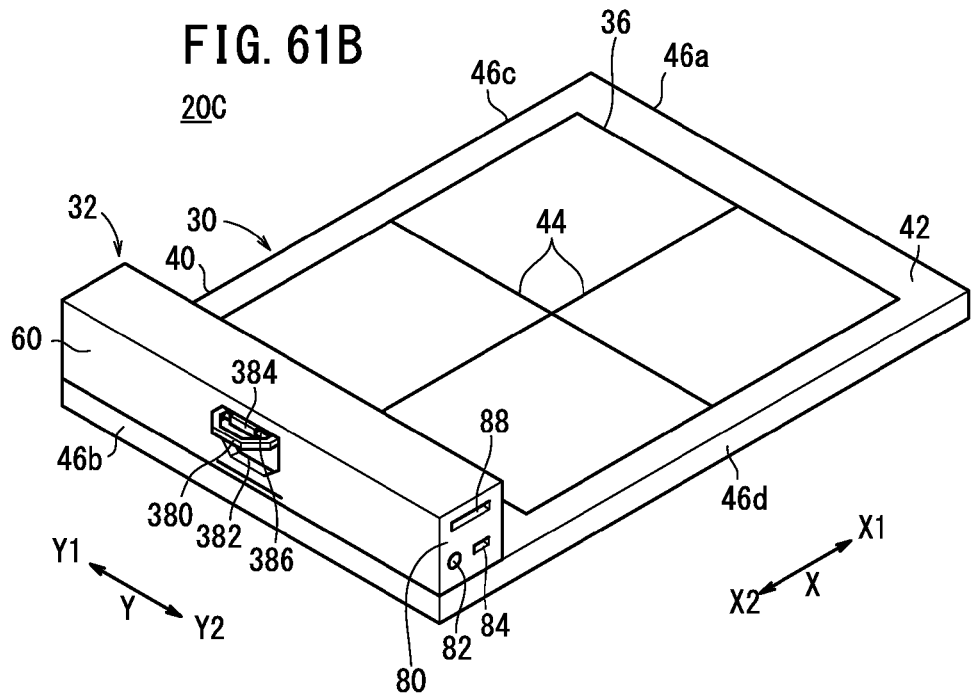

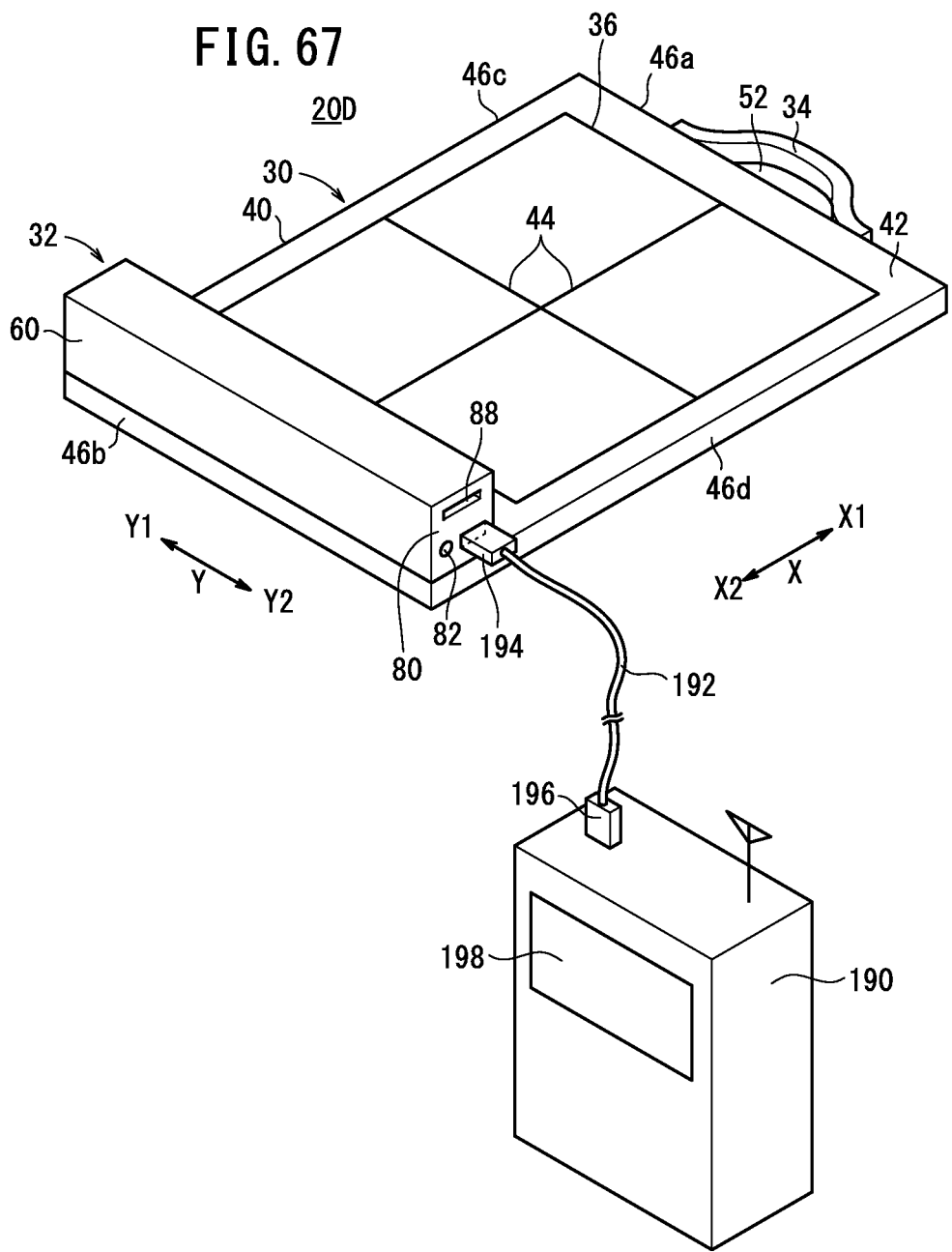

RADIOLOGICAL IMAGING DEVICE

CROSS-REFERENCE TO RELATED APPLICATIONS

The present invention is a 35 U.S.C. 371 National Stage Entry of PCT/JP2011/053334, filed Feb. 17, 2011, which claims priority from Japanese Patent Application Nos. 2010-043219, filed on Feb. 26, 2010, 2010-043235, filed on Feb. 26, 2010, 2010-043512, filed on Feb. 26, 2010, 2010-045604, filed on Mar. 2, 2010, 2010-275654, filed on Dec. 10, 2010, 2010-275656, filed on Dec. 10, 2010, 2010-275659, filed on Dec. 10, 2010, and 2010-275664, filed on Dec. 10, 2010, the contents all of which are herein incorporated by reference.

TECHNICAL FIELD

The present invention relates to a radiographic image capturing apparatus (radiological imaging device) having a panel unit housing therein a radiation conversion panel for converting radiation into a radiographic image, and a controller for controlling the radiation conversion panel.

BACKGROUND ART

In the medical field, there have widely been used radiographic image capturing apparatus, which apply radiation to a subject and guide radiation that has passed through the subject to a radiation conversion panel, thereby capturing a radiographic image of the subject. Known forms of radiation conversion panels include a radiation film for recording a radiographic image by way of exposure, and a stimulable phosphor panel for storing radiation energy representing a radiographic image in a phosphor and retrieving the radiographic image as stimulated light, which is emitted in response to application of exciting light. The radiation film with the radiographic image recorded therein is supplied to a developing apparatus to develop the recorded radiographic image. The stimulable phosphor panel with the radiographic image recorded therein is supplied to a reading apparatus to produce a radiographic image as a visible image.

In operating rooms or the like, it is necessary to immediately read radiographic images from radiation conversion panels and to display the radiographic images in order to treat patients as subjects quickly and appropriately. Radiation conversion panels that have been developed to meet such requirements include a direct-conversion-type radiation conversion panel, which employs a solid-state detector for converting radiation directly into electric signals, and an indirect-conversion-type radiation conversion panel, which employs a scintillator for converting radiation into visible light and a solid-state detector for converting the visible light into electric signals.

A direct-conversion-type or an indirect-conversion-type of radiation conversion panel is housed in a panel unit. A radiographic image recorded in the radiation conversion panel is read by a controller that controls the radiation conversion panel. The panel unit and the controller jointly make up a radiographic image capturing apparatus, which is referred to as an electronic cassette.

Such an electronic cassette should preferably be constructed so that the electronic cassette can be carried by a doctor or radiological technician (user).

Japanese Laid-Open Patent Publication No. 2008-256685 proposes a controller having an integral grip, which is removably connected to a panel unit and can be gripped by the user.

Japanese Laid-Open Patent Publication No. 2004-077641 proposes an electronic cassette with a grip attached to a side surface thereof and which is movable along the side surface.

Japanese Laid-Open Patent Publication No. 2002-082172 proposes an electronic cassette having a center of gravity disposed on the central line of a grip.

Japanese Laid-Open Patent Publication No. 2009-080103 proposes a panel unit and a controller, which are carried while being integrally coupled to each other. After the panel unit and the controller have been carried, a radiographic image is captured by the panel unit while the controller is spaced from the panel unit.

SUMMARY OF INVENTION

Problems to be Solved by the Invention and Objects of the Invention

Electronic cassettes incorporate relatively expensive electronic components, compared with radiographic image capturing apparatus that employ radiation films and stimulable phosphor panels, because the electronic cassettes read electric signals converted from radiation as representing a radiographic image. Consequently, when the user carries an electronic cassette, the user should pay full attention to safeguarding the electronic cassette against damage due to impacts upon falling or the like. For this reason, certain electronic cassettes have a grip, as disclosed in Japanese Laid-Open Patent Publication No. 2008-256685, Japanese Laid-Open Patent Publication No. 2004-077641, and Japanese Laid-Open Patent Publication No. 2002-082172.

Usually, the controller includes a power supply such as a battery for supplying electric power to the radiation conversion panel and to components in the controller as well as to a communication unit for communicating with external circuits. Therefore, the ratio of the weight of the controller to the weight of the electronic cassette is large. In addition, the power supply and the communication unit are often centralized in a certain area of the controller. Depending on the position of the controller in the electronic cassette, the weight distribution of the electronic cassette may be unbalanced. As a result, if the user grips the grip for carrying the electronic cassette, the electronic cassette may feel heavier than it actually is.

It is an object of the present invention to provide a radiographic image capturing apparatus that can be carried stably.

Another object of the present invention is to provide a radiographic image capturing apparatus, which can be carried stably by eliminating an unbalanced weight distribution of the radiographic image capturing apparatus.

DESCRIPTION OF THE INVENTION

To achieve the aforementioned objects, a radiographic image capturing apparatus according to the present invention includes a panel unit housing therein a radiation conversion panel for converting radiation into a radiographic image, and a controller disposed on the panel unit, for controlling the radiation conversion panel, wherein the controller is thicker than the panel unit or protrudes from the panel unit.

Since the panel unit is thinner than the controller or the controller protrudes from the panel unit, the radiographic image capturing apparatus is made thin and lightweight.

The controller is disposed in a location outside of an area of the panel unit that is irradiated with radiation that has passed through a subject at least during an image capturing process. More desirably, the controller is disposed in a location outside of an image capturing area of the panel unit that is capable of being irradiated with radiation. Therefore, the controller does not present an obstacle to capturing of radiographic images.

The controller is movable along a surface of the panel unit.

More specifically, the radiographic image capturing apparatus further includes a moving mechanism for translating the controller along the surface of the panel unit with respect to the panel unit.

With the above arrangement, in a case where the controller, which is responsible for an unbalanced weight distribution, is translated with respect to the panel unit by the moving mechanism, the center of gravity of the radiographic image capturing apparatus can be changed with ease.

More specifically, since the ratio of the weight of the controller to the overall weight of the radiographic image capturing apparatus is relatively large, if the controller is displaced from a geometrically central position of the radiographic image capturing apparatus, then the center of gravity of the radiographic image capturing apparatus does not coincide with the central position, and the radiographic image capturing apparatus is in an eccentric state. Therefore, the radiographic image capturing apparatus has an unbalanced weight distribution as a whole.

According to the present invention, the controller is translated with respect to the panel unit to bring the central position and the center of gravity into substantial agreement with each other, for thereby easily eliminating the unbalanced weight distribution. Since the radiographic image capturing apparatus feels light when carried by the user, the user can carry the radiographic image capturing apparatus stably and easily. As a result, the user can carry the radiographic image capturing apparatus without dropping the radiographic image capturing apparatus or causing the controller to hit other objects. Thus, the user experiences a reduced burden upon carrying the radiographic image capturing apparatus.

According to the present invention, as described above, since the unbalanced weight distribution of the radiographic image capturing apparatus is easily eliminated by translating the controller with respect to the panel unit with the moving mechanism, the user can carry the radiographic image capturing apparatus in a stable manner.

Preferably, the panel unit includes a substantially rectangular first housing permeable to radiation, the radiation conversion panel being housed in the first housing, and the moving mechanism includes a substantially straight guide disposed on a surface of the first housing other than the image capturing area, and a moving member is capable of being translated in unison with the controller along the guide.

Since the moving member and the controller are linearly translated in unison with each other along the guide, the controller can be translated with respect to the panel unit by a simple mechanism. Even though the controller may be disposed over the image capturing area during carrying of the radiographic image capturing apparatus, the controller can be retracted away from the image capturing area during the image capturing process. Therefore, the controller and the guide do not present an obstacle to capturing of radiographic images.

The controller may be turned, rather than being translated, with respect to the panel. More specifically, the radiographic image capturing apparatus may further include a moving mechanism for turning the controller along the surface of the panel unit with respect to the panel unit.

With the above arrangement, using the moving mechanism, the center of gravity of the radiographic image capturing apparatus can be changed easily by turning the controller, which is responsible for an unbalanced weight distribution, with respect to the panel unit.

The controller is turned with respect to the panel unit to bring the central position and the center of gravity into substantial agreement with each other, for thereby easily eliminating the unbalanced weight distribution. Similar to the case of translating the controller, since the radiographic image capturing apparatus feels light when carried by the user, the user can carry the radiographic image capturing apparatus stably and easily. As a result, the user can carry the radiographic image capturing apparatus without dropping the radiographic image capturing apparatus or causing the controller to hit other objects. Thus, the user experiences a reduced burden upon carrying the radiographic image capturing apparatus.

Inasmuch as the unbalanced weight distribution of the radiographic image capturing apparatus is easily eliminated by turning the controller with respect to the panel unit using the moving mechanism, the user can carry the radiographic image capturing apparatus stably.

The panel unit includes a substantially rectangular first housing permeable to radiation, the radiation conversion panel being housed in the first housing, and the moving mechanism includes a shaft disposed on a surface of the first housing other than the image capturing area, for turning the controller about the shaft.

Since the controller is capable of being turned about the shaft, the controller can be turned with respect to the panel unit by a simple mechanism. Even though the controller may be disposed over the image capturing area during carrying of the radiographic image capturing apparatus, the controller can be retracted away from the image capturing area during the image capturing process. Therefore, the controller and the shaft do not present an obstacle to capturing of radiographic images.

The controller includes a panel controller for driving the radiation conversion panel and reading the radiographic image from the radiation conversion panel, a communication unit for communicating with an external circuit, and a power supply for supplying electric power to the panel controller, the communication unit, and the radiation conversion panel.

If the controller is moved (translated or turned), the power supply stops supplying electric power to the communication unit and the panel unit. Therefore, wasteful electric power consumption is minimized.

The panel unit includes a connector for electrically connecting the radiation conversion panel and the controller to each other, and the power supply stops supplying electric power to the communication unit and the radiation conversion panel if the connector and the controller are spaced away from each other and are electrically disconnected from each other while the controller is moved. Therefore, wasteful electric power consumption is reliably minimized.

The panel controller may include a connection detector for detecting whether or not the connector and the controller are electrically connected to each other.

The panel controller is electrically connected to the radiation conversion panel through the connector. In the case that the connection detector detects whether or not the connector and the controller are electrically connected to each other, the timing at which to control the panel unit, and the timing at which to read radiographic images from the radiation conversion panel can easily be grasped.

The controller and/or the panel unit has a grip that is gripped by a user. The grip allows the user to carry the radiographic image capturing apparatus with ease.

The panel unit includes a substantially rectangular first housing permeable to radiation, the radiation conversion panel being housed in the first housing, the controller is disposed in a location outside of the image capturing area on the surface of the first housing at least during the image capturing process, and the grip is disposed on a side surface of the first housing, an upper surface of a substantially rectangular second housing of the controller, and/or a side surface of the second housing.

In the case that the controller is disposed on the surface of the first housing near a side surface thereof at least during the image capturing process, the grip is disposed on a side surface of the first housing, another side surface of the first housing, another surface thereof interconnecting the side surface and the other side surface, the upper surface of the second housing, and/or the side surface of the second housing.

The grip disposed on the panel unit also allows the user to carry the radiographic image capturing apparatus with ease.

With the grip being disposed on the controller, since the user grips the grip and holds the controller, which is relatively heavy, upon carrying the radiographic image capturing apparatus, the carrying stability of the radiographic image capturing apparatus is increased.

If the controller is movable with respect to the panel unit, then the user can easily move the controller with respect to the panel unit while the user grips the grip.

With the grip being disposed on the controller, the grip may be pulled from the upper surface or side surface of the second housing, and then gripped when the radiographic image capturing apparatus is carried or the controller is moved. If the grip comprises a foldable grip, which is pulled out only if the radiographic image capturing apparatus is carried or the controller is moved, then the grip does not present an obstacle to capturing of radiographic images. Thus, the radiographic image capturing apparatus can be handled with increased ease.

Preferably, the radiation conversion panel includes a scintillator for converting radiation into visible light, solid-state detectors for converting visible light into an electric signal representing the radiographic image, switching elements for reading electric signals from the solid-state detectors, and a substrate on which the solid-state detectors and the switching elements are disposed. The substrate comprises a flexible plastic substrate, the solid-state detectors are made of an organic photoconductor, and the switching elements are made of an organic semiconductor material.

It is thus possible to grow the solid-state detectors and the switching elements at a low temperature on the substrate, and also to make the radiation conversion panel and the panel unit that houses the radiation conversion panel therein thin and lightweight. Such a flexible substrate enables the radiation conversion panel and the panel unit, which houses the radiation conversion panel therein, to be made flexible. As a result, the radiation conversion panel is prevented from being damaged under loads in a case, for example, where the subject is placed on the panel unit.

If the substrate, the switching elements, the solid-state detectors, and the scintillator, which is made of CsI, are arranged in this order along a direction in which radiation is applied, then it is possible to produce high-quality radiographic images.

The structure and advantages of the radiographic image capturing apparatus according to the present invention have been described above. Further specific structural details and advantages of the present invention (structural details and advantages of first through fourth inventions) will be described below.

Description of the First Invention

The first invention is concerned with a radiographic image capturing apparatus, which includes a moving mechanism for translating the controller with respect to the panel unit.

According to the first invention, the guide on the first housing extends along directions substantially perpendicular to two opposite sides of at least one of an irradiation surface that is irradiated with radiation and having the image capturing area, and a side surface of the first housing.

The guide extends along longitudinal directions of the first housing, and the moving member and the controller can be translated linearly in unison with each other along the guide. As a result, the central position and the center of gravity are easily brought into agreement with each other, for thereby reliably eliminating unbalanced weight distribution.

The image capturing area may be defined substantially centrally on the irradiation surface, and two guides may be provided in sandwiching relation to the image capturing area between the two opposite sides of the irradiation surface. Alternatively, the guides may be provided parallel to each other on two respective opposite side surfaces of the first housing.

Two moving members are mounted on the controller and disposed on the respective two guides. As a result, the controller and the two moving members can be translated more stably and reliably along the two guides.

The guides may comprise substantially straight recesses, grooves, or rails provided on surfaces of the first housing. The moving members may comprise sliders linearly slidable along the recesses or the rails, or wheels linearly movable along the grooves, whereby the controller can be translated simply and reliably with respect to the panel unit.

Stop members may be disposed in the recesses or the grooves, or on the rails, for stopping the sliders from sliding along the recesses or the rails, or for stopping the wheels from moving along the grooves, whereby the controller can be stopped at any desired position with respect to the panel unit.

The stop members may comprise teeth disposed in the recesses or the grooves, or on the rails, for stopping the sliders from sliding, or for stopping the wheels from moving upon abutment against the sliders or the wheels, whereby the controller can be reliably stopped at any desired position with respect to the panel unit.

Description of the Second Invention

The second invention is concerned with a radiographic image capturing apparatus, which includes a moving mechanism for turning the controller with respect to the panel unit.

According to the second invention, the moving mechanism includes an oblong hole defined in the second housing, with the shaft extending through the oblong hole. The controller is rotatable about the shaft and is movable along the hole with respect to the shaft.

In the case that the controller is turned about the shaft with respect to the panel unit, and is moved along the oblong hole with respect to the panel unit, the central position and the center of gravity are easily brought into agreement with each other for thereby reliably eliminating unbalanced weight distribution.

The shaft may be disposed in a location outside of the image capturing area on the irradiation surface of the first housing. The oblong hole may be defined in a bottom surface, near the irradiation surface, of the second housing, and may extend in the longitudinal direction of the second housing.

Therefore, the controller can be moved more stably and reliably along the longitudinal direction.

A protrusion is mounted on a distal end of the shaft, which is inserted into the second housing. The protrusion extends in a radial direction of the shaft, and has a width that is substantially the same as the diameter of the shaft. A movement limiting member, which is disposed on the bottom surface of the second housing, substantially surrounds the hole as viewed in plan, and is open at one end of the hole. The shaft extends through the end of the hole. In a case where the controller is turned about the shaft, one end and another end of the movement limiting member abut against the protrusion at an opening thereof, thereby defining an angular range within which the controller can be turned about the shaft. With the protrusion disposed in the hole as viewed in plan, the movement limiting member is brought into contact with the distal end of the shaft and the protrusion, so as to limit the direction along which the controller is moved with respect to the shaft.

The one end and the other end of the movement limiting member at the opening thereof, and the protrusion define the angular range within which the controller can be turned about the shaft. The movement limiting member, the distal end of the shaft, and the protrusion set the direction along which the controller is moved with respect to the shaft. The distance that the controller moves along the above direction is determined depending on the length of the oblong hole. Thus, with the movement limiting member and the protrusion, it is possible to turn the controller with respect to the panel unit accurately and with good precision.

If stop members are provided on the movement member and are disposed in the opening for contacting the protrusion in order to stop the controller from moving along the hole, then the controller can be stopped at any desired position with respect to the panel unit.

If the stop members comprise teeth for stopping the controller from moving by coming into abutment against the protrusion, then the controller can be reliably stopped at any desired position with respect to the panel unit.

It has been described that the controller is turned with respect to the panel unit based on the oblong hole and the shaft. However, the second invention is not limited to such a description. The controller may also be turned in the following manner.

The moving mechanism may further include a hole defined in the second housing with the shaft extending through the hole, whereby the controller is capable of being turned about the shaft.

With the above arrangement, since the center of gravity can be brought close to the central position, the unbalanced weight distribution is minimized.

The shaft may be disposed in a location outside of the image capturing area on the irradiation surface of the first housing, and the hole may be defined in a bottom surface, near the irradiation surface, of the second housing. The controller can thus be turned more stably and reliably.

A protrusion is mounted on a distal end of the shaft, which is inserted into the second housing. The protrusion extends in a radial direction of the shaft. A rotation limiting member, which is disposed on the bottom surface of the second housing, substantially surrounds the hole as viewed in plan, and is partially open. In the case that the controller is turned about the shaft, one end and another end of the rotation limiting member at the opening thereof abut against the protrusion, thereby defining an angular range within which the controller is capable of being turned about the shaft.

The one end and the other end of the rotation limiting member at the opening thereof, and the protrusion define the angular range within which the controller can be turned about the shaft. Therefore, it is possible to turn the controller with respect to the panel unit accurately and with high precision.

Description of the Third Invention

The third invention is concerned with a radiographic image capturing apparatus, wherein the grip is disposed on the controller and/or on the panel unit in the vicinity of the controller.

With the above arrangement, the user can carry the radiographic image capturing apparatus by gripping the grip, which is disposed on the heavy controller.

According to the third invention, in the radiographic image capturing apparatus, the weight distribution of which is shifted toward the controller, the grip is disposed on the controller and/or on the panel unit in the vicinity of the controller. The user carries the radiographic image capturing apparatus by gripping the grip, with the controller and the grip on an upper portion thereof. Since the user grips the heavy controller through the grip, the radiographic image capturing apparatus feels light upon being carried by the user. Therefore, the user can carry the radiographic image capturing apparatus stably and easily. Consequently, the user can carry the radiographic image capturing apparatus without dropping the radiographic image capturing apparatus or causing the controller to hit other objects. Thus, the user experiences a reduced burden upon carrying the radiographic image capturing apparatus.

According to the third invention, therefore, since the grip is disposed on or near the controller, the user can grip the heavy controller through the grip. Therefore, the user can carry the radiographic image capturing apparatus in a stable manner.

The controller is disposed on a side surface of the first housing while remaining in contact with the first housing.

The controller may be disposed in any position insofar as the controller is disposed on a side surface of the first housing. For example, the controller may be disposed on a side surface at the irradiation surface, which is irradiated with radiation, of the first housing, a side surface of the first housing, or a side surface on the reverse side of the first housing. Therefore, the grip is disposed on the controller and/or in the vicinity of the controller, which is disposed on the side surface of the first housing.

In the case that the user carries the radiographic image capturing apparatus, the grip and the controller are reliably positioned on an upper portion of the radiographic image capturing apparatus. Consequently, the user can carry the radiographic image capturing apparatus in a stable manner.

If the controller is disposed on the irradiation surface, which is irradiated with radiation, of the first housing, then the grip and the controller are positioned on an upper portion of the radiographic image capturing apparatus at times that the user carries the radiographic image capturing apparatus, and the radiographic image capturing apparatus is disposed on an image capturing base at times that the irradiation surface and the controller face upwardly during capturing of radiographic images by the radiographic image capturing apparatus. As a result, the radiographic image capturing apparatus can be carried and placed in any position with ease, and can be handled easily.

If the grip is disposed on the side surface of the first housing in the vicinity of the controller, then the grip and the controller are positioned at an uppermost position of the radiographic image capturing apparatus at times that the user carries the radiographic image capturing apparatus. Therefore, the carrying stability of the radiographic image capturing apparatus is further increased.

If the grip is disposed directly on an upper surface or a side surface of the second housing, then the grip and the controller are positioned at an uppermost position of the radiographic image capturing apparatus at times that the user carries the radiographic image capturing apparatus. Therefore, the user directly grips the controller through the grip, whereby the carrying stability of the radiographic image capturing apparatus is further increased significantly.

Description of the Fourth Invention

The fourth invention is concerned with a radiographic image capturing apparatus, wherein the controller is disposed on one end of the panel unit, and the grip is disposed on another end of the panel unit.

With the above arrangement, the user carries the radiographic image capturing apparatus by gripping the grip with the grip being disposed on an upper portion of the radiographic image capturing apparatus, whereas the controller, which is heavy, is disposed on a lower portion of the radiographic image capturing apparatus.

According to the fourth invention, in the radiographic image capturing apparatus, the weight distribution of which is shifted toward the controller, the grip is disposed in a position opposite to the controller. The user carries the radiographic image capturing apparatus by gripping the grip, with the grip being disposed on an upper portion of the radiographic image capturing apparatus, whereas the controller, which is heavy and is responsible for unbalanced weight distribution, is disposed on a lower portion of the radiographic image capturing apparatus. Since the user grips the grip while the center of gravity of the entire radiographic image capturing apparatus is low, the radiographic image capturing apparatus feels light upon being carried by the user. The user can thus carry the radiographic image capturing apparatus stably and easily. Consequently, the user can carry the radiographic image capturing apparatus without dropping the radiographic image capturing apparatus or causing the controller to hit other objects. Further, the user experiences a reduced burden upon carrying the radiographic image capturing apparatus.

The controller includes electronic components for controlling the radiation conversion panel, and a power supply such as a battery or the like. The temperature of the controller tends to be increased due to heat generated by the electronic components and the power supply. According to the fourth invention, since the controller and the grip are disposed opposite to each other, heat from the controller is reliably prevented from being transmitted to the grip. Therefore, the user can grip the grip and carry the radiographic image capturing apparatus without having to worry about heat.

According to the fourth invention, as described above, since the grip and the controller are disposed opposite to each other on the panel unit, the user grips the grip while the entire radiographic image capturing apparatus maintains a low center of gravity. Therefore, the user can carry the radiographic image capturing apparatus in a stable manner.

The controller is disposed in contact with a surface of the first housing at one end thereof, whereas the grip is disposed on the other end of the first housing.

The controller may be disposed in any position insofar as the controller is disposed on the one end of the first housing. For example, the controller may be disposed on a face side of the first housing at the one end, on a side surface of the first housing at the one end, or on a reverse side of the first housing at the one end. The grip may be disposed in any position insofar as the grip is disposed on the other end of the first housing. For example, the grip may be disposed on a face side of the first housing at the other end, on a side surface of the first housing at the other end, or on a reverse side of the first housing at the other end.

With the controller and the grip being disposed in the above locations in or on the first housing, the grip is reliably positioned on an upper portion of the radiographic image capturing apparatus, and the controller is reliably positioned on a lower portion of the radiographic image capturing apparatus while the user carries the radiographic image capturing apparatus. Consequently, stability is achieved at times that the user carries the radiographic image capturing apparatus.

Among the side surfaces of the first housing, if the controller is disposed on one side of the irradiation surface of the first housing, which includes the image capturing area that is irradiated with radiation, whereas the grip is disposed on a side surface of another side of the irradiation surface, then at times that the user carries the radiographic image capturing apparatus, the grip is positioned in an uppermost position of the radiographic image capturing apparatus, while the controller is positioned in a lowermost position of the radiographic image capturing apparatus. Accordingly, the carrying stability of the radiographic image capturing apparatus is further enhanced.

Preferably, the radiographic image capturing apparatus further includes a cushioning member, which covers the second housing entirely or partially.

As described above, in the case that the user carries the radiographic image capturing apparatus, the controller is positioned at a lowermost position of the radiographic image capturing apparatus. The cushioning member is effective to protect the controller from impacts if the controller hits another object, or if the user drops the radiographic image capturing apparatus.

Principal Advantages of the First through Fourth Inventions

According to the first invention, as described above, since an unbalanced weight distribution of the radiographic image capturing apparatus is eliminated easily by translating the controller with respect to the panel unit using the moving mechanism, the user can carry the radiographic image capturing apparatus in a stable manner.

According to the second invention, since an unbalanced weight distribution of the radiographic image capturing apparatus is eliminated easily by turning the controller with respect to the panel unit using the moving mechanism, the user can carry the radiographic image capturing apparatus in a stable manner.

According to the third invention, since the grip is disposed on the controller and the user grips the heavy controller through the grip, the user can carry the radiographic image capturing apparatus in a stable manner.

According to the fourth invention, since the grip and the controller are disposed opposite to each other on the panel unit, and the user grips the grip while the radiographic image capturing apparatus maintains a low center of gravity, the user can carry the radiographic image capturing apparatus in a stable manner.

BRIEF DESCRIPTION OF DRAWINGS

FIGS. 9A through 9C are plan views showing the manner in which the cassette is carried;

FIG. 12 is a flowchart of a process of capturing an image using the cassette shown in FIG. 1;

FIG. 13 is a perspective view showing how the cassette is charged;

FIG. 17 is a cross-sectional view taken along line XVII-XVII of FIG. 16;

FIGS. 20A and 20B are perspective views of cassettes, which include grips provided respectively on controllers and panel units;

FIGS. 21A and 21B are perspective views of cassettes, which include grips provided respectively on controllers and panel units;

FIG. 22 is a perspective view of a cassette, which includes a grip provided on a controller;

FIGS. 36A and 36B are perspective views showing the manner in which the controller is turned with respect to the panel unit;

FIG. 38 is a perspective view showing how the cassette is charged;

FIGS. 39A and 39B are perspective views of cassettes, which include respective cushioning members on controllers;

FIGS. 40A and 40B are perspective views of cassettes, which include grips provided respectively on controllers and panel units;

FIGS. 42A and 42B are perspective views of cassettes, which include grips provided respectively on controllers and panel units;

FIG. 44 is a perspective view of a cassette, which includes grips provided respectively on a controller and a panel unit;

FIG. 47 is a perspective view of a cassette, which includes two grips provided on a panel unit;

FIG. 51 is a schematic view of a radiographic image capturing system incorporating therein a double-sided image capturing cassette;

FIG. 60 is a perspective view showing how the cassette shown in FIG. 52 is charged;

FIGS. 61A and 61B are perspective views of cassettes, which include grips provided on controllers;

FIG. 67 is a perspective view showing how the cassette is charged;

FIGS. 69A and 68B are perspective views showing the manner in which a controller is turned with respect to a panel unit.

DESCRIPTION OF EMBODIMENTS

Radiographic image capturing apparatus according to preferred embodiments of the present invention will be described in detail below with reference to the accompanying drawings.

1. Description of First Embodiment:

First, a radiographic image capturing apparatus according to a preferred embodiment of a first invention (first embodiment) will be described in detail below with reference to FIGS. 1 through 26.

<Description of Arrangement of the First Embodiment>

Figure 1:
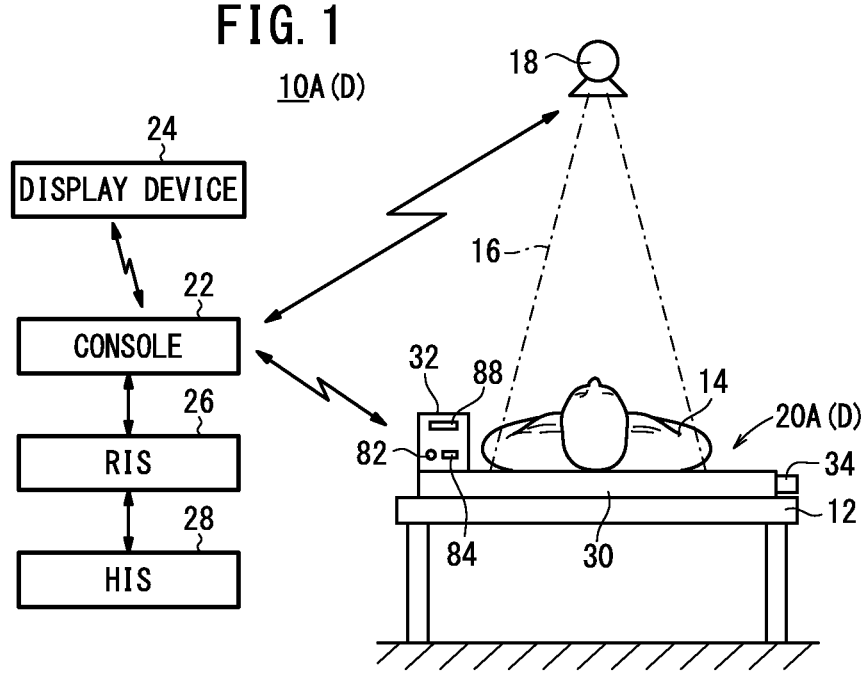
FIG. 1 is a schematic view of a radiographic image capturing system incorporating therein a cassette according to a first embodiment of the present invention.

As shown in FIG. 1, a radiographic image capturing system 10A includes a radiation source 18 for applying radiation 16, which has a dose according to image capturing conditions, to a subject 14 such as a patient lying on an image capturing base 12 such as a bed or the like, an electronic cassette 20A for detecting radiation 16 that has passed through the subject 14 and converting the detected radiation into a radiographic image, a console 22 for controlling the radiation source 18 and the electronic cassette 20A, and a display device 24 for displaying captured radiographic images.

The console 22, the radiation source 18, the electronic cassette 20A, and the display device 24 send signals to each other and receive signals from each other by way of a wireless LAN (Local Area Network) according to standards such as UWB (Ultra-Wide Band), IEEE802.11.a/g/n., or the like, or via wireless communications using milliwaves. The console 22, the radiation source 18, the electronic cassette 20A, and the display device 24 may also send signals to each other and receive signals from each other by way of wired communications using cables.

The console 22 is connected to a radiology information system (RIS) 26, which generally manages radiographic image information handled by the radiological department of a hospital, along with other information. The RIS 26 is connected to a hospital information system (HIS) 28, which generally manages medical information in the hospital.

The electronic cassette 20A, which serves as the radiographic image capturing apparatus according to the first embodiment, is a portable electronic cassette, including a panel unit 30 disposed between the image capturing base 12 and the subject 14, a controller 32 disposed on the panel unit 30, and a grip 34 disposed on a side of the panel unit 30. The panel unit 30 is thinner than the controller 32.

Figure 2:
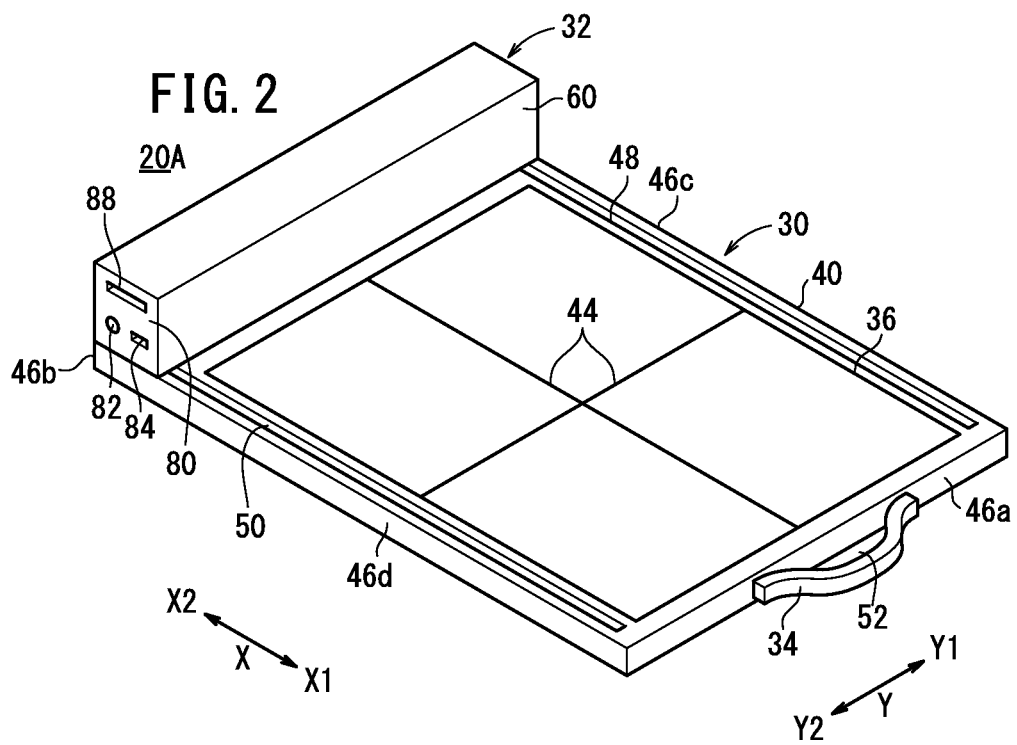
FIG. 2 is a perspective view of the cassette shown in FIG. 1.
Figure 3:
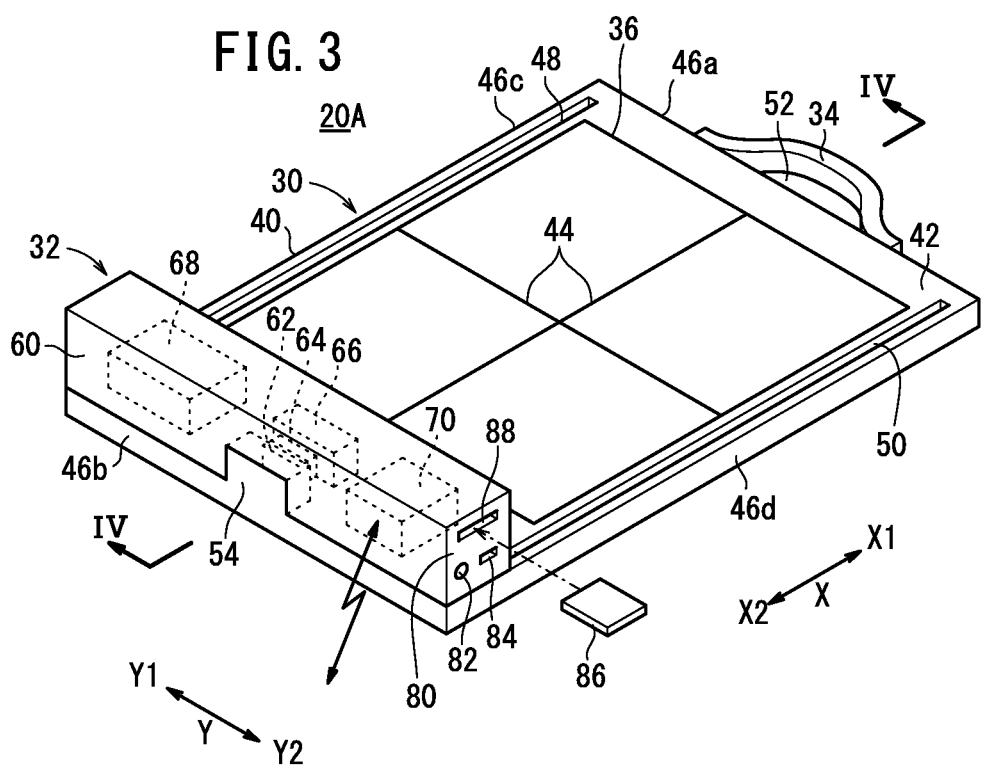
FIG. 3 is a perspective view of the cassette shown in FIG. 1.
Figure 4:
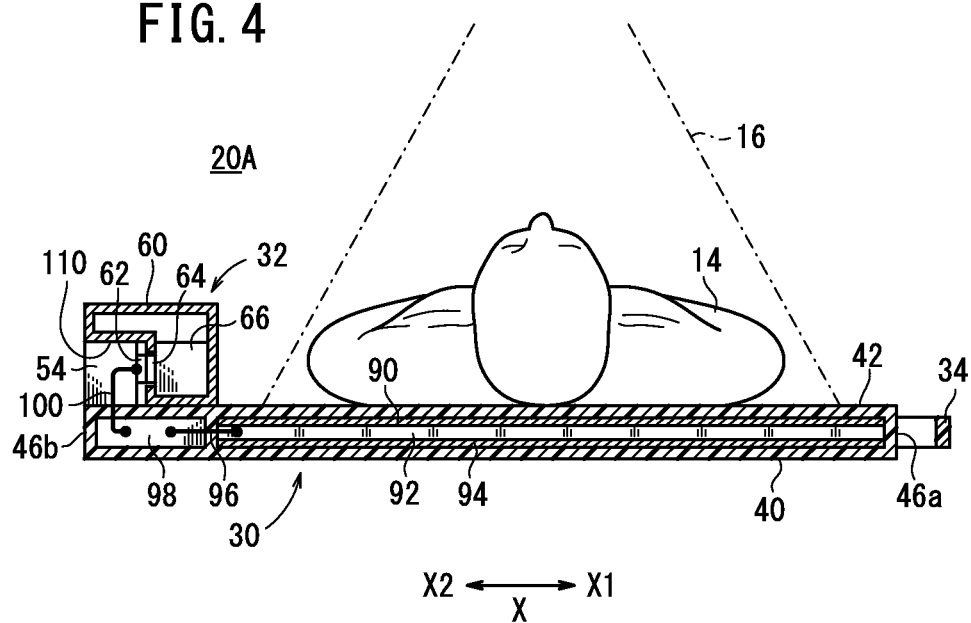
FIG. 4 is a cross-sectional view taken along line IV-IV of FIG. 3.

As shown in FIGS. 2 through 4, the panel unit 30 includes a substantially rectangular housing (first housing) 40 made of a material permeable to radiation 16. The housing 40 has an upper surface on which the subject 14 lies, and which serves as an irradiation surface 42 that is irradiated with radiation 16. The irradiation surface 42 includes guide lines 44, disposed substantially centrally thereon, indicative of an image capturing area and an image capturing position for the subject 14. The guide lines 44 include an outer frame representing an image capturing area 36 on the irradiation surface 42, which indicates an irradiation field that is irradiated with radiation 16. The guide lines 44 have a central position (where two guide lines 44 cross each other in a crisscross pattern), which defines a central position of the image capturing area 36 and a geometrically central position of the electronic cassette 20A.

The housing 40 has a guide 48 in the form of a straight recess or groove on a side surface (other side surface) 46c outside of the image capturing area 36 on the irradiation surface 42. The guide 48 extends along the directions of the arrow X (i.e., in directions parallel to side surfaces 46c, 46d). The housing 40 also has a guide 50 on a side surface (other side surface) 46d outside of the image capturing area 36. The guide 50 extends along the directions of the arrow X parallel to the guide 48. As shown in plan in FIG. 5, the straight guides 48, 50 extend parallel to each other in sandwiching relation to the image capturing area 36 formed between two side surfaces 46a, 46b (i.e., between two sides of the irradiation surface 42).

The grip 34 is disposed on the side surface (other side surface) 46a of the housing 40. The grip 34 includes a handle, which cooperates with the side surface 46a in defining a hole 52 therebetween, such that the hole 52 is large enough for the hand of a doctor or radiological technician (user) to be placed therein.

The housing 40 includes a block 54 that projects upwardly from the side surface (one side surface) 46b of the irradiation surface 42. The controller 32 is disposed on the side surface 46b of the irradiation surface 42 so as to cover the block 54 from above.

The controller 32 includes a substantially rectangular housing (second housing) 60 made of a material permeable to radiation 16. The housing 60 extends in the directions of the arrow Y (i.e., in directions parallel to the side surfaces 46a, 46b) so as to cover portions of the guides 48, 50 that lie in the direction indicated by the arrow X2 (near the side surface 46b) (see FIG. 5). The housing 60 houses therein a connector 64 for fitting engagement with another connector (connector) 62 disposed on a side surface of the block 54, which faces in the direction indicated by the arrow X1, a cassette controller (panel controller) 66 electrically connected to the connector 64, for controlling the panel unit 30 through the connectors 62, 64, a power supply 68 such as a battery or the like, and a communication unit 70 for sending signals to and receiving signals from the console 22 via a wireless communication link.

In a condition in which the connectors 62, 64 are held in fitting engagement with each other, the power supply 68 supplies electric power to the panel unit 30 through the connectors 62, 64, and also supplies electric power to the cassette controller 66 and to the communication unit 70. If the connectors 62, 64 are separated from each other, thereby electrically disconnecting the panel unit 30 and the controller 32 from each other, the power supply 68 supplies electric power only to the cassette controller 66.

The controller 32 has a side surface 80 facing in the direction indicated by the arrow Y2 (near the side surface 46d). The side surface 80 has an input terminal 82 for an AC adapter for enabling charging of the power supply 68 from an external power supply, a USB (Universal Serial Bus) terminal 84, which serves as an interface means for sending information to and receiving information from an external apparatus, and a card slot 88 for receiving a memory card 86 therein such as a PC card or the like.

Figure 5:
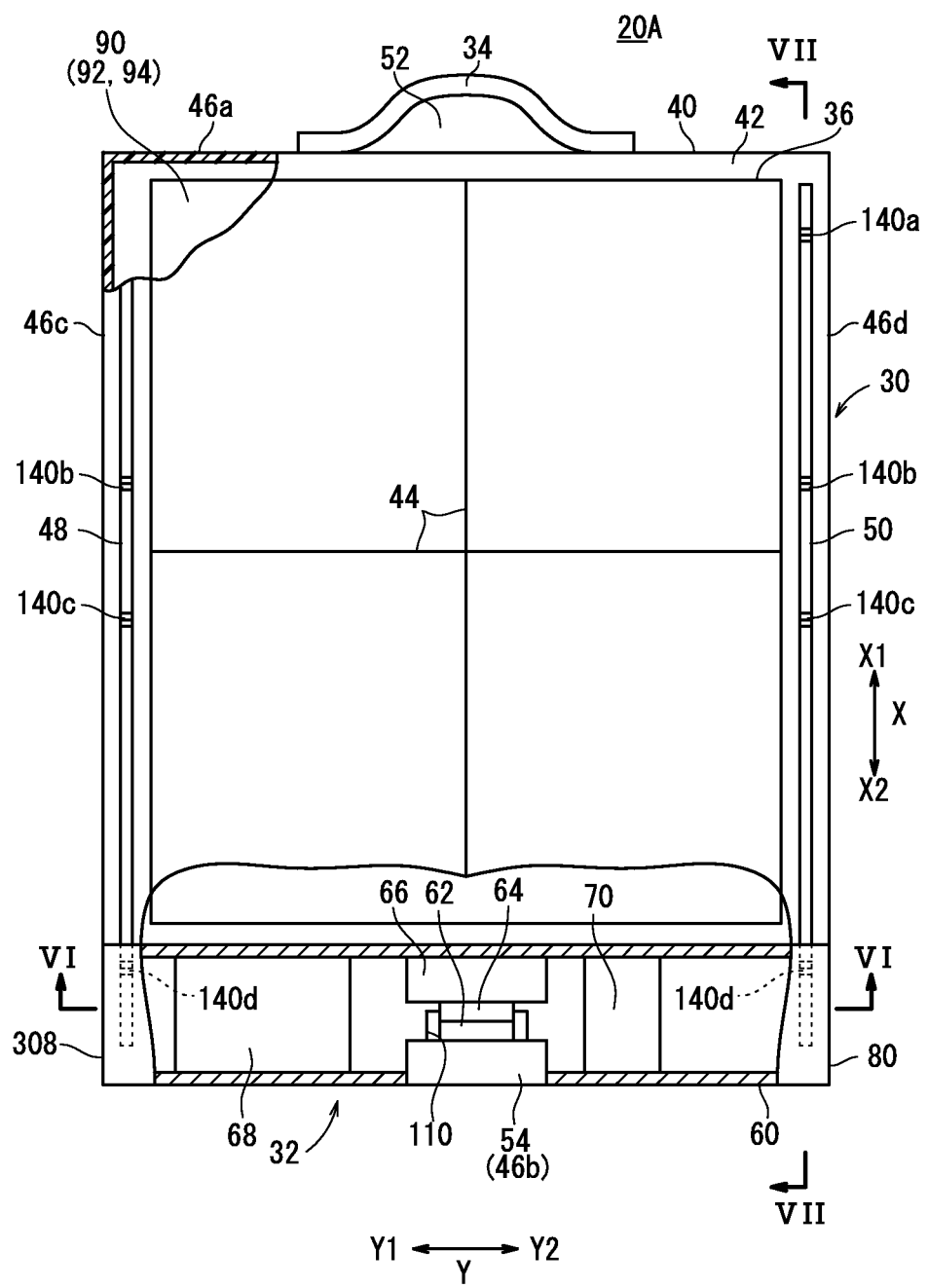
FIG. 5 is a plan view, partially cut away, of the cassette shown in FIG. 1.
Figure 6:
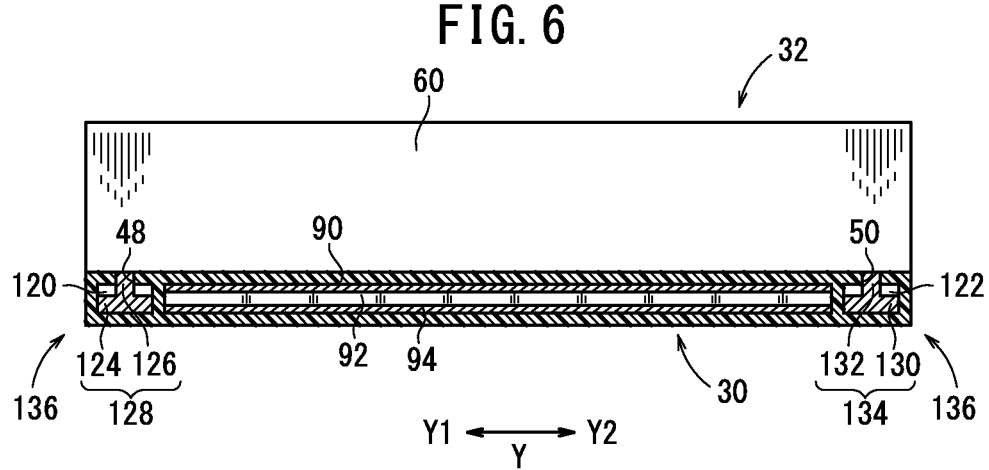
FIG. 6 is a cross-sectional view taken along line VI-VI of FIG. 5.

As shown in FIGS. 4 through 6, the panel unit 30 houses therein a grid 90 for removing scattered rays of radiation 16 from the subject 14 while the radiation source 18 irradiates the subject 14 with radiation 16, a radiation conversion panel 92 for detecting radiation 16 that has passed through the subject 14, and a lead plate 94 for absorbing back scattered rays of the radiation 16. The grid 90, the radiation conversion panel 92, and the lead plate 94 are successively arranged in this order from the irradiation surface 42, which faces toward the subject 14. The radiation conversion panel 92 and the lead plate 94 are substantially coexistent with the image capturing area 36 as viewed in plan (see FIG. 5). The irradiation surface 42 may be constructed as the grid 90.

The radiation conversion panel 92 may be an indirect-conversion-type radiation conversion panel, which employs a scintillator for converting radiation 16 that has passed through the subject 14 into visible light, and a solid-state detector (hereinafter also referred to as "pixels") made of a material such as amorphous silicon (a-Si) or the like for converting the visible light into electric signals. Alternatively, the radiation conversion panel 92 may be a direct-conversion-type radiation conversion panel, which employs a solid-state detector made of a material such as amorphous selenium (a-Se) or the like for converting the dose of radiation 16 directly into electric signals.

Indirect-conversion-type conversion panels, which convert radiation 16 that has passed through the subject 14 into visible light with a scintillator made of cesium iodide (CsI) or gadolinium oxide sulfur (GOS), and convert the visible light into electric signals with a solid-state detector (pixels), include a face-side readout radiation detector and a reverse readout radiation detector. The face-side readout radiation detector, which is of an ISS (Irradiation Side Sampling) type, includes the solid-state detector and the scintillator, which are arranged successively along the direction in which radiation 16 is applied. The reverse readout radiation detector, which is of a PSS (Penetration Side Sampling) type, includes the scintillator and the solid-state detector, which are arranged successively along the direction in which radiation 16 is applied.

In the panel unit 30, the radiation conversion panel 92 is electrically connected through a flexible board 96 to a driver circuit 98, which is electrically connected through another flexible board 100 to the connector 62.

As shown in FIG. 4, the housing 60 has a recess 110 defined in a side thereof facing in the direction of the arrow X2, and the connector 64 is disposed in the recess 110. In a state in which the block 54 engages in the recess 110 and the connectors 62, 64 are held in fitting engagement with each other, the cassette controller 66 is electrically connected to the driver circuit 98 through the connectors 64, 62 and the flexible board 100. The driver circuit 98 drives the radiation conversion panel 92 in accordance with control signals (address signals) from the cassette controller 66, and reads a radiographic image from the radiation conversion panel 92, and outputs the radiographic image to the cassette controller 66. The power supply 68 supplies electric power to the driver circuit 98 through the connectors 64, 62 and the flexible board 100, thereby enabling the driver circuit 98 to drive the radiation conversion panel 92 through the flexible board 96.

In FIG. 4, the driver circuit 98 is illustrated as being disposed in a region of the panel unit 30 that is displaced in the direction of the arrow X2. Although the panel unit 30 actually houses other driver circuits arranged along the guides 48, 50, in the description of the first embodiment, such other driver circuits are omitted from illustration for the sake of brevity.

As shown in FIG. 6, the bottoms of the guides 48, 50, which extend in the directions of the arrow X, define respective chambers 120, 122, which are wider than upper portions of the guides 48, 50 in communication with the exterior. The guide 48 includes a moving member 128 comprising a slider 124 disposed in the chamber 120, and a joint 126 coupling the slider 124 and the housing 60 through the guide 48. The guide 50 includes a moving member 134 comprising a slider 130 disposed in the chamber 122, and a joint 132 coupling the slider 130 and the housing 60 through the guide 50.

Figure 7A:
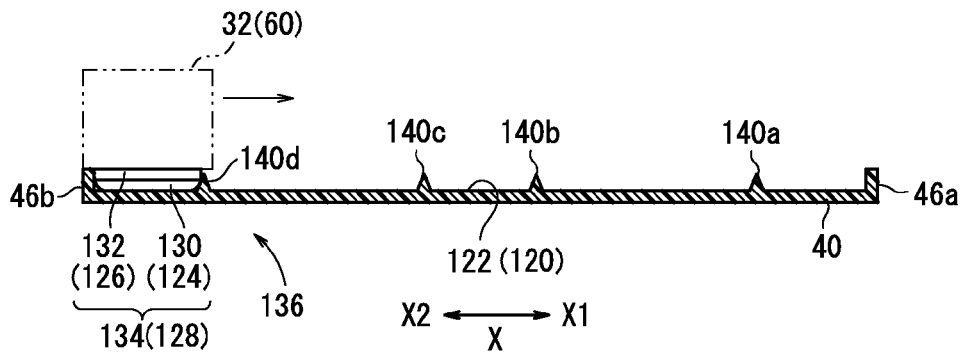
FIGS. 7A through 7C are cross-sectional views taken along line VII-VII of FIG. 5, showing the manner in which a controller is translated with respect to a panel unit.
Figure 7B:
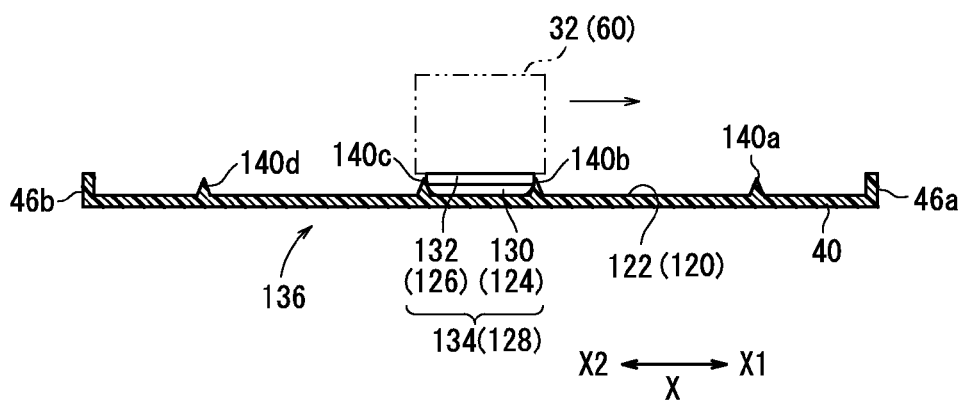
Figure 7C:
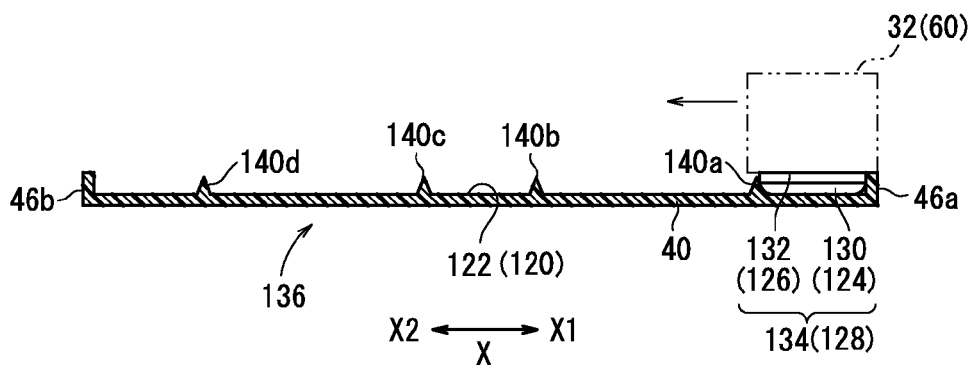

The sliders 124, 130 have respective widths along the directions of the arrow Y, which are essentially the same as the widths of the chambers 120, 122 along the directions of the arrow Y. The sliders 124, 130 have upper surfaces, which are lower than the ceilings of the chambers 120, 122. Therefore, the chambers 120, 122 include clearances that enable the sliders 124, 130 to move vertically therein. As shown in FIGS. 7A through 7C, the sliders 124, 130 and the joints 126, 132 have respective lengths along the directions of the arrow X, which are essentially the same as each other but slightly smaller than the width of the housing 60 along the directions of the arrow X. The sliders 124, 130 have round opposite ends along the directions of the arrow X.

As shown in FIGS. 5 and 7A through 7C, the bottoms of the chambers 120, 122 have a plurality of chevron-shaped ridges (stop members) 140a through 140d spaced along the directions of the arrow X. The interval between the side surface 46a and the ridge 140a, the interval between the ridge 140b and the ridge 140c, and the interval between the ridge 140d and the side surface 46b are essentially of the same length as the lengths of the sliders 124, 130 and the joints 126, 132 along the directions of the arrow X.

As described above, since the moving members 128, 134 are joined to the bottom surface of the housing 60 of the controller 32, and are disposed in the guides 48, 50 while the housing 60 is translated along the directions of the arrow X, as shown in FIGS. 7A through 8B, the moving members 128, 134 slide in unison with the housing 60 along the directions of the arrow X while being guided by the guides 48, 50. Although the ridges 140a through 140d are disposed in the chambers 120, 122 of the guides 48, 50, since clearances are defined between the upper surfaces of the sliders 124, 130 and the ceilings of the chambers 120, 122 (see FIG. 6) that enable the sliders 124, 130 to move vertically therein, even if the sliders 124, 130 abut against the ridges 140a through 140d, the sliders 124, 130 can move over the ridges 140a through 140d and along the directions of the arrow X. The moving members 128, 134 and the guides 48, 50 jointly make up moving mechanisms 136 for translating the controller 32 with respect to the panel unit 30 along the directions of the arrow X.

Figure 8A:
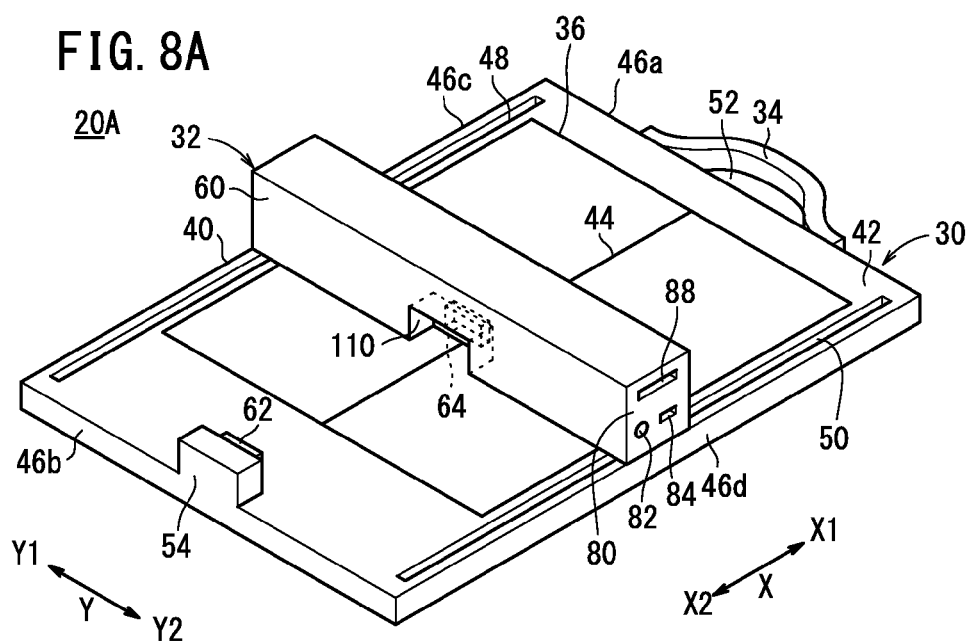
FIGS. 8A and 8B are perspective view showing the manner in which the controller is translated with respect to the panel unit.
Figure 8B:
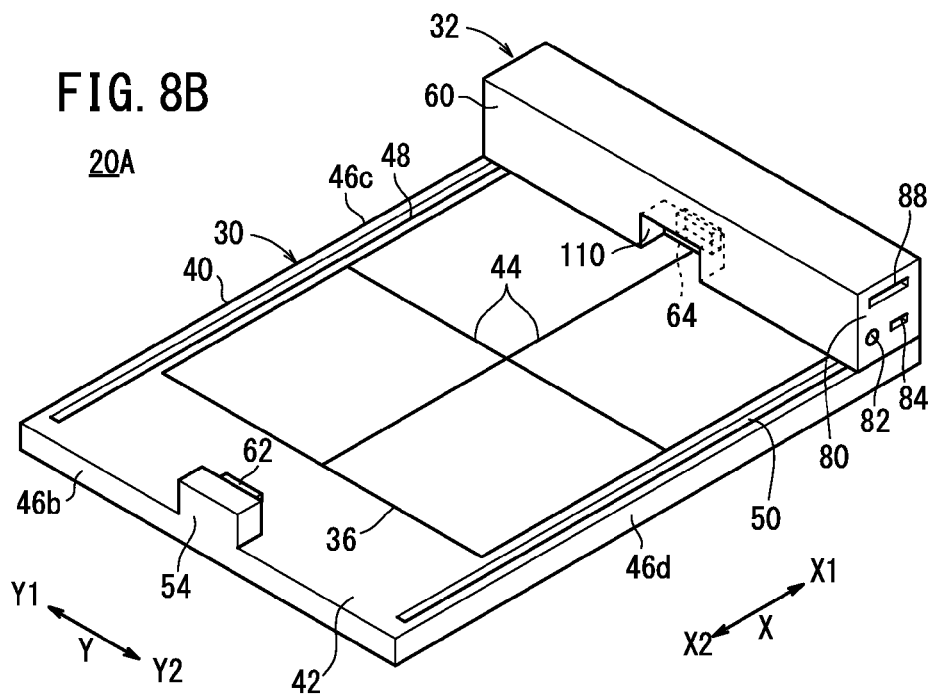

If the sliders 124, 130 are stopped between the side surface 46b and the ridge 140d, the housing 60 of the controller 32 is positioned on the side surface 46b, as shown in FIGS. 3 and 7A. If the sliders 124, 130 are stopped between the ridge 140b and the ridge 140c, the housing 60 is positioned substantially centrally in the image capturing area 36, as shown in FIGS. 7B and 8A. If the sliders 124, 130 are stopped between the ridge 140a and the side surface 46a, the housing 60 is positioned on the side surface 46a and the grip 34, as shown in FIGS. 7C and 8B.

With the housing 60 being positioned as shown in FIGS. 3 and 7A, the connectors 62, 64 are held in fitting engagement with each other. With the housing 60 being positioned as shown in FIGS. 7B and 8A or as shown in FIGS. 7C and 8B, the connectors 62, 64 are brought out of fitting engagement with each other, thereby electrically disconnecting the controller 32 and the panel unit 30 from each other.

FIGS. 9A through 9C illustrate the manner in which a user 142, such as a doctor or radiological technician, carries the electronic cassette 20A.

As shown in FIG. 9A, the user 142 grips the grip 34 and carries the electronic cassette 20A with the controller 32 positioned on the side surface 46b (see FIG. 3), and with the controller 32 in a lowermost position and the grip 34 in an uppermost position.

Among the components of the electronic cassette 20A, the power supply 68 (see FIGS. 3 and 5) is relatively heavy, such that the ratio of the weight of the controller 32 to the overall weight of the electronic cassette 20A is large. In the controller 32, the cassette controller 66, the power supply 68, and the communication unit 70 are located centrally in a central region of the housing 60. In FIG. 9A, the electronic cassette 20A is illustrated in an eccentric state, in which the geometrically central position of the electronic cassette 20A (the central position of the image capturing area 36) and the center of gravity of the electronic cassette 20A (the position near the controller 32) do not coincide with each other, thereby making the entire electronic cassette 20A unbalanced in terms of the weight distribution thereof.

However, as shown in FIG. 9A, the user 142 carries the electronic cassette 20A with the controller 32 in a lowermost position, so as to lower the center of gravity of the electronic cassette 20A. Therefore, despite the unbalanced weight distribution, the user 142 can carry the electronic cassette 20A in a stable manner.

As shown in FIG. 9B, the user 142 grips the grip 34 and carries the electronic cassette 20A while the controller 32 is disposed substantially centrally in the image capturing area 36, and the grip 34 is located in an uppermost position. Since the geometrically central position of the electronic cassette 20A and the center of gravity of the electronic cassette 20A coincide substantially with each other, an eccentric state is eliminated, thereby making the entire electronic cassette 20A balanced in terms of the weight distribution thereof. As a result, the user 142 can carry the electronic cassette 20A in a stable manner.

As shown in FIG. 9C, the user 142 grips the grip 34 and carries the electronic cassette 20A while the controller 32 is disposed on the side surface 46a, and the controller 32 and the grip 34 are located in an uppermost position.

In this case, the electronic cassette 20A also is in an eccentric state in which the geometrically central position of the electronic cassette 20A and the center of gravity of the electronic cassette 20A do not coincide with each other, thereby making the entire electronic cassette 20A unbalanced in terms of the weight distribution thereof. However, inasmuch as the center of gravity of the electronic cassette 20A is in an upper position, the user 142 can grip the heavy controller 32 through the grip 34 and can carry the electronic cassette 20A in a stable manner.

According to the first embodiment, as shown in FIGS. 3 and 7A through 8B, since the housing 60 can be positioned on the side surface 46b, substantially centrally within the image capturing area 36, and at the grip 34 and the side surface 46a, the user 142 can reliably carry the electronic cassette 20A if the controller 32 is disposed with respect to the panel unit 30 in any of the positions shown in FIGS. 9A through 9C.

Figure 10:
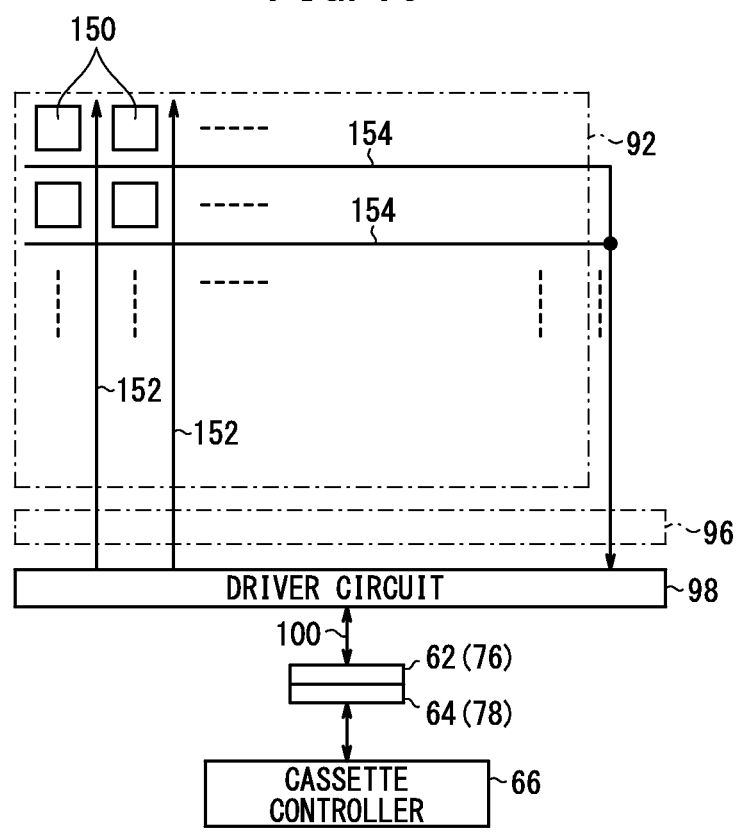
FIG. 10 is a diagram schematically showing an array of pixels in a radiation conversion panel, and electric connections between the pixels and a cassette controller.

As shown schematically in FIG. 10, the radiation conversion panel 92 includes a number of pixels 150 arrayed on a substrate (not shown), a number of gate lines 152 arrayed on the substrate for supplying control signals to the pixels 150 from the driver circuit 98 through the flexible board 96, and a number of signal lines 154 arrayed on the substrate for reading electric signals output from the pixels 150, and outputting the electric signals to the driver circuit 98 through the flexible board 96.

Figure 11:
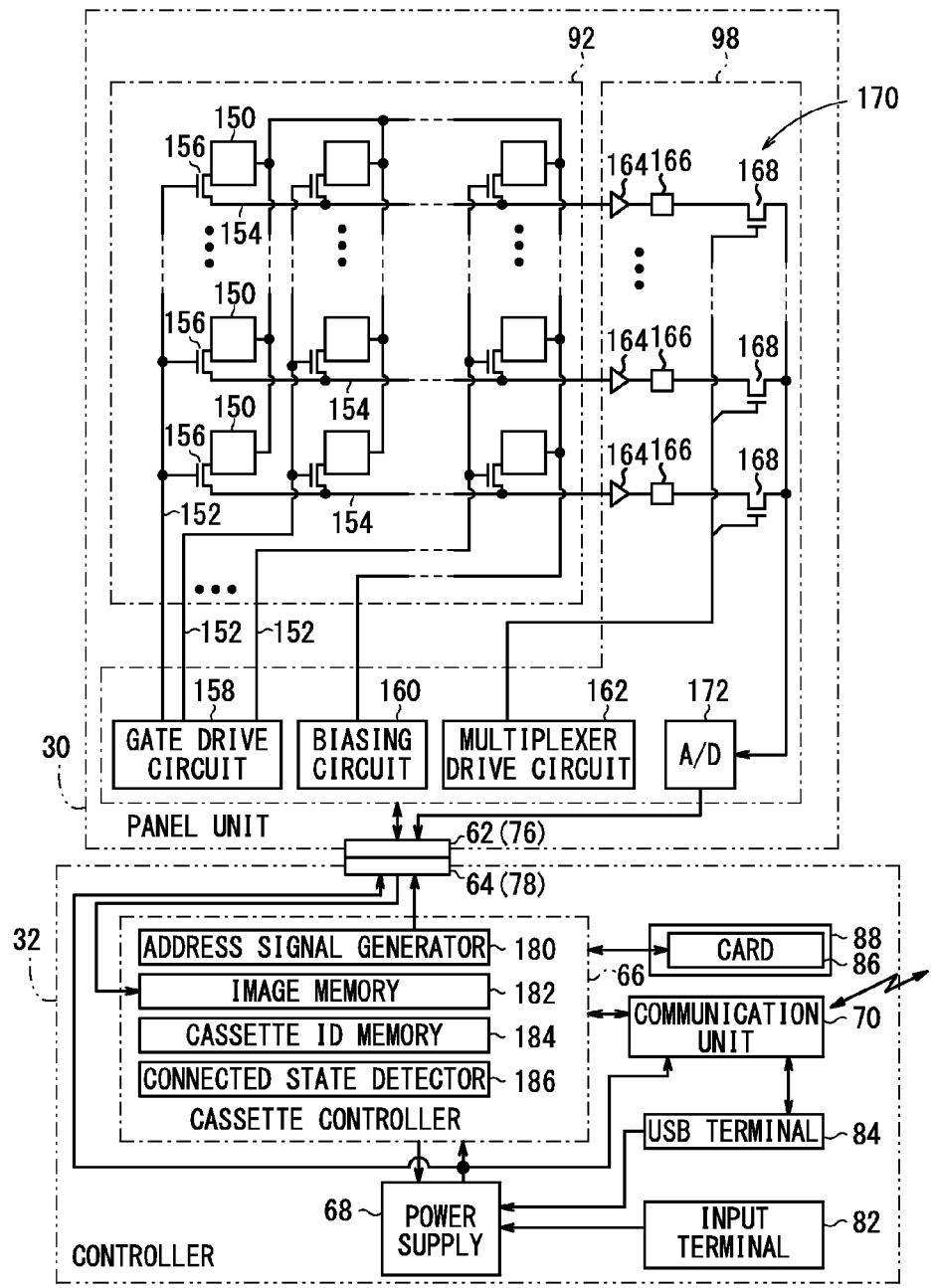
FIG. 11 is a block diagram of the cassette shown in FIG. 1.

A circuit and block arrangement of the electronic cassette 20A, which incorporates an indirect-conversion-type radiation conversion panel 92, will be described in detail below with reference to FIG. 11.

The radiation conversion panel 92 comprises an array of TFTs 156 arranged in rows and columns, and a photoelectric conversion layer including the pixels 150 made of a material such as a-Si or the like for converting visible light into electric signals, the photoelectric conversion layer being disposed on the array of TFTs 156. The pixels 150, which are supplied with a bias voltage from a biasing circuit 160 of the driver circuit 98, store electric charges generated in a case where visible light is converted into electric signals (analog signals). The electric charges can be read as image signals if the TFTs 156 are successively turned on along each of the columns.

Gate lines 152 are connected to the TFTs 156, which are connected respectively to the pixels 150. The gate lines 152 extend parallel to the columns, and signal lines 154 extend parallel to the rows. The gate lines 152 are connected to a gate drive circuit 158, and the signal lines 154 are connected to a multiplexer 170. The gate lines 152 are supplied with control signals from the gate drive circuit 158 for turning on and off the TFTs 156 arranged along the columns. The gate drive circuit 158 is supplied with address signals from the cassette controller 66.

Electric charges held by the pixels 150 flow into the signal lines 154 through the TFTs 156 arranged along the rows. The electric charges are amplified by amplifiers 164, which are connected through sample and hold circuits 166 to the multiplexer 170. The multiplexer 170 includes FET (Field Effect Transistor) switches 168 for switching between the signal lines 154, and a multiplexer drive circuit 162 for outputting selection signals to select one of the FET switches 168 at a time. The multiplexer drive circuit 162 is supplied with address signals from the cassette controller 66. The FET switches 168 are connected to an A/D converter 172, which supplies digital signals representing a radiographic image to the cassette controller 66.

The TFTs 156, which function as switching elements, may be combined with any of various other image capturing devices such as a CMOS (Complementary Metal-Oxide Semiconductor) image sensor, or may be replaced with a CCD (Charge-Coupled Device) image sensor in which electric charges are shifted and transferred by shift pulses that correspond to gate signals used in the TFTs 156.

The cassette controller 66 includes an address signal generator 180, an image memory 182, a cassette ID memory 184, and a connected state detector (connection detector) 186.

The address signal generator 180 supplies address signals to the gate drive circuit 158 and the multiplexer drive circuit 162. The image memory 182 stores the radiographic image detected by the radiation conversion panel 92. The cassette ID memory 184 stores cassette information for identifying the electronic cassette 20A. The connected state detector 186 detects whether or not the connectors 62, 64 are electrically connected to each other, and based on the detection result, controls supply of electric power from the power supply 68 to various components in the electronic cassette 20A.

<Description of Operations of the First Embodiment>

The radiographic image capturing system 10A, which incorporates the electronic cassette 20A according to the first embodiment, basically is constructed as described above. Operations of the radiographic image capturing system 10A will be described below with reference to the flowchart shown in FIG. 12.

According to the sequence described below, after the electronic cassette 20A shown in FIG. 9B has been carried to the image capturing base 12, the electronic cassette 20A is placed in the state shown in FIG. 1 and captures a radiographic image of the subject 14, after which the electronic cassette 20A is restored to the state shown in FIG. 9B and carried.

In step S1 shown in FIG. 12, the user 142, who may be a doctor or radiological technician, grips the grip 34 with the grip 34 being in an uppermost position and the controller 32 being located substantially centrally in the image capturing area 36 (see FIG. 9B). The user carries the electronic cassette 20A from a given storage location in the radiological department of the hospital to the image capturing base 12 (see FIG. 1). Since the connector 62 and the connector 64 are not held in fitting engagement with each other, the connected state detector 186 (see FIG. 11) detects that the connector 62 and the connector 64 are electrically disconnected from each other, and controls the power supply 68 to supply electric power only to the cassette controller 66. The electronic cassette 20A is thus placed in a sleep mode with only the cassette controller 66 operating.

In step S2, the user 142 places the electronic cassette 20A on the image capturing base 12, with the controller 32 and the irradiation surface 42 facing upwardly. Thereafter, the user 142 translates the housing 60 of the controller 32 from the substantially central position in the image capturing area 36 (see FIGS. 7B and 8A) to the position on the side surface 46b (see FIGS. 1 through 5 and 7A).

Upon the user 142 pushing the housing 60 of the controller 32 in the direction of the arrow X2, the moving members 128, 134, which are coupled to the controller 32, slide (are translated) in unison with the housing 60 in the direction of the arrow X2 while being guided by the guides 48, 50. Ends of the sliders 124, 130, which face in the direction of the arrow X2, abut against the ridges 140c, respectively. Since clearances are defined between upper surfaces of the sliders 124, 130 and the ceilings of the chambers 120, 122 of the guides 48, 50 (see FIG. 6), the sliders 124, 130 move over the ridges 140c and slide in the direction of the arrow X2.

Upon the user 142 further pushing the housing 60 in the direction of the arrow X2, the moving members 128, 134 slide in unison with the housing 60 in the direction of the arrow X2. Even if the sliders 124, 130 abut respectively against the ridges 140d, the sliders 124, 130 move over the ridges 140d and slide in the direction of the arrow X2.

The ends of the sliders 124, 130, which face in the direction of the arrow X2, abut against the side surface 46b, whereupon the sliders 124, 130 are positioned between the side surface 46b and the ridge 140d. In other words, the housing 60 of the controller 32, which is coupled to the moving members 128, 134, is positioned on the side surface 46b, and the connector 62 of the block 54 and the connector 64 in the recess 110 are held in fitting engagement with each other.

At the time that the connected state detector 186 detects that the connector 62 and the connector 64 are electrically connected to each other based on fitting engagement between the connector 62 and the connector 64, the connected state detector 186 controls the power supply 68 to supply electric power to the communication unit 70 and the panel unit 30, in addition to the cassette controller 66. The power supply 68 begins supplying electric power to the communication unit 70 and the panel unit 30. At this time, the communication unit 70 is capable of sending signals to and receiving signals from the console 22 via a wireless communication link. Upon being supplied with electric power from the power supply 68, the driver circuit 98 of the panel unit 30 becomes activated. The biasing circuit 160 supplies a bias voltage to the pixels 150, thus enabling the pixels 150 to store electric charges therein. As a result, the electronic cassette 20A changes from a sleep mode into an active mode.

In step S3, the user 142 performs a preparatory action to capture a radiographic image of a region to be imaged of the subject 14.

More specifically, the user 142 operates the console 22 to register image capturing conditions (e.g., a tube voltage and a tube current of the radiation source 18, an exposure time of the radiation 16, etc.) concerning subject information of the subject 14 to be imaged. If a region to be imaged and an imaging method are determined in advance, then the user 142 may also register such image capturing conditions.

Then, the user 142 adjusts the imaging distance between the radiation source 18 and the radiation conversion panel 92 to an SID (source-to-image distance). The user 142 places the subject 14 on the irradiation surface 42, and positions the subject 14 such that the region to be imaged of the subject 14 enters within the image capturing area 36, such that the central position of the region to be imaged is substantially aligned with the central position of the image capturing area 36.

In step S4, after the preparatory process has been performed, the user 142 presses an exposure switch (not shown) located on the console 22 or on the radiation source 18. If the exposure switch is located on the console 22, then after the exposure switch is pressed, the console 22 sends image capturing conditions to the radiation source 18 via a wireless communication link. If the exposure switch is located on the radiation source 18, then after the exposure switch is pressed, the radiation source 18 requests the console 22 to send the image capturing conditions via a wireless communication link, whereupon the console 22 sends the image capturing conditions to the radiation source 18 via the wireless communication link in response to the request from the radiation source 18.

Upon receiving the image capturing conditions, the radiation source 18 applies a prescribed dose of radiation 16 to the subject 14 for a preset period of time according to the image capturing conditions. Radiation 16 passes through the subject 14 to the radiation conversion panel 92 in the panel unit 30.

In step S5, if the radiation conversion panel 92 is an indirect-conversion-type radiation conversion panel, then the scintillator emits visible light having an intensity depending on the intensity of the radiation 16. The pixels 150 of the photoelectric conversion layer convert the visible light into electric signals, and store the electric signals as electric charges. Electric charges stored in the pixels 150, which represent a radiographic image of the subject 14, are read from the pixels 150 according to address signals, which are supplied from the address signal generator 180 of the cassette controller 66 to the gate drive circuit 158 and the multiplexer drive circuit 162.

More specifically, the gate drive circuit 158 supplies control signals to gates of the TFTs 156 connected to the gate lines 152, which correspond to the address signals supplied from the address signal generator 180. The multiplexer drive circuit 162 outputs selection signals according to address signals supplied from the address signal generator 180 in order to successively switch between (successively turn on and off) the FET switches 168 and to successively read, through the signal lines 154, the radiographic image as electric charges stored in the pixels 150, which are connected to the gate lines 152 selected by the gate drive circuit 158.

The radiographic image read from the pixels 150 connected to the selected gate lines 152 is amplified by the amplifiers 164, sampled by the sample and hold circuits 166, and supplied through the FET switches 168 to the A/D converter 172, which converts the radiographic image into digital signals. The radiographic image, which is converted into digital signals, is stored in the image memory 182 of the cassette controller 66 (step S6).

Similarly, the gate drive circuit 158 successively switches between the gate lines 152 that output control signals according to address signals supplied from the address signal generator 180, reads the radiographic image as electric charges stored in the pixels 150 connected to the gate lines 152, and stores the radiographic image in the image memory 182 of the cassette controller 66 through the FET switches 168 and the A/D converter 172 (step S6).

The radiographic image, which is stored in the image memory 182, is sent together with the cassette ID information stored in the cassette ID memory 184 through the communication unit 70 to the console 22 via a wireless communication link. The console 22 performs a prescribed image processing routine on the received radiographic image, and sends the processed radiographic image to the display device 24 via a wireless communication link. The display device 24 then displays the received radiographic image (step S7).

The user 142 views the radiographic image displayed on the display device 24 and confirms that the radiographic image of the subject 14 has appropriately been obtained. In step S8, after the image capturing process on the subject 14 has been completed, the user 142 translates the housing 60 of the controller 32 from its present position on the side surface 46b (see FIGS. 1 through 5 and 7A) to a position located substantially centrally within the image capturing area 36 (see FIGS. 7B and 8A).

More specifically, the user 142 pushes the housing 60 in the direction of the arrow X1 in order to slide (translate) the moving members 128, 134 coupled to the controller 32 in unison with the housing 60 in the direction of the arrow X1 while the moving members 128, 134 are guided by the guides 48, 50.

At this time, the ends of the sliders 124, 130, which face in the direction of the arrow X1, abut respectively against the ridges 140d. However, due to the clearance between the upper surfaces of the sliders 124, 130 and the ceilings of the chambers 120, 122 of the guides 48, 50, the sliders 124, 130 move over the ridges 140d and are translated in the direction of the arrow X1.

While the housing 60 is translated in the direction of the arrow X1, the recess 110 is spaced from the block 54, and the connector 62 and the connector 64 are brought out of fitting engagement with each other, whereby the connectors 62, 64 become electrically disconnected from each other.

Upon the connected state detector 186 detecting that the connector 62 and the connector 64 are electrically disconnected from each other, the connected state detector 186 controls the power supply 68 in order to supply electric power only to the cassette controller 66. The power supply 68 immediately stops supplying electric power to the communication unit 70 and the panel unit 30, and supplies electric power only to the cassette controller 66. As a result, the electronic cassette 20A changes from the active mode into the sleep mode in which only the cassette controller 66 is operable.

Then, the user 142 pushes the housing 60 further in the direction of the arrow X1. The moving members 128, 134 are translated in unison with the housing 60 in the direction of the arrow X1. The sliders 124, 130 abut against and move over the ridges 140c, and are further translated in the direction of the arrow X1.

The ends of the sliders 124, 130, which face in the direction of the arrow X1, abut against the ridges 140b, whereupon the moving members 128, 134 become positioned between the ridges 140c and the ridges 140b. The housing 60 of the controller 32, which is coupled to the moving members 128, 134, is positioned substantially centrally within the image capturing area 36.

In step S9, the user 142 grips the grip 34 with the grip 34 being located in the uppermost position, and the controller 32 being positioned substantially centrally in the image capturing area 36. The user carries the electronic cassette 20A to a given storage location in the radiological department of the hospital.

In steps S1 and S9 shown in FIG. 12, if the user 142 carries the electronic cassette 20A as shown in FIG. 9C, then in step S2, the user 142 may translate the controller 32 from the grip 34 and the side surface 46a to the side surface 46b, and in step S8, the user 142 may translate the controller 32 from the side surface 46b to the grip 34 and the side surface 46a. In steps S1 and S9 shown in FIG. 12, if the user 142 carries the electronic cassette 20A as shown in FIG. 9A, then the operations performed in steps S2 and S8 are dispensed with.

<Description of Advantages of the First Embodiment>

As described above, the center of gravity of the electronic cassette 20A according to the first embodiment can be changed easily by translating the controller 32, which is responsible for unbalanced weight distribution, with respect to the panel unit 30 along the directions of the arrow X, using the moving mechanisms 136, which include the guides 48, 50 and the moving members 128, 134.

More specifically, since the ratio of the weight of the controller 32 to the overall weight of the electronic cassette 20A is relatively large, if the controller 32 is displaced with respect to the geometrically central position of the electronic cassette 20A (a substantially central position of the image capturing area 36), then the electronic cassette 20A is in an eccentric state in which the center of gravity thereof does not coincide with the above central position, thereby making the entire electronic cassette 20A unbalanced in terms of the weight distribution thereof.

According to the first embodiment, the controller 32 is translated with respect to the panel unit 30 along the directions of the arrow X, so as to bring the central position and the center of gravity into substantial agreement with each other, thereby easily eliminating the unbalanced weight distribution.

More specifically, after the controller 32 is translated with respect to the panel unit 30 to a substantially central position within the image capturing area 36 shown in FIGS. 7B and 8A using the guides 48, 50 and the moving members 128, 134, the user 142 carries the electronic cassette 20A with the grip 34 in an uppermost position, as shown in FIG. 9B.

Inasmuch as the electronic cassette 20A feels lightweight when the user 142 carries the electronic cassette 20A, the user 142 finds it easy to carry the electronic cassette 20A in a stable manner. As a result, the user 142 can carry the electronic cassette 20A without dropping the electronic cassette 20A or causing the controller 32 to hit other objects, and the user experiences a reduced burden upon carrying the electronic cassette 20A.

According to the first embodiment, as described above, since any unbalanced weight distribution of the electronic cassette 20A is easily eliminated by translating the controller 32 with respect to the panel unit 30 using the moving mechanisms 136, the user 142 can carry the electronic cassette 20A in a stable manner.

Since the moving members 128, 134 and the controller 32 are linearly translated in unison with each other along the guides 48, 50 in the directions of the arrow X, the controller 32 is translated with respect to the panel unit 30 by a simple mechanism. Even though the controller 32 may be disposed over the image capturing area 36 while the electronic cassette 20A is being carried, the controller 32 can be retracted away from the image capturing area 36 in the image capturing process. Therefore, the controller 32 and the guides 48, 50 do not present an obstacle to capturing of radiographic images.

The guides 48, 50 extend along the directions of the arrow X (the longitudinal direction of the housing 40), which is substantially perpendicular to two sides (two side surfaces 46a, 46b) of the irradiation surface 42. Consequently, in the case that the moving members 128, 134 and the controller 32 are linearly translated in unison with each other, the central position and the aforementioned center of gravity can easily be made to coincide with each other, thereby reliably eliminating any unbalanced weight distribution.

Since the two guides 48, 50 are disposed so as to keep the image capturing area 36 sandwiched between the opposite two sides (side surfaces 46a, 46b) of the irradiation surface 42, the two moving members 128, 134 are mounted on the controller 32 while being disposed in the two guides 48, 50. As a result, the controller 32 and the two moving members 128, 134 can be translated more stably and reliably along the two guides 48, 50.

The guides 48, 50 are in the form of recesses or grooves, which are defined substantially linearly in the irradiation surface 42 of the housing 40. The moving members 128, 134 are slidable linearly along such recesses or grooves. Therefore, the controller 32 can be translated simply and reliably with respect to the panel unit 30.

The ridges 140a through 140d, which serve to stop sliding movement of the moving members 128, 134, are disposed in the chambers 120, 122 of the guides 48, 50 in the form of recesses or grooves. Accordingly, the controller 32 can be stopped reliably at any desired position with respect to the panel unit 30.

Inasmuch as the side surface 46a of the panel unit 30 has the grip 34, which can be gripped by the user 142 to carry the electronic cassette 20A, the user 142 finds it easy to carry the electronic cassette 20A.

During times that the controller 32 is translated, the power supply 68 stops supplying electric power to the communication unit 70 and the panel unit 30. Therefore, wasteful electric power consumption is minimized.

More specifically, during translation of the controller 32, the connector 62 and the connector 64 are brought out of fitting engagement with each other, thereby electrically disconnecting the panel unit 30 and the controller 32 from each other. At this time, in order to minimize wasteful electric power consumption, the power supply 68 stops supplying electric power to the communication unit 70 and the panel unit 30.

The cassette controller 66 includes the connected state detector 186, which detects whether or not the connectors 62, 64 are electrically connected to each other. As the connected state detector 186 detects whether or not the connectors 62, 64 are electrically connected to each other, the timing to control the panel unit 30 and the timing to read radiographic images from the radiation conversion panel 92 can easily be grasped. The connected state detector 186 indicates the detection result to the power supply 68, so as to enable the power supply 68 to supply electric power efficiently.

The thickness of the panel unit 30 is less than the thickness of the controller 32, thereby making the electronic cassette 20A both thin and lightweight.

According to the first embodiment, as described above, since the controller 32 can be translated with respect to the panel unit 30 along the directions of the arrow X, after the controller 32 has been moved to the position shown in FIGS. 3 and 7A with respect to the panel unit 30 using the moving mechanisms 136, which include the guides 48, 50 and the moving members 128, 134, the user 142 can carry the electronic cassette 20A with the grip 34 located in an uppermost position, and with the controller 32 located in a lowermost position, as shown in FIG. 9A.

Even though the electronic cassette 20A has an unbalanced weight distribution, since the user 142 carries the electronic cassette 20A with the center of gravity kept low, the user 142 can carry the electronic cassette 20A in a stable manner.

More specifically, since the user 142 grips the grip 34 with the overall center of gravity of the electronic cassette 20A kept low, the electronic cassette 20A feels light to the user 142 upon carrying the same. Therefore, the user 142 can carry the electronic cassette 20A easily and in a stable manner. Consequently, as shown in FIG. 9A, the user 142 can carry the electronic cassette 20A without dropping the electronic cassette 20A or causing the controller 32 to hit other objects, and thus, the user experiences a reduced burden upon carrying the electronic cassette 20A.

According to the first embodiment, after the controller 32 has been moved to the position shown in FIGS. 7C and 8B with respect to the panel unit 30, the user can carry the electronic cassette 20A with the grip 34 and the controller 32 in an uppermost position, as shown in FIG. 9C.

Even though the electronic cassette 20A has an unbalanced weight distribution, since the user 142 grips the heavy controller 32 through the grip 34, the user 142 can carry the electronic cassette 20A in a stable manner.

More specifically, since the user grips the heavy controller 32 through the grip 34, the electronic cassette 20A feels light to the user 142 upon carrying the same, and thus the user 142 finds it easy to carry the electronic cassette 20A in a stable manner. As a result, in FIG. 9C, the user 142 can carry the electronic cassette 20A without dropping the electronic cassette 20A or causing the controller 32 to hit other objects, and thus, the user experiences a reduced burden upon carrying the electronic cassette 20A.

According to the first embodiment, it has been described that the housing 60 of the controller 32, which is thicker than the housing 40 of the panel unit 30, is disposed on the housing 40. However, the first embodiment is not limited to this description, and the controller 32 may be disposed so as to protrude from the housing 40, insofar as the controller 32 can still be translated with respect to the panel unit 30.

In the above description, the controller 32 is disposed at a location outside of the image capturing area 36 of the panel unit 30 at least during the image capturing process. However, the first embodiment is not limited to the above description, and the controller 32 may be disposed at a location outside of an area of the panel unit 30 that is irradiated with radiation 16 having passed through the subject 14. For example, if radiation 16 is applied to a small area within the image capturing area 36, then the controller 32 may be disposed at a location within the image capturing area 36 that is not irradiated with radiation 16. In such a case, the console 22 trims a portion of the radiographic image acquired from the electronic cassette 20A, which corresponds to the area irradiated with radiation 16, thereby obtaining a desired image that corresponds to the small area.

<Description of Modifications of the First Embodiment>

The electronic cassette 20A according to the first embodiment is not limited to the above description, but may be implemented according to the embodiments shown in FIGS. 13 through 26.

FIG. 13 is a perspective view showing a process of charging the power supply 68 using a cradle 190, which is disposed in a necessary location in a medical organization.

The electronic cassette 20A and the cradle 190 are electrically connected to each other through a USB cable 192 having connectors 194, 196.

The cradle 190 may be used not only for charging the power supply 68, but also to send required information to and receive required information from the console 22 and the RIS 26 in the medical organization, using a wireless communication or a wired communication function of the cradle 190. Information that is sent and received includes radiographic images recorded in the image memory 182 of the electronic cassette 20A.

The cradle 190 has a display unit 198, which may display the charged state of the electronic cassette 20A together with other necessary information including radiographic images acquired from the electronic cassette 20A.

A plurality of cradles 190 may be connected to a network. Charged states of electronic cassettes 20A connected to the respective cradles 190 may be collected through the network, whereby locations of electronic cassettes 20A, which have been charged to an operational state, can be confirmed.

Figure 14A:
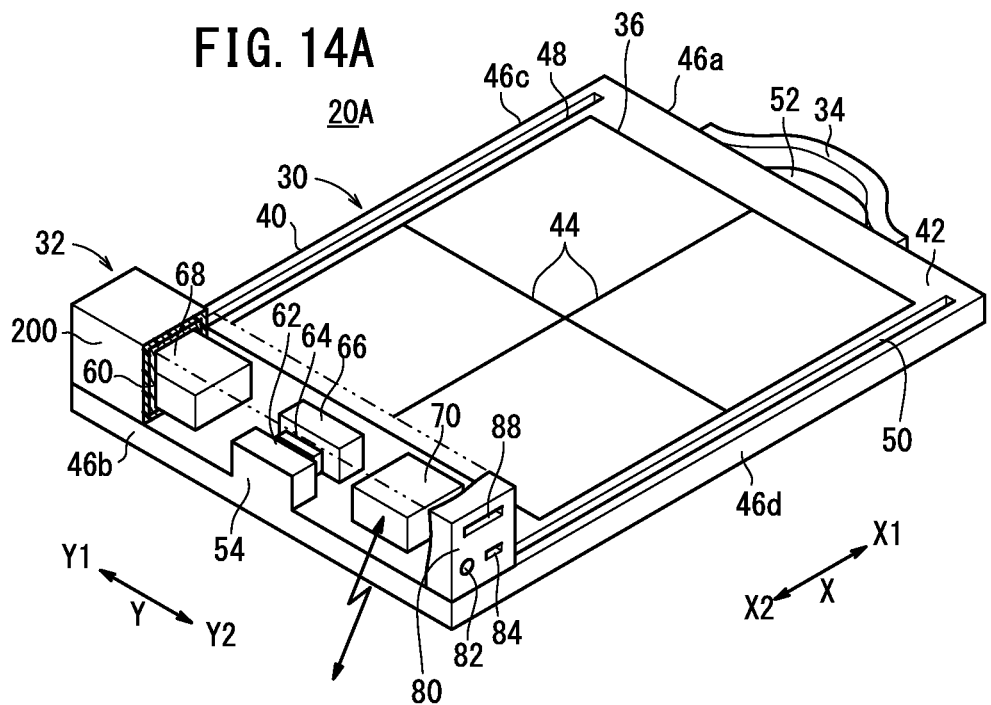
FIGS. 14A and 14B are perspective views of cassettes, which include respective cushioning members provided on controllers.
Figure 14B:
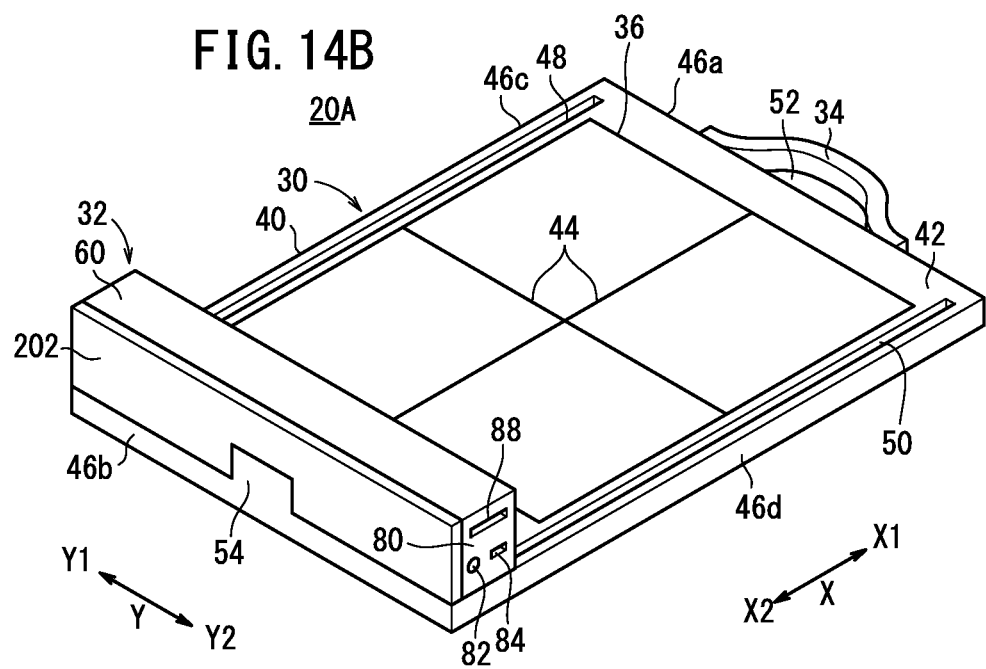

FIG. 14A shows the housing 60 of the controller 32, which is covered entirely with a cushioning member 200. FIG. 14B shows the housing 60, a side surface 46*b* of which is covered with a cushioning member 202.

If the user 142 carries the electronic cassette 20A with the controller 32 disposed on the side surface 46*b* with respect to the panel unit 30, the controller 32 is disposed in a lowermost position on the electronic cassette 20A, as shown in FIG. 9A. The housing 60 of the controller 32 is covered entirely with the cushioning member 200, or partially by means of the cushioning member 202, whereby the controller 32 is effectively protected from impacts that may occur if the controller 32 hits other objects, or if the electronic cassette 20A is dropped.

Figure 15A:
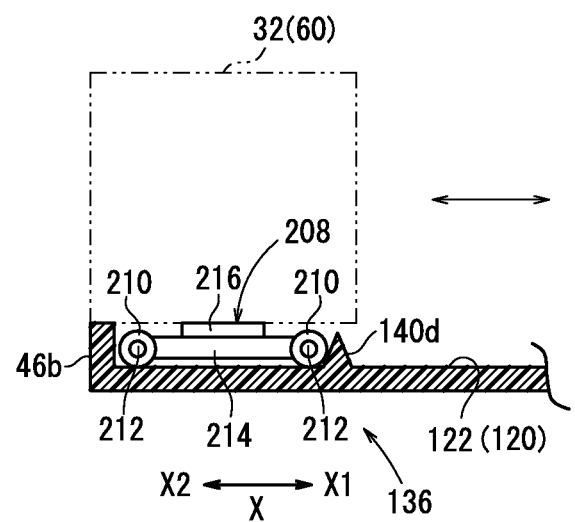
FIGS. 15A and 15B are cross-sectional views showing the manner in which a controller is translated by wheels with respect to a panel unit.
Figure 15B:
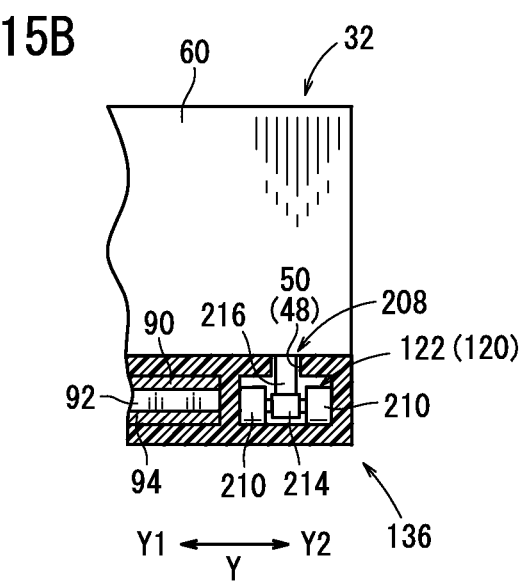
Figure 16:
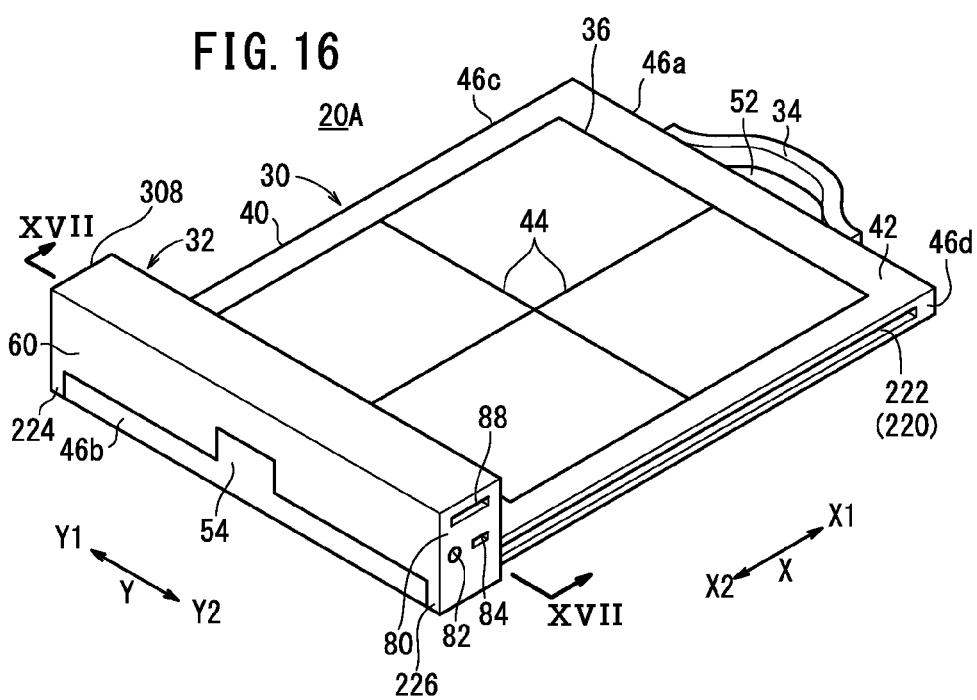
FIG. 16 is a perspective view of a cassette having a guide on a side surface of a panel unit.
Figure 18A:
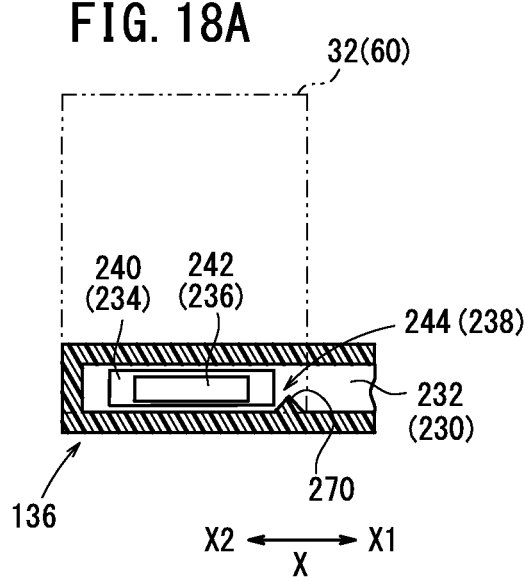
FIGS. 18A and 18B are cross-sectional views showing the manner in which a controller is translated with respect to the panel unit of the cassette shown in FIG. 16.
Figure 18B:
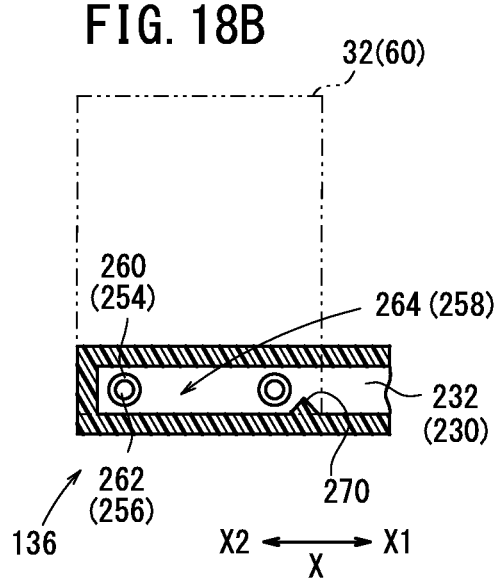

FIGS. 15A and 15B show the manner in which the controller 32 is translated along the directions of the arrow X by moving members 208 including wheels 210, rather than the moving members 128, 134 shown in FIGS. 6 through 7C. The moving mechanisms 136 are made up of the moving members 208 and the guides 48, 50.

Each of the moving members 208, which are disposed in the respective guides 48, 50, has four wheels 210 that travel on bottoms of the chambers 120, 122, a carriage 214 that extends in the directions of the arrow X and through which axles 212 of the four wheels 210 extend, and a joint 216 coupling the carriage 214 and the housing 60 of the controller 32 to each other. The entire length of each of the moving members 208 along the directions of the arrow X (the distance from the wheels 210 that face in the direction of the arrow X1 to the wheels 210 that face in the direction of the arrow X2) is essentially the same as the interval between the side surface 46*b* and the ridge 140*d*. Clearances, which are large enough for the wheels 210 to move vertically therein, are defined between the wheels 210 and the ceilings of the chambers 120, 122.

In FIGS. 15A and 15B, similar to the case of the moving members 128, 134, if the housing 60 is translated along the directions of the arrow X, the moving members 208 travel in unison with the housing 60 in the directions of the arrow X while being guided by the guides 48, 50. Since the moving members 208 travel upon rotation of the wheels 210, it is possible to easily and reliably translate the controller 32 with respect to the panel unit 30 along the directions of the arrow X. Since clearances, which are large enough for the wheels 210 to move vertically therein, are defined between the wheels 210 and the ceilings of the chambers 120, 122, even if the wheels 210 abut against the ridges 140*a* through 140*d*, the moving members 208 can travel over the ridges 140*a* through 140*d* along the directions of the arrow X.

FIGS. 16 through 18B show guides 220, 222 in the side surfaces 46*c*, 46*d*.

As with the guides 48, 50 (see FIGS. 2, 3, 5, and 6), the guides 220, 222 extend parallel to each other along the directions of the arrow X between the side surface 46*a* and the side surface 46*b*.

The housing 60 of the controller 32 has a ledge 226 on a side surface 80 thereof, which extends downward along the side surface 46*d*, and a ledge 224 on another side surface 80 thereof, which extends downward along the side surface 46*c*. The ledges 224, 226 are disposed in covering relation to portions of the guides 220, 222 proximate the side surface 46*b* (see FIGS. 16 and 17).

The guides 220, 222 have portions near the radiation conversion panel 92, which define respective chambers 230, 232 that are vertically wider than inlet portions of the guides 220, 222 in communication with the exterior.

Moving members 238, 244, which are substantially identical in shape to the moving members 128, 134 (see FIGS. 6 through 7C), or moving members 258, 264, which are capable of traveling on wheels 254, 260 similar to the moving members 208 (see FIGS. 15A and 15B), are coupled to the ledges 224, 226 of the housing 60 and are disposed in the guides 220, 222. The moving mechanisms 136 are made up of the moving members 238, 244, 258, 264 and the guides 220, 222.

The moving members 238, 244 have respective sliders 234, 240, which are disposed in the chambers 230, 232, and respective joints 236, 242 that join the sliders 234, 240 and the ledges 224, 226. The moving members 258, 264 have two respective wheels 254, 260 disposed in the chambers 230, 232, and respective axles 256, 262 that couple the wheels 254, 260 and the ledges 224, 226.

The moving members 238, 244, 258, 264 have total lengths along the directions of the arrow X, which are substantially the same as the interval between the side surface 46*b* and a ridge 270. Clearances, which are large enough for the sliders 234, 240 and the wheels 254, 260 to move vertically therein, are defined between the sliders 234, 240, the wheels 254, 260, and the ceilings of the chambers 230, 232.

In FIGS. 16 through 18B, similar to the case of the moving members 128, 134 and the moving members 208, in the case that the housing 60 is translated along the directions of the arrow X, the moving members 238, 244, 258, 264 are translated in unison with the housing 60 along the directions of the arrow X while being guided by the guides 220, 222. Since the clearances, which are large enough for the sliders 234, 240 and the wheels 254, 260 to move vertically therein, are defined between the sliders 234, 240, the wheels 254, 260, and the ceilings of the chambers 230, 232, even if the sliders 234, 240 and the wheels 254, 260 come into abutment against the ridge 270, the moving members 238, 244, 258, 264 travel over the ridge 270 along the directions of the arrow X.

Therefore, as shown in FIGS. 16 through 18B, it is possible to simply and reliably translate the controller 32 with respect to the panel unit 30 along the directions of the arrow X.

FIGS. 19A through 22 show grips disposed in locations other than the side surface 46a.

Figure 19A:
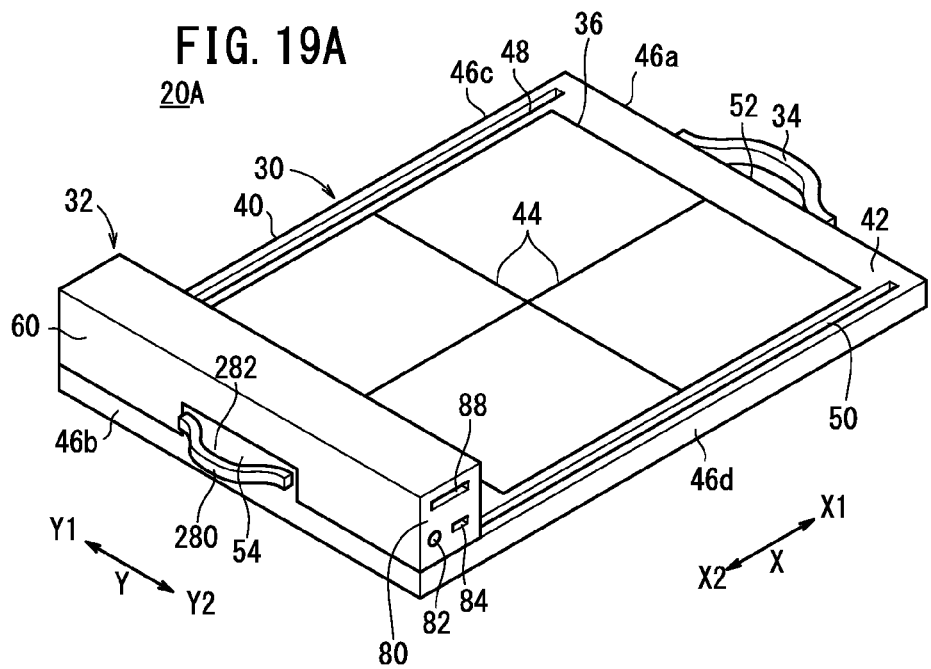
FIGS. 19A and 19B are perspective views of cassettes, which include two grips provided on panel units.

In FIG. 19A, in addition to the grip 34, another grip 280 is disposed on the side surface 46b of the block 54.

The grip 280 includes a handle that cooperates with the block 54 in defining a hole 282, which is large enough for a hand of the user 142 to be placed therein.

After having translated the controller 32 with respect to the panel unit 30 to the position shown in FIGS. 7B and 8A, for example, the user 142 grips the grip 34 with one hand and grips the grip 280 with the other hand, whereby the user can carry the electronic cassette 20A. Thus, the user 142 can carry the electronic cassette 20A with a well-balanced weight distribution. Furthermore, since the user 142 carries the electronic cassette 20A with both hands, the user 142 can carry the electronic cassette 20A with increased stability. The two grips 34, 280 make it possible for the user 142 to carry the electronic cassette 20A while gripping the grip 34 (see FIGS. 9A through 9C), and while the grip 280 is in an uppermost position. Consequently, the user 142 finds it easy to handle the electronic cassette 20A while carrying the same.

Figure 19B:
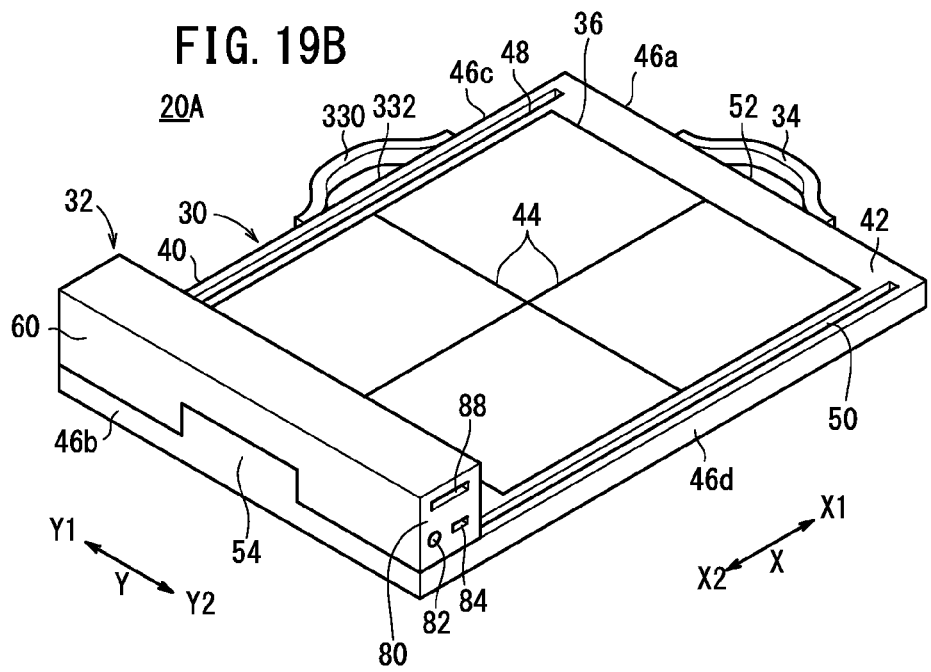

In FIG. 19B, in addition to the grip 34, another grip 330 is disposed on the side surface 46c. The grip 330 includes a handle that cooperates with the side surface 46c in defining a hole 332, which is large enough for a hand of the user 142 to be placed therein.

After having translated the controller 32 with respect to the panel unit 30 to the position shown in FIGS. 7B and 8A, for example, the user 142 grips the grip 330, which is held in an uppermost position, and can carry the electronic cassette 20A. Thus, the user 142 can carry the electronic cassette 20A stably with a well-balanced weight distribution. Furthermore, as a result of the two grips 34, 330, the user 142 finds it easy to handle the electronic cassette 20A while carrying the same, in the same manner as with the arrangement shown in FIG. 19A.

In FIG. 20A, in addition to the grip 34, another grip 290 is disposed on the upper surface of the housing 60 of the controller 32. The grip 290 includes a handle that cooperates with the upper surface of the housing 60 in defining a hole 292, which is large enough for a hand of the user 142 to be placed therein.

After having translated the controller 32 with respect to the panel unit 30 to the position shown in FIG. 20A, for example, the user 142 grips the grip 290, which is held in an uppermost position, and can carry the electronic cassette 20A. Thus, the user 142 can carry the electronic cassette 20A with a well-balanced weight distribution. Since the user 142 grips the heavy controller 32 directly through the grip 290, the electronic cassette 20A feels light while being carried by the user 142, and the user 142 finds it possible to carry the electronic cassette 20A easily and in a stable manner.

For translating the controller 32 with respect to the panel unit 30, the user 142 may do so by gripping the grip 290, and hence can easily translate the controller 32.

Therefore, with the structure shown in FIG. 20A, the grip 290 enables the user 142 to feel comfortable in handling the electronic cassette 20A upon carrying the electronic cassette 20A and translating the controller 32.

The structure shown in FIG. 20B differs from the structure shown in FIG. 20A, in that a foldable grip 300 is disposed on the upper surface of the housing 60.

The upper surface of the housing 60 has a substantially hexagonal recess 302 defined therein, and opposite ends of the grip 300 are disposed in the recess 302. The recess 302 houses a rectangular support 304 therein. A shaft 306, which extends through the support 304, has opposite ends coupled to respective opposite ends of the grip 300.

At times that the user 142 does not grip the grip 300, the grip 300 is placed in the recess 302. If the user 142 intends to grip the grip 300, the user 142 turns the central portion of the grip 300 about the shaft 306, pulls the grip 300 out of the recess 302, and grips the grip 300. For placing the grip 300 back into the recess 302, the user 142 turns the central portion of the grip 300 about the shaft 306 and inserts the grip 300 into the recess 302.

The structure shown in FIG. 20B provides the same advantages offered by the structure shown in FIG. 20A. In addition, since the user 142 may pull out the grip 300 only at times that the electronic cassette 20A is carried or the controller 32 is translated, the grip 300 does not present an obstacle to capturing radiographic images. Therefore, it is easier for the user 142 to handle the electronic cassette 20A.

The structure shown in FIG. 21A differs from the structure shown in FIG. 20A, in that a grip 310 is disposed on a side surface 308 of the housing 60. The grip 310 includes a handle that cooperates with the side surface 308 of the housing 60 in defining a hole 312, which is large enough for a hand of the user 142 to be placed therein.

The structure shown in FIG. 21B differs from the structure shown in FIG. 20B, in that a foldable grip 320 is disposed on the side surface 308 of the housing 60. The side surface 308 of the housing 60 has a substantially hexagonal recess 322 defined therein, and the grip 320 has opposite ends disposed in the recess 322. The recess 322 houses a rectangular support 324 therein. A shaft 326, which extends through the support 324, has opposite ends coupled to respective opposite ends of the grip 320.

The structures shown in FIGS. 21A and 21B offer the same advantages as the structures shown in FIGS. 20A and 20B.

FIG. 22 shows a foldable grip 410, which is mounted on the side surface 46a of the housing 60 instead of the grip 34. The side surface 46a of the housing 60 has a substantially hexagonal recess 412 defined therein, and the grip 410 has opposite ends disposed in the recess 412. The recess 412 houses a rectangular support 414 therein. A shaft 416, which extends through the support 414, has opposite ends coupled to respective opposite ends of the grip 410.

With the structure shown in FIG. 22, similar to the case of the structures shown in FIGS. 20A through 21B, since the user 142 grips the heavy controller 32 directly through the grip 410, the electronic cassette 20A feels light while the user 142 carries the same. Thus, it is possible for the user 142 to carry the electronic cassette 20A easily and in a stable manner.

In addition, since the user 142 pulls out the foldable grip 410 only if the electronic cassette 20A is being carried or if the controller 32 is to be translated, the grip 410 does not present an obstacle to capturing of radiographic images. Therefore, the user 142 finds it easier to handle the electronic cassette 20A.

Figure 23:
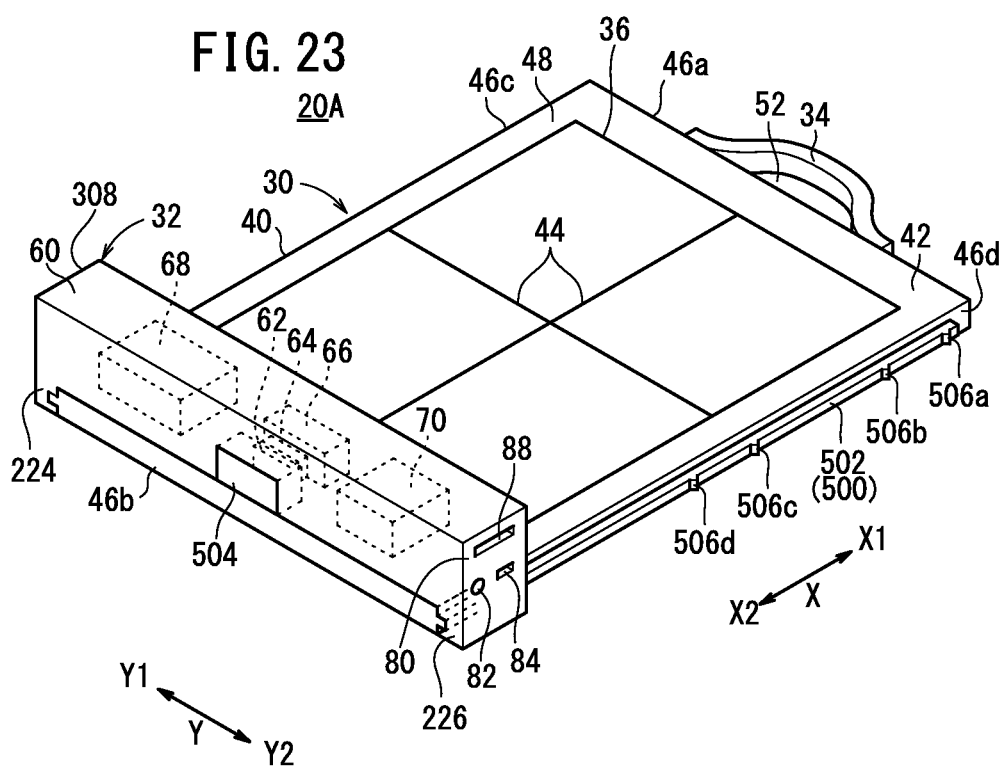
FIG. 23 is a perspective view of a cassette, which includes a rail-like guide on a side surface of a panel unit.
Figure 24:
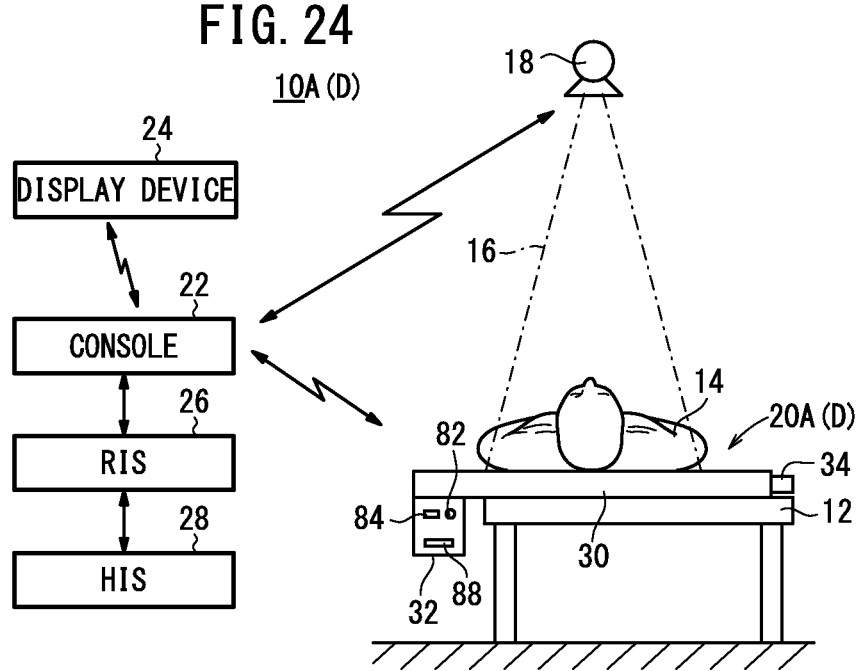
FIG. 24 is a schematic view of a radiographic image capturing system incorporating therein a double-sided image capturing cassette.

The electronic cassette 20A according to the first embodiment may incorporate further structural details as shown in FIGS. 23 and 24.

FIG. 23 shows rail-like guides 500, 502, which are disposed on the side surfaces 46c, 46d, respectively, instead of the guides 220, 222 described above. The guides 500, 502 have a plurality of chevron-shaped ridges 506a through 506d, which function the same as the aforementioned ridges 140a through 140d, 270. A block 504, which has the same function as the aforementioned block 54, is removably mounted on the housing 40 at the side surface 46b of the irradiation surface 42. In FIG. 23, the ledges 224, 226 are constructed as moving members (sliders), which are slidable along the guides 500, 502.

The structure shown in FIG. 23 offers the same advantages as the guides 220, 222 and the ridges 270 described above. If the controller 32 is slid along the guides 500, 502 in the direction of the arrow X2 with the block 504 removed from the housing 40, the controller 32 can be detached from the panel unit 30. As a result, the electronic cassette 20A can easily be serviced for maintenance and replacement of parts.

The electronic cassette 20A, which includes the guides 48, 50, 220, 222 and the ridges 140a through 140d, 270, may include the block 504 instead of the block 54 to thereby provide the advantages that are offered by the block 504.

According to the above embodiment, the irradiation surface 42 is irradiated with radiation 16. However, as shown in FIG. 24, if a double-sided image capturing electronic cassette 20A is employed, then the subject 14 may be imaged after the electronic cassette 20A has been turned upside down and placed on the image capturing base 12. In this case, the bottom surface of the panel unit 30 serves as an image capturing surface that is irradiated with radiation 16, and the grid 90 and the lead plate 94 may be dispensed with.

The above modification offers the same advantages as the embodiment described above. Furthermore, since the irradiation surface 42 or the bottom surface can be selected as an image capturing surface depending on the image capturing method to be carried out on the subject 14, the electronic cassette 20A can be handled with increased ease.

The first embodiment also is applicable to capturing of radiographic images using a light readout type radiation conversion panel. A light readout type radiation conversion panel operates in the following manner. In a case where radiation is applied to each solid-state detector, an electrostatic latent image, which depends on the dose of applied radiation, is stored and recorded in the solid-state detector. For reading the electrostatic latent image, the radiation conversion panel is irradiated with reading light, and the value of an electric current generated by the radiation conversion panel is acquired as a radiographic image. The radiation conversion panel may be reused after being irradiated with erasing light, to thereby erase the radiographic image, which remains as a residual electrostatic latent image (see Japanese Laid-Open Patent Publication No. 2000-105297).

In order to prevent blood and bacteria from attaching to the electronic cassette 20A, the entire electronic cassette 20A may be of a water-resistant and hermetically sealed structure, and the electronic cassette 20A may be sterilized and cleaned as necessary, so that a single electronic cassette 20A can be used repeatedly.

The first embodiment is not limited to capturing of radiographic images in medical organizations, but also may be applied to capturing of images of subjects at disaster sites or in home-care service sites, or may be installed on medical checkup motor vehicles for capturing images of subjects. The first embodiment is not limited to use in capturing of radiographic images in the medical field, but may also be applied to capturing of radiographic images in various nondestructive tests.

The first invention is not limited to the above embodiment, but various alternative arrangements may be adopted without departing from the scope of the first invention.

Figure 25:
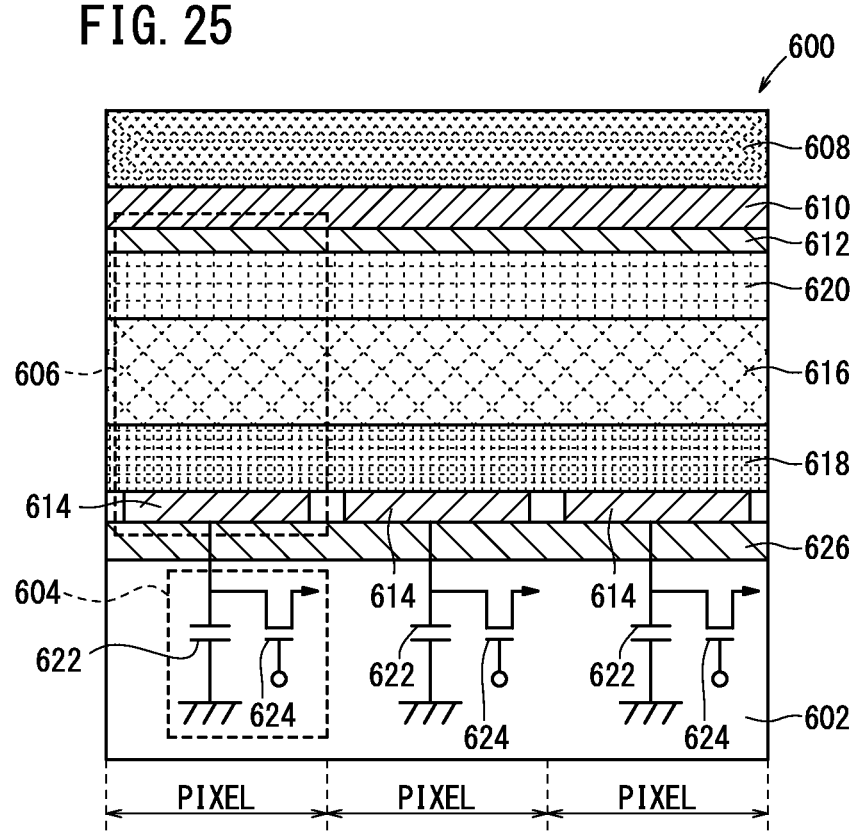
FIG. 25 is a schematic view of the structure of three pixels in a radiation detector according to a modification.
Figure 26:
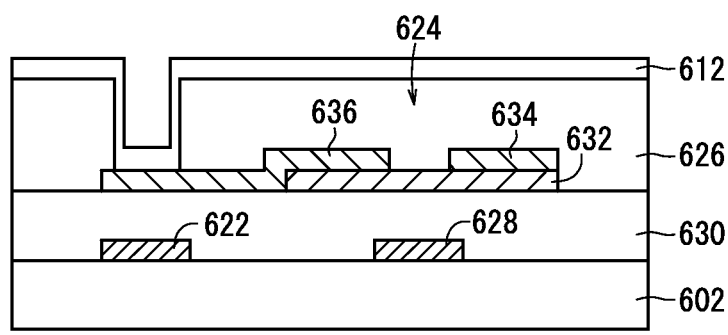
FIG. 26 is a schematic view of a TFT and a charge storage region shown in FIG. 25.
Figure 27:
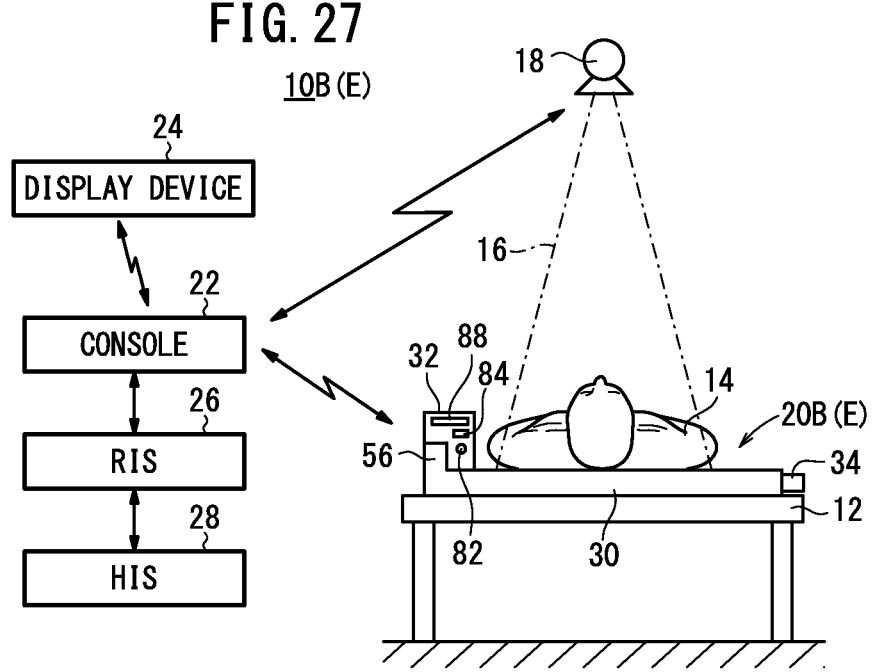
FIG. 27 is a schematic view of a radiographic image capturing system incorporating a cassette therein according to a second embodiment of the present invention.
Figure 28:
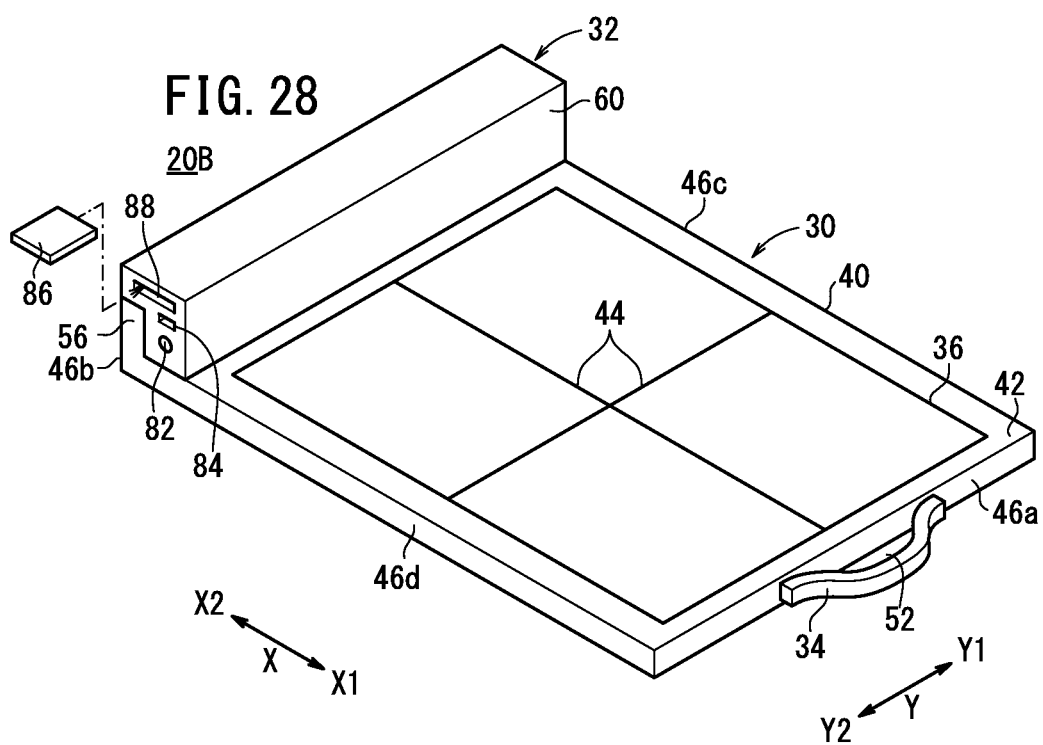
FIG. 28 is a perspective view of the cassette shown in FIG. 27.

For example, the radiation conversion panel 92 may comprise a radiation detector 600 according to the modification shown in FIGS. 25 and 26. FIG. 25 is a schematic cross-sectional view of three pixels of the radiation detector 600 according to the modification.

The radiation detector 600 includes a signal output section 604 including switching elements, a sensor 606 including solid-state detectors, and a scintillator 608, which are successively deposited on an insulating substrate 602. The signal output section 604 and the sensor 606 jointly make up a pixel. The radiation detector 600 includes a matrix of pixels arrayed on the insulating substrate 602. In each of the pixels, the signal output section 604 is superposed on the sensor 606.

The scintillator 608 is disposed over the sensor 606 with a transparent insulating film 610 interposed therebetween. The scintillator 608 is in the form of a film of phosphor, which serves to emit light converted from radiation 16. If the upper surface (remote from the substrate 602) in FIG. 25 serves as an irradiation surface 42 (see FIGS. 2 through 5, 8A through 9C, 13 through 14B, 16, and 19A through 23), then in the case that radiation 16 is applied from above, the radiation detector 600 functions as a PSS-type radiation detector, and the phosphor of the scintillator 608 emits light converted from the applied radiation 16.

Light emitted by the scintillator 608 preferably has a visible wavelength range (from 360 nm to 830 nm). If the radiation detector 600 is used to capture a monochromatic image, then light emitted by the scintillator 608 preferably includes a green wavelength range.

If X-rays are used as radiation 16, then the phosphor that is used in the scintillator 608 preferably includes CsI, and more preferably, includes CsI(Tl) (thallium-added cesium iodide) which, upon being irradiated with X-rays, emits light in a wavelength spectrum ranging from 420 nm to 700 nm. Light emitted from CsI(Tl) has a peak wavelength of 565 nm in the visible range.

The scintillator 608 may be formed by depositing CsI(Tl) having a columnar crystalline structure on an evaporation base. If the scintillator 608 is formed by such an evaporation process, then the evaporation base preferably, but not necessarily, is made of Al, from the standpoints of X-ray transmittance and cost. If the scintillator 608 is made of GOS, then a resin base may be coated with GOS, which then is applied to the surface of a TFT active matrix substrate. In this manner, the TFT active matrix substrate can be saved in the event of a coating failure of the GOS.

The sensor 606 includes an upper electrode 612, a lower electrode 614, and a photoelectric conversion film 616 disposed between the upper electrode 612 and the lower electrode 614.

Since light emitted by the scintillator 608 must be applied to the photoelectric conversion film 616, the upper electrode 612 preferably is made of an electrically conductive material, which is transparent to at least the wavelength of light emitted by the scintillator 608. More specifically, the upper electrode 612 preferably is made of a transparent conducting oxide (TCO), which exhibits a high transmittance with respect to visible light and has a small resistance value. Although the upper electrode 612 may be a thin metal film such as Au or the like, TCO is preferable because Au tends to exhibit an increased resistance value at a transmittance of 90% or higher. For example, ITO (Indium Tin Oxide), IZO, AZO, FTO, $SnO_2$, $TiO_2$, $ZnO_2$, or the like preferably is used as the material for the upper electrode 612. Among such materials, ITO is the most preferable from the standpoints of process simplification, low resistance, and transparency. The upper electrode 612 may be a single electrode that is shared by all the pixels, or the upper electrode 612 may be a plurality of electrodes assigned to respective pixels.

The photoelectric conversion film 616, which contains an organic photoconductor (OPC), absorbs light emitted from the scintillator 608 and generates electric charges depending on the absorbed light. The photoelectric conversion film 616, which contains an organic photoconductor (organic photoelectric conversion material), has a sharp absorption spectrum in the range of visible light, and does not absorb electromagnetic waves apart from light emitted from the scintillator 608. Therefore, noise, which would otherwise be produced if radiation 16 were absorbed by the photoelectric conversion film 616, is effectively minimized. The photoelectric conversion film 616 may contain a-Si instead of an organic photoconductor. A photoelectric conversion film 616 containing a-Si has a wide absorption spectrum for efficiently absorbing light emitted from the scintillator 608.

In order for the organic photoconductor of the photoelectric conversion film 616 to absorb light emitted by the scintillator 608 most efficiently, the absorption peak wavelength thereof preferably is as close as possible to the light emission peak wavelength of the scintillator 608. Although the absorption peak wavelength of the organic photoconductor and the light emission peak wavelength of the scintillator 608 should ideally be in agreement with each other, it is possible to sufficiently absorb light emitted by the scintillator 608 if the difference between the absorption peak wavelength and the light emission peak wavelength is small enough. More specifically, the difference between the absorption peak wavelength of the organic photoconductor and the light emission peak wavelength of the scintillator 608 with respect to radiation 16 preferably is 10 nm or smaller, and more preferably, 5 nm or smaller.

Organic photoconductors that meet the above requirements include quinacridone-based organic compounds and phthalocyanine-based organic compounds. Since quinacridone has an absorption peak wavelength of 560 nm in the visible range, if quinacridone is used as the organic photoelectric conversion material and CsI(Tl) is used as the material for the scintillator 608, the difference between the above peak wavelengths can be reduced to 5 nm or less, thereby making it possible to substantially maximize the amount of electric charge generated by the photoelectric conversion film 616.

The sensor 606 includes an organic layer formed by superposition or mixture of an electromagnetic wave absorption region, a photoelectric conversion region, an electron transport region, a hole transport region, an electron blocking region, a hole blocking region, a crystallization preventing region, an electrode, and an interlayer contact improving region, etc. The organic layer preferably includes an organic p-type compound (organic p-type semiconductor) or an organic n-type compound (organic n-type semiconductor).

An organic p-type semiconductor is a donor organic semiconductor (compound) typified primarily by a hole transport organic compound, and refers to an organic compound that tends to donate electrons. More specifically, if two organic materials are used in contact with each other, one of the organic materials, which has a lower ionization potential, is referred to as a donor organic compound. Any type of electron-donating organic compound can be used as the donor organic compound.

An organic n-type semiconductor is an acceptor organic semiconductor (compound) typified primarily by an electron transport organic compound, and refers to an organic compound that tends to accept electrons. More specifically, if two organic materials are used in contact with each other, one of the organic materials, which has a larger electron affinity, is referred to as an acceptor organic compound. Any type of electron-accepting organic compound can be used as the acceptor organic compound.

Materials that can be used as the organic p-type semiconductor and the organic n-type semiconductor, and arrangements of the photoelectric conversion film 616 are disclosed in detail in Japanese Laid-Open Patent Publication No. 2009-032854, and such features will not be described in detail below. The photoelectric conversion film 616 may contain fullerene or carbon nanotubes.

The thickness of the photoelectric conversion film 616 should be as large as possible for the purpose of absorbing light from the scintillator 608. However, if the thickness of the photoelectric conversion film 616 is greater than a certain value, then the intensity of the electric field, which is produced on the photoelectric conversion film 616 by a bias voltage applied from opposite ends of the photoelectric conversion film 616, is reduced and electric charges cannot be collected. The thickness of the photoelectric conversion film 616 preferably is in the range from 30 nm to 300 nm, more preferably, in the range from 50 nm to 250 nm, and even more preferably, in the range from 80 nm to 200 nm.

The photoelectric conversion film 616 is illustrated as being shared by all of the pixels. However, the photoelectric conversion film 616 may be divided into a plurality of films assigned to respective pixels. As illustrated, the lower electrode 614 comprises a plurality of thin films assigned to respective pixels. However, the lower electrode 614 may be a single thin film that is shared by all of the pixels. The lower electrode 614 may be made of a transparent or opaque electrically conductive material, preferably Al, silver, or the like. The thickness of the lower electrode 614 may be in the range from 30 nm to 300 nm.

If a prescribed bias voltage is applied between the upper electrode 612 and the lower electrode 614, the sensor 606 moves one type of electric charge (holes or electrons) generated in the photoelectric conversion film 616 to the upper electrode 612, and moves the other type of electric charge to the lower electrode 614. With the radiation detector 600 according to the present modification, an interconnection is connected to the upper electrode 612 for applying the bias voltage therethrough to the upper electrode 612. The bias voltage has a polarity, which is set so as to move electrons generated in the photoelectric conversion film 616 to the upper electrode 612, and to move holes to the lower electrode 614. However, the bias voltage may have an opposite polarity.

The sensor 606 of each pixel includes at least the lower electrode 614, the photoelectric conversion film 616, and the upper electrode 612. For preventing dark current from increasing, the sensor 606 preferably additionally includes either an electron blocking film 618 or a hole blocking film 620, and more preferably, includes both the electron blocking film 618 and the hole blocking film 620.

The electron blocking film 618 may be disposed between the lower electrode 614 and the photoelectric conversion film 616. In the case that a bias voltage is applied between the lower electrode 614 and the upper electrode 612, the electron blocking film 618 is capable of preventing electrons from being injected from the lower electrode 614 into the photoelectric conversion film 616, thereby preventing dark current from increasing.

The electron blocking film 618 may be made of an electron-donating organic material. The electron blocking film 618 actually is made of a material selected depending on the material of the electrode and the material of the photoelectric conversion film 616, which are disposed adjacent thereto. A preferable material has an electron affinity (Ea), which is at least 1.3 eV greater than the work function (Wf) of the material of the adjacent electrode, and an ionization potential (Ip), which is equal to or smaller than the Ip of the material of the adjacent photoelectric conversion film 616. Materials that can be used as an electron-donating organic material are disclosed in detail in Japanese Laid-Open Patent Publication No. 2009-032854, and such features will not be described in detail below.

The thickness of the electron blocking film 618 preferably is in the range from 10 nm to 200 nm, more preferably, in the range from 30 nm to 150 nm, and even more preferably, in the range from 50 nm to 100 nm, in order to reliably achieve a dark current reducing capability and to prevent the photoelectric conversion efficiency of the sensor 606 from being lowered.

The hole blocking film 620 may be disposed between the photoelectric conversion film 616 and the upper electrode 612. If a bias voltage is applied between the lower electrode 614 and the upper electrode 612, the hole blocking film 620 can prevent holes from being injected from the upper electrode 612 into the photoelectric conversion film 616, thereby preventing dark current from increasing.

The hole blocking film 620 may be made of an electron-accepting organic material. The thickness of the hole blocking film 620 preferably is in the range from 10 nm to 200 nm, more preferably, in the range from 30 nm to 150 nm, and even more preferably, in the range from 50 nm to 100 nm, in order to reliably achieve a dark current reducing capability and to prevent the photoelectric conversion efficiency of the sensor 606 from being lowered.

The hole blocking film 620 actually is made of a material selected depending on the material of the electrode adjacent thereto, as well as the material of the photoelectric conversion film 616 adjacent thereto. A preferable material has an ionization potential (Ip) that is at least 1.3 eV greater than the work function (Wf) of the material of the adjacent electrode, and an electron affinity (Ea) equal to or greater than the Ea of the material of the adjacent photoelectric conversion film 616. Materials that can be used as an electron-accepting organic material are disclosed in detail in Japanese Laid-Open Patent Publication No. 2009-032854, and such features will not be described in detail below.

For setting a bias voltage to move holes, from among the electric charges generated in the photoelectric conversion film 616, toward the upper electrode 612, and to move electrons, from among the electric charges generated in the photoelectric conversion film 616, toward the lower electrode 614, the electron blocking film 618 and the hole blocking layer 620 may be switched in position. Both of the electron blocking film 618 and the hole blocking layer 620 are not necessarily required, and either one of the electron blocking film 618 or the hole blocking layer 620 may be included to provide a certain dark current reducing capability.

As shown in FIG. 26, the signal output section 604 is disposed on the surface of the substrate 602 in alignment with the lower electrode 614 of each pixel, and includes a storage capacitor 622 for storing electric charges that have moved to the lower electrode 614, together with a TFT 624 for converting electric charges stored in the storage capacitor 622 into electric signals and outputting the electric signals. The storage capacitor 622 and the TFT 624 are disposed in a region underlying the lower electrode 614 as viewed in plan. Such a structure makes the signal output section 604 and the sensor 606 superposed in each pixel in the thickness direction. If the signal output section 604 is formed so as to fully cover the storage capacitor 622 and the TFT 624 with the lower electrode 614, then the planar area of the radiation detector 600 (pixels) can be minimized.

The storage capacitor 622 is electrically connected to the corresponding lower electrode 614 by an electrically conductive interconnection, which extends through an insulating film 626 that is interposed between the substrate 602 and the lower electrode 614. The interconnection allows electric charges collected by the lower electrode 614 to move into the storage capacitor 622.

The TFT 624 includes a stacked assembly made up of a gate electrode 628, a gate insulating film 630, and an active layer (channel layer) 632. A source electrode 634 and a drain electrode 636 are disposed on the active layer 632 and are spaced from each other by an intervening gap. The active layer 632 may be made of a-Si, an amorphous oxide, an organic semiconductor material, carbon nanotubes, or the like, for example, but is not limited to such materials.

Amorphous oxide, which the active layer 632 may be made of, preferably is an oxide (e.g., In—O oxide) including at least one of In, Ga, and Zn, and more preferably, is an oxide (e.g., In—Zn—O oxide, In—Ga—O oxide, or Ga—Zn—O oxide) including at least two of In, Ga, and Zn, and even more preferably, is an oxide including In, Ga, and Zn. An In—Ga-An-O amorphous oxide preferably is an amorphous oxide the crystalline composition of which is represented by $InGaO_3(ZnO)_m$, where m represents a natural number smaller than 6, and more preferably, is $InGaZnO_4$. However, the amorphous oxide that makes up the active layer 632 is not limited to the above materials.

An organic semiconductor material, which the active layer 632 is made of, may be a phthalocyanine compound, pentacene, vanadyl phthalocyanine, or the like, but is not limited to such materials. Details of a phthalocyanine compound are disclosed specifically in Japanese Laid-Open Patent Publication No. 2009-212389, and such features will not be described below.

If the active layer 632 of the TFT 624 is made of amorphous oxide, an organic semiconductor material, or carbon nanotubes, then since the active layer 632 does not absorb radiation 16 such as X-rays or the like, or only absorbs trace amounts of radiation 16, it is possible to effectively reduce noise produced in the signal output section 604.

If the active layer 632 is made of carbon nanotubes, then the switching rate of the TFT 624 is increased, and the TFT 624 absorbs light in the visible range at a low rate. For making the active layer 632 of carbon nanotubes, it is necessary to separate and extract highly pure carbon nanotubes by way of centrifugal separation or the like, because the performance of the TFT 624 will be greatly reduced if trace metallic impurities become trapped in the active layer 632.

The amorphous oxide, the organic semiconductor material, the carbon nanotubes, and the organic semiconductor material described above can be deposited as films at low temperatures. Therefore, the substrate 602 is not limited to being a highly heat-resistant substrate such as a semiconductor substrate, a quartz substrate, a glass substrate, or the like, but may be a flexible substrate of plastic, a substrate of aramid fibers, or a substrate of bionanofibers. More specifically, the substrate 602 may be a flexible substrate of polyester such as polyethylene terephthalate, polybutylene phthalate, polyethylene naphthalate, or the like, polystyrene, polycarbonate, polyethersulfone, polyarylate, polyimide, polycycloolefin, norbornene resin, polychlorotrifluoroethylene, or the like. The flexible substrate enables the radiation detector 600 to be light in weight and hence easy to carry.

By making the photoelectric conversion film 616 of an organic photoconductor and making the TFT 624 of an organic semiconductor material, it is possible to grow the photoelectric conversion film 616 and the TFT 624 at a low temperature on the flexible substrate of plastic (substrate 602), as well as to make the radiation detector 600 thin and lightweight overall. The panel unit 30, which houses the radiation detector 600 therein (see FIGS. 1 through 6, 8A through 9C, 13 through 14B, 16, 17, and 19A through 24), can also be made thin and lightweight. The flexible substrate 602 enables the radiation conversion panel 92 and the housing 40 of the panel unit 30, which houses the radiation conversion panel 92 therein, to be made flexible as well. As a result, the radiation conversion panel 92 can be prevented from becoming damaged if loads are applied thereto, i.e., in a case where a subject 14 is placed on the panel unit 30.

The substrate 602 may include an insulating layer for making the substrate 602 electrically insulative, a gas barrier layer for making the substrate 602 impermeable to water and oxygen, and an undercoat layer for making the substrate 602 flat for enhancing intimate contact with the electrode.

Aramid fibers for use as the substrate 602 are advantageous in that, since a high-temperature process at 200 degrees Celsius is applicable thereto, aramid fibers allow a transparent electrode material to be set at a high temperature for lower resistance, and also permit driver ICs to be automatically mounted thereon by a process including a solder reflow process. Furthermore, inasmuch as aramid fibers have a coefficient of thermal expansion that is close to that of ITO and glass, a substrate made of aramid fibers is less liable to warp and crack after fabrication. In addition, a substrate made of aramid fibers may be made thinner than a glass substrate or the like. The substrate 602 may be in the form of a stacked assembly of an ultrathin glass substrate and aramid fibers.

Bionanofibers are made by compounding a bundle of cellulose microfibrils (bacteria cellulose) produced by bacteria (acetic acid bacteria, Acetobacter Xylinum) and a transparent resin. The bundle of cellulose microfibrils has a width of 50 nm, which is 1/10 of the wavelength of visible light, is highly strong and highly resilient, and is subject to low thermal expansion. Bionanofibers which contain 60% to 70% fibers and exhibit a light transmittance of about 90% at a wavelength of 500 nm can be produced by impregnating bacteria cellulose with a transparent resin such as an acrylic resin, an epoxy resin, or the like, and setting the transparent resin. Bionanofibers have a low coefficient of thermal expansion ranging from 3 ppm to 7 ppm, which is comparable to silicon crystals, a high strength of 460 Mpa that matches the strength of steel, and a high resiliency of 30 GPa, and are flexible. Therefore, a substrate 602 made of bionanofibers can be thinner than glass substrates or the like.

According to the present modification, the signal output section 604, the sensor 606, and the transparent insulating film 610 are successively formed on the substrate 602. The scintillator 608 is bonded above the substrate 602 by an adhesive resin having low light absorption, thereby completing the radiation detector 600.

With the radiation detector 600 according to the above modification, since the photoelectric conversion film 616 is made of an organic photoconductor, and the active layer 632 of the TFT 624 is made of an organic semiconductor material, the photoelectric conversion film 616 and the signal output section 604 absorb almost no radiation 16. Therefore, any reduction in sensitivity to radiation 16 (see FIGS. 1, 4, and 24) is minimized.

The organic semiconductor material, which the active layer 632 of the TFT 624 is made of, and the organic photoconductor, which the photoelectric conversion film 616 is made of, can be grown as films at low temperatures. Therefore, the substrate 602 can be formed of plastic resin, aramid fibers, or bionanofibers, which absorb radiation 16 by a small degree. Therefore, any reduction in sensitivity to radiation 16 can be further minimized.

If the radiation detector 600 is placed in the housing 40 and the substrate 602 is made of plastic resin, aramid fibers, or bionanofibers, which are highly rigid, then since the radiation detector 600 itself has increased rigidity, the housing 40 can be made thinner. If the substrate 602 is made of plastic resin, aramid fibers, or bionanofibers, which are highly rigid, then since the radiation detector 600 itself is flexible as described above, the radiation detector 600 is less likely to be damaged if the housing 40 is subjected to impacts.

FIG. 25 shows a PSS-type radiation detector 600, for example, in which light emitted from the scintillator 608 is converted into electric charges by the sensor 606 (photoelectric conversion film 616), which is positioned remotely from the radiation source 18 (see FIGS. 1 and 24), thereby reading a radiographic image.

However, the radiation detector 600 is not limited to the above structure, and may be constructed as an ISS-type radiation detector. In an ISS-type radiation detector, the substrate 602, the signal output section 604, the sensor 606, and the scintillator 608 are stacked in this order along the direction in which radiation 16 is applied. Light emitted from the scintillator 608 is converted into electric charges by the sensor 606, which is positioned closer to the radiation source 18, thereby reading a radiographic image. Since the scintillator 608 emits light more strongly from the irradiation surface than from the reverse side thereof, an ISS-type radiation detector 600 has a shorter distance along which light emitted from the scintillator 608 reaches the photoelectric conversion film 616 than the PSS-type radiation detector 600. Since light is not dispersed and attenuated as much, the resolution of the radiographic image is increased.

If the radiation conversion panel 92 (radiation detector 600) is made of the plastic and organic materials referred to above, then the ISS-type radiation conversion panel 92, in which the substrate 602, the TFT 624, the photoelectric conversion film 616, and the scintillator 608 of CsI are successively arranged along the direction in which radiation 16 is applied, makes it easy to obtain high-quality radiographic images.

According to the first embodiment, as described above, the scintillator 608 can be made of CsI or GOS.

If an electric circuit such as the controller 32 generates heat, the sensitivity of GOS remains unchanged despite such heat. However, the sensitivity of CsI is lowered as the temperature rises (i.e., sensitivity is lowered by about 0.3% in response to a temperature increase of 1° C.).

According to the first embodiment, the housing 40 of the panel unit 30, which houses the scintillator 608 therein, and the controller 32 are separate from each other. Under operation, the controller 32 is coupled (connected) to the housing 40 in spaced relation to the scintillator 608. Therefore, although the scintillator 608 is made of CsI, the sensitivity thereof is prevented from being changed due to heat generated by the controller 32. Accordingly, it is possible to acquire high-sensitivity radiographic images even if the image capturing process continues for a long period of time.

According to the first embodiment, as shown in FIGS. 1 through 5, 13 through 14B, 16, 19A, 19B, and 22 through 24, at times that the controller 32 is in operation, the controller 32 does not underlie the radiation conversion panel 92 in the panel unit 30 as viewed in plan. If heat generated by the controller 32 is transmitted to the radiation conversion panel 92, then a temperature distribution caused by such heat tends to be developed at opposite ends of the radiation conversion panel 92. If the scintillator 608 is made of CsI, then such a temperature distribution is likely to cause sensitivity irregularities, which cannot be corrected in terms of images. Therefore, if a CsI scintillator 608 is used, certain structures thereof must be used so as not to transmit heat generated by the controller 32 to the radiation conversion panel 92 in the panel unit 30. More specifically, the structures described below should be added.

(1) A heat radiating member, such as a heat radiating window or a heat radiating plate for radiating heat generated by the controller 32, may be disposed at a location in the housing 60 of the controller 32, which is spaced from the panel unit 30 (opposite to the panel unit 30).

(2) The grips 290, 300, 310, 320, 410 (see FIGS. 20A through 22) may be made of a material having a high coefficient of thermal conductivity, whereby the grips 290, 300, 310, 320, 410 can be used as a heat radiating member for radiating heat generated by the controller 32. A wavy or rectangular member, which functions as a heat sink, may be mounted on the grips 290, 300, 310, 320, 410 for increasing the heat radiating area thereof. Since the grips 290, 300, 310, 320, 410 are mounted directly on the housing 60 of the controller 32, the grips 290, 300, 310, 320, 410 can directly radiate heat generated by the controller 32. Furthermore, inasmuch as the user 142 grips the grips 290, 300, 310, 320, 410, the grips 290, 300, 310, 320, 410 need to radiate heat in a manner that does not cause the user 142 to suffer a low temperature burn.

The grips 34, 280, 330 mounted on the panel unit 30 (see, FIGS. 1 through 5, 8A, 9A through 9C, 13 through 14B, 16, 19A through 21B, 23, and 24) may also be used as a heat radiating member if the grips 34, 280, 330 are made of a material having a high coefficient of thermal conductivity, insofar as the controller 32 is disposed in the vicinity of the grips 34, 280, 330. A wavy or rectangular member may also be mounted on the grips 34, 280, 330 for increasing the heat radiating area thereof. Moreover, the grips 34, 280, 330 also must radiate heat in a manner so as not to cause the user 142 to suffer a low temperature burn.

The housing 60 of the controller 32 houses therein components that generate a large amount of heat, such as the power supply 68, etc. Therefore, such components, which generate a large amount of heat, may be positioned in the housing 60 near the grips 290, 300, 310, 320, 410 for efficiently radiating heat generated by the controller 32 through the grips 290, 300, 310, 320, 410.

(3) The guides 48, 50, 220, 222, 500, 502 and the moving members 128, 134, 208, 238, 244, 258, 264 for translating the controller 32 may be made of a metal having a high coefficient of thermal conductivity, so as to function as a heat radiating member for radiating heat generated by the controller 32. Since the guides 48, 50, 220, 222, 500, 502 are exposed on the housing 40 of the panel unit 30 along the directions of the arrow X, the guides 48, 50, 220, 222, 500, 502 can efficiently radiate heat generated by the controller 32, even if the housing 40 is made of a material such as carbon or the like, which is less likely to release heat, for the purpose of making itself lightweight. Moreover, since the driver circuit 98 (and an IC including the same) also generates heat, the driver circuit 98 and the guides 48, 50, 220, 222, 500, 502 may be thermally coupled to each other, so that heat generated by the driver circuit 98 can be radiated through the guides 48, 50, 220, 222, 500, 502.

(4) A gel-like cooling sheet may be used as the cushioning members 200, 202 (see FIGS. 14A and 14B) for protecting the housing 60 from impacts. The cooling sheet, which has a structure including a non-woven fabric and a high-polymer gel bonded to each other, deprives the controller 32 of the heat generated thereby, and evaporates water contained in the gel with such heat, for thereby radiating heat generated by the controller 32 in order to lower the temperature of the controller 32.

Structures (1) through (4) described above are effective in avoiding transfer of heat to the radiation detector 600 (radiation conversion panel 92), which includes the CsI scintillator 608, for thereby minimizing a reduction in sensitivity to radiation 16, and also for minimizing sensitivity irregularities of the radiation detector 600.

2. Description of Second Embodiment:

A radiographic image capturing apparatus according to a preferred embodiment of a second invention (second embodiment) will be described in detail below with reference to FIGS. 27 through 51.

Components of the second embodiment, which are identical to those of the first embodiment (see FIGS. 1 through 26), are denoted by identical reference characters, and such features will not be described in detail below, although such features may be described, if necessary, with reference to FIGS. 1 through 26. This also applies to other embodiments to be described later.

<Description of Arrangement of the Second Embodiment>

A radiographic image capturing system 10B incorporates therein an electronic cassette 20B, which serves as a radiographic image capturing apparatus according to the second embodiment. The electronic cassette 20B has a block 56 that projects upwardly from a corner of the irradiation surface 42, which faces in the direction of the arrow X2 (at the side surface 46b) and in the direction of the arrow Y2 (at the side surface 46d). The controller 32 is disposed on the irradiation surface 42 on the side surface 46b thereof, so as to cover the block 56 from above.

The housing 60 of the controller 32 extends along the directions of the arrow Y (directions parallel to the side surfaces 46a, 46b) so as to cover the block 56 from above. The housing 60 houses therein a connection terminal 78 in the form of a leaf spring for contacting a connection terminal (connector) 76 that is mounted on a side surface of the block 56, and which faces in the direction of the arrow X1 (toward the side surface 46a). The cassette controller 66 is electrically connected to the connection terminal 78 for controlling the panel unit 30 through the connection terminals 76, 78, the power supply 68, and the communication unit 70.

If the connection terminals 76, 78 are held in contact with each other, the power supply 68 supplies electric power to the panel unit 30 through the connection terminals 76, 78 while also supplying electric power to the cassette controller 66 and the communication unit 70. If the connection terminals 76, 78 are separated from each other, thereby electrically disconnecting the panel unit 30 and the controller 32 from each other, the power supply 68 supplies electric power only to the cassette controller 66. In the panel unit 30, the driver circuit 98 is electrically connected to the connection terminal 76 through the flexible board 100.

Figure 31:
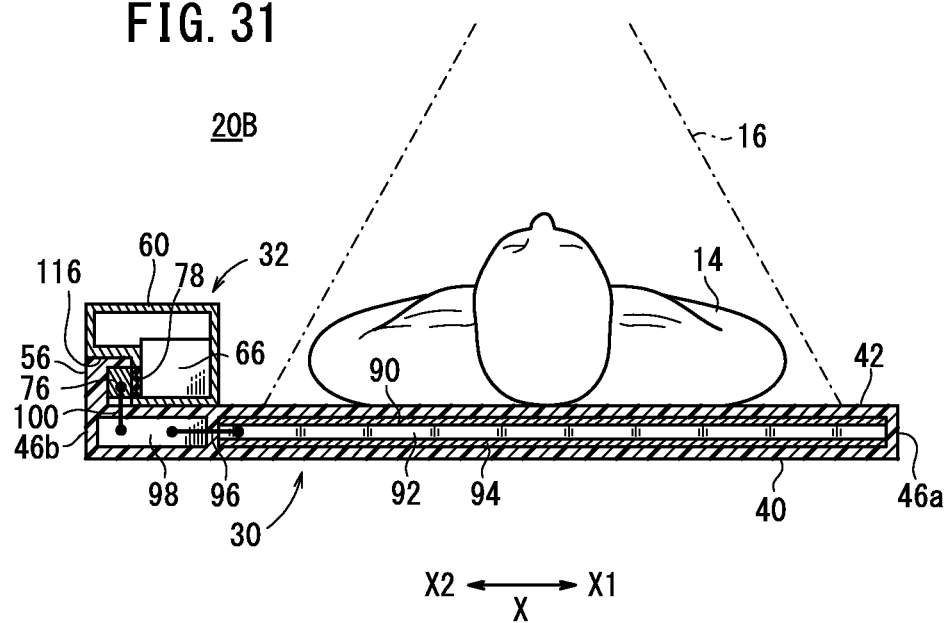
FIG. 31 is a cross-sectional view taken along line XXXI-XXXI of FIG. 29.

As shown in FIG. 31, the housing 60 has a recess 116 defined in a side thereof, which faces in the direction of the arrow X2, and the connection terminal 78 is disposed in the recess 116. If the block 56 engages in the recess 116 such that the connection terminals 76, 78 are held in contact with each other, the cassette controller 66 becomes electrically connected to the driver circuit 98 through the connection terminals 78, 76 and the flexible board 100.

According to the second embodiment, the connected state detector 186 (see FIG. 11) detects whether or not the connection terminals 76, 78 are electrically connected to each other, and based on the detection result, controls supply of electric power from the power supply 68 to various components in the electronic cassette 20B.

A vertical shaft 74 is disposed substantially centrally on the irradiation surface 42 at the side surface 46b. The bottom surface of the housing 60 has an oblong hole 72 defined therein through which the shaft 74 extends, and which extends along longitudinal directions of the housing 60 (along directions of the arrow Y in FIGS. 29 and 32). The hole 72 extends from a central region of the bottom surface of the housing 60 to a position near the side surface 308. Therefore, the cassette controller 66, the power supply 68, and the communication unit 70 are centrally located in the housing 60 near the side surface 80.

Figure 32:
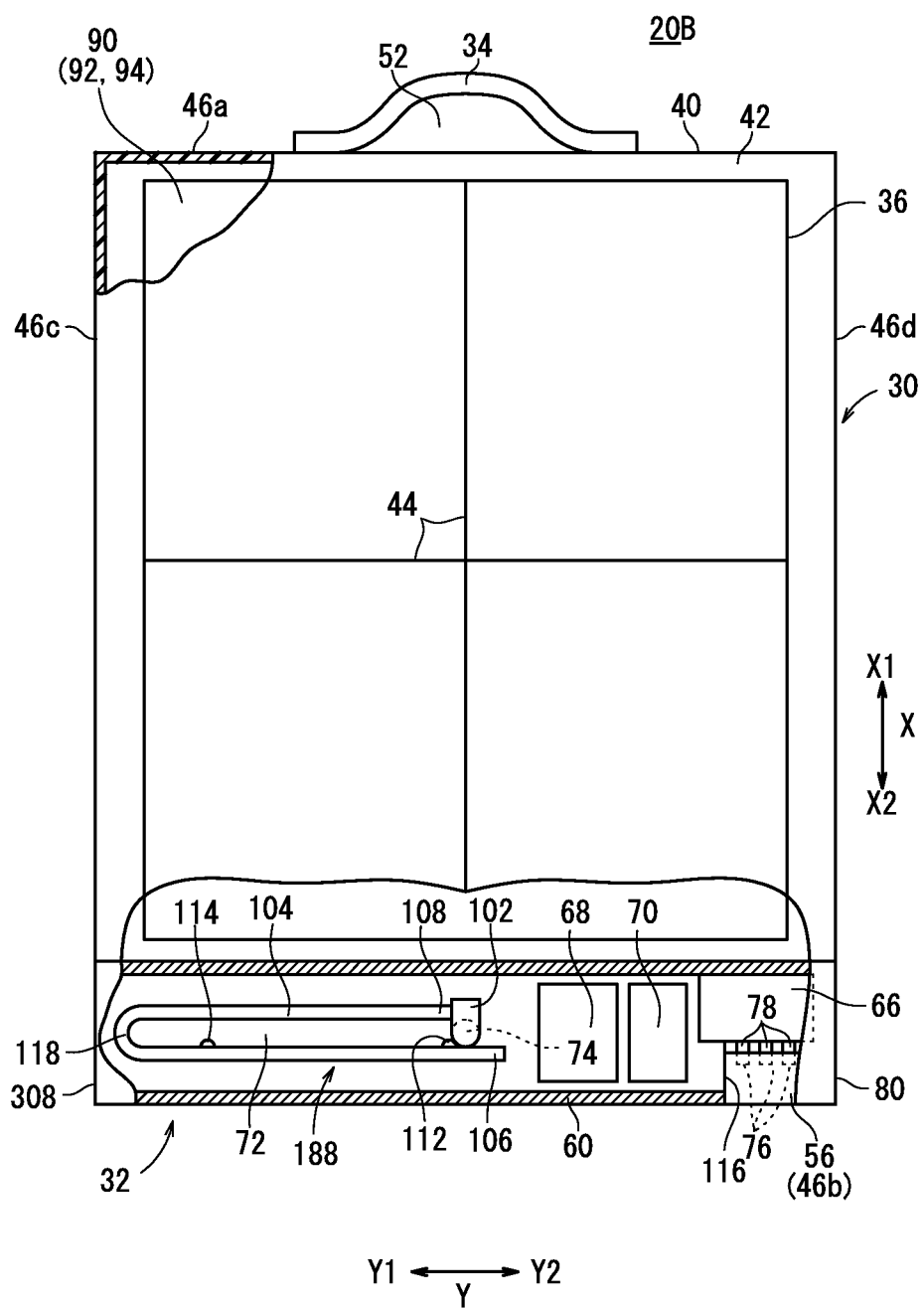
FIG. 32 is a plan view, partially cut away, of the cassette shown in FIG. 27.
Figure 33:
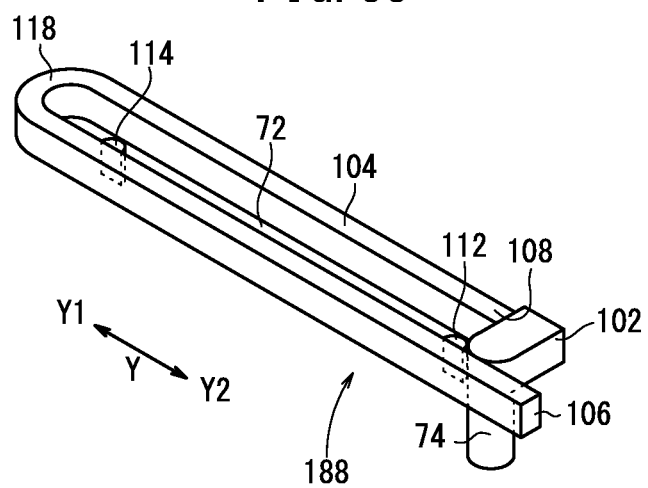
FIG. 33 is an enlarged perspective view of a shaft, a protrusion, a movement limiting member, and a convex member shown in FIG. 32.

A protrusion 102 is mounted on the distal end of the shaft 74, which is inserted through the hole 72 into the housing 60. The protrusion 102 extends in a radial direction of the shaft 74 (the direction of the arrow X1 in FIG. 32) and has a width that is substantially the same as the diameter of the cylindrical shaft 74. A movement limiting member 104, which is disposed on the bottom surface of the housing 60, substantially surrounds the hole 72 as viewed in plan in FIG. 32, and opens at the end of the hole 72 closer to the side surface 80. As shown in FIGS. 32 and 33, the movement limiting member 104 comprises a substantially U-shaped member, which extends along the outer peripheral edge of the hole 72.

The movement limiting member 104 has an end 106 positioned more closely to the side surface 80 than the shaft 74. The movement limiting member 104 extends from the end 106 along the outer peripheral edge of the hole 72 toward the side surface 308, and has a curved portion 118 at the end of the hole 72 that is closer to the side surface 308. The movement limiting member 104 further extends from the curved portion 118 along the outer peripheral edge of the hole 72 toward the side surface 80, and has another end 108, which is positioned more closely to the side surface 308 than the end 106, and which is held in abutment against the protrusion 102.

A semicylindrical tooth (stop member) 112 is disposed on the movement limiting member 104 in facing relation to the other end 108. Another tooth (stop member) 114, which essentially is identical in shape to the tooth 112, is disposed on the movement limiting member 104 in the vicinity of the curved portion 118.

The distance between the tooth 112 and the end of the hole 72 closer to the side surface 80 is set to a length that is substantially the same as the diameter of the shaft 74. The distance between the curved portion 118 and the tooth 114 is set to a length that is equal to the sum of the diameter of the shaft 74 and the length of the protrusion 102 (see FIG. 35B). The teeth 112, 114 preferably are in the form of elastic members made of rubber or the like.

Figure 34A:
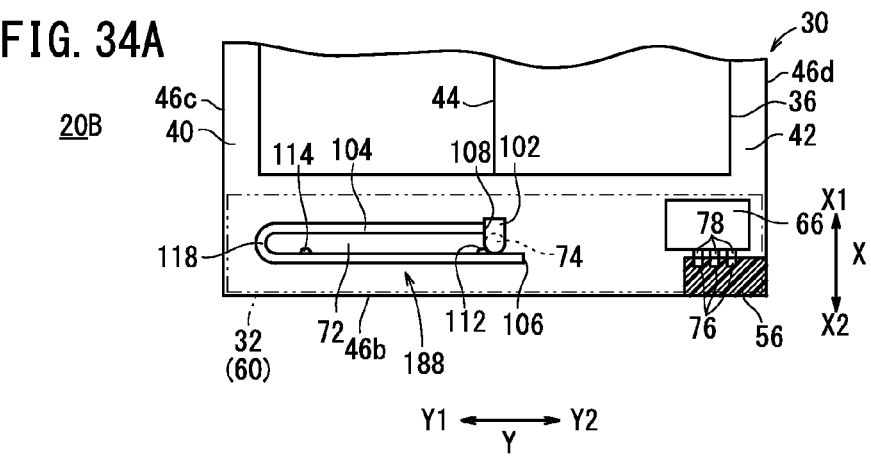
FIGS. 34A and 34B are plan views showing the manner in which a controller is turned with respect to a panel unit.

As shown in FIGS. 32 through 34B, if the housing 60 of the controller 32 is turned about the shaft 74 in a counterclockwise direction as viewed in plan in FIGS. 32 and 34A, the housing 60 is turned within an angular range that lies between the other end 108 and the end 106 of the movement limiting member 104. More specifically, if the angle of the housing 60 at the time that the other end 108 and the protrusion 102 are held in abutment with each other as shown in FIGS. 32 and 34A is 0°, then if the housing 60 is turned counterclockwise about the shaft 74, the housing 60 is turned between the other end 108 and the end 106, and is stopped against rotation at an angle of 90° (see FIG. 34B) where the protrusion 102 and the end 106 abut against each other. In other words, the angular range within which the housing 60 can be turned is limited by the movement limiting member 104 and the protrusion 102 to 90°.

As shown in FIGS. 34B through 35B, if the housing 60 is turned 90°, the protrusion 102 and the hole 72 are positioned along a straight line (guide line 44), which is directed toward the central position of the image capturing area 36.

Figure 34B:
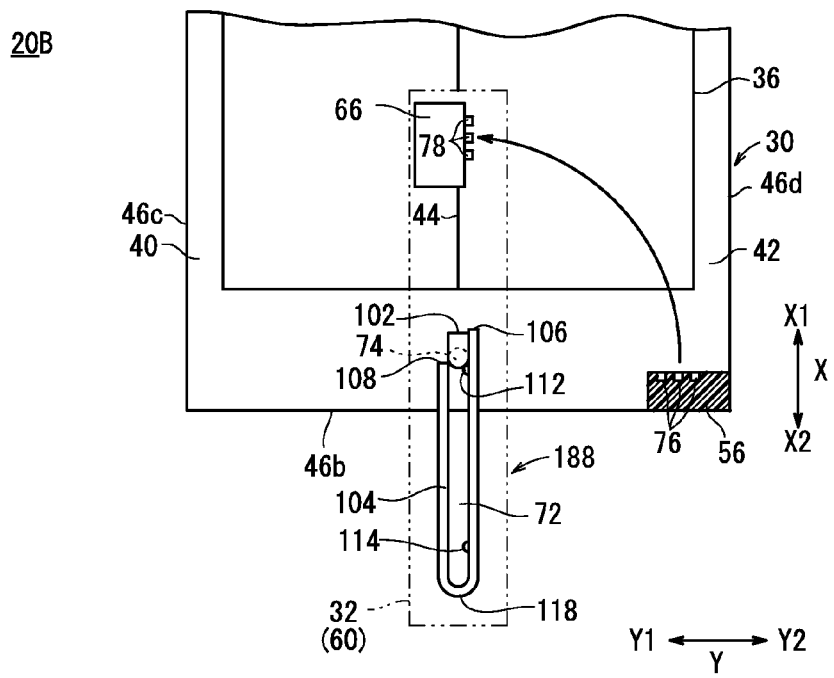

If the housing 60 is moved from the position shown in FIGS. 34B and 36A in the direction of the arrow X1, the tooth 112 abuts against the shaft 74. The tooth 112 is elastic, and the width of the protrusion 102 is substantially the same as the diameter of the shaft 74 that extends through the hole 72. The movement limiting member 104 surrounds the hole 72.

Therefore, the tooth 112 is compressed under the pressure from the shaft 74, and is displaced in unison with the movement limiting member 104 in the direction of the arrow X1. As a result, the housing 60 is moved linearly along the direction of the arrow X1 while being guided by the movement limiting member 104 and the protrusion 102.

Figure 35A:
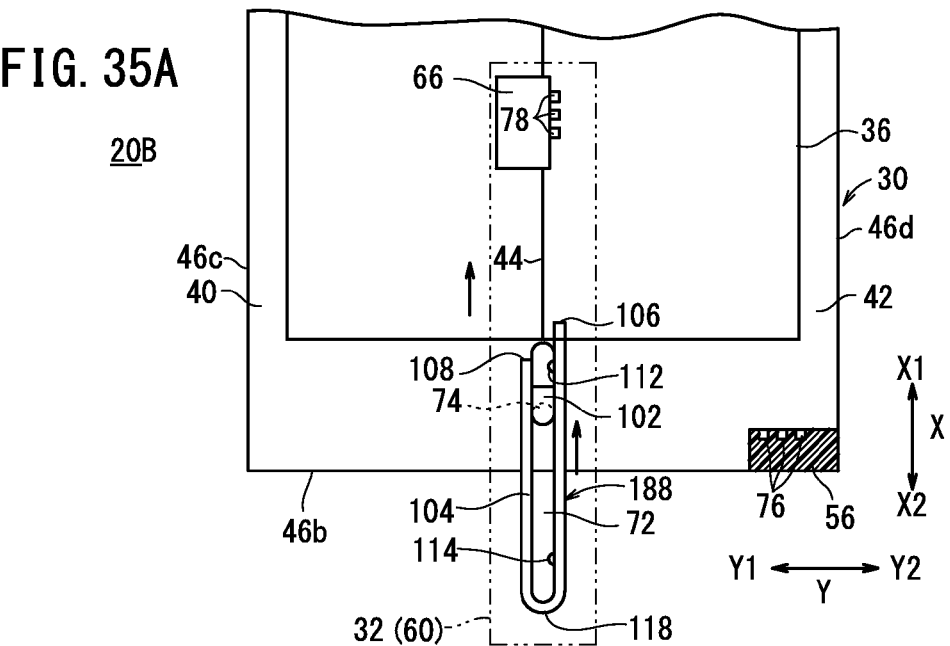
FIGS. 35A and 35B are plan views showing the manner in which the controller is translated with respect to the panel unit.
Figure 35B:
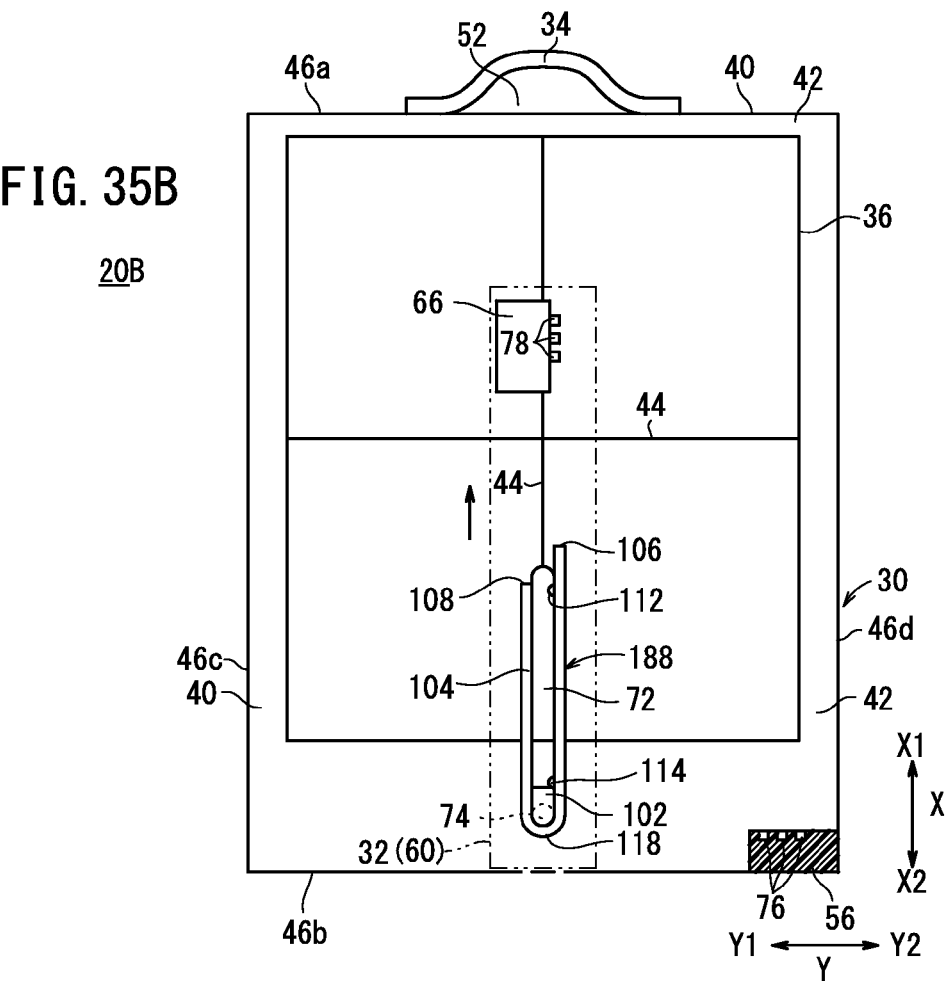

Since the tooth 114 also is elastic in the same manner as the tooth 112, if the tooth 114 abuts against the shaft 74, the tooth 114 is compressed under pressure from the shaft 74, and the tooth 114 is displaced in unison with the movement limiting member 104 in the direction of the arrow X1. As a result, as shown in FIG. 35B, the shaft 74 and the protrusion 102 are positioned between the tooth 114 and the curved portion 118, thereby making it possible to position the portion of the housing 60 near the side surface 80, substantially centrally within the image capturing area 36.

Therefore, the shaft 74, the protrusion 102, and the movement limiting member 104 jointly make up a moving mechanism 188 for turning the controller 32 with respect to the panel unit 30.

If the housing 60 is positioned as shown in FIGS. 28 through 32, and 34A (i.e., positioned on the side surface 46b), the connection terminals 76, 78 are held in contact with each other. If the housing 60 is positioned as shown in FIGS. 35B and 36B, or if the housing 60 is turned as shown in FIGS. 35A and 36A, the connection terminals 76, 78 are held out of contact with each other, thereby electrically disconnecting the controller 32 and the panel unit 30 from each other.

Figure 37A:
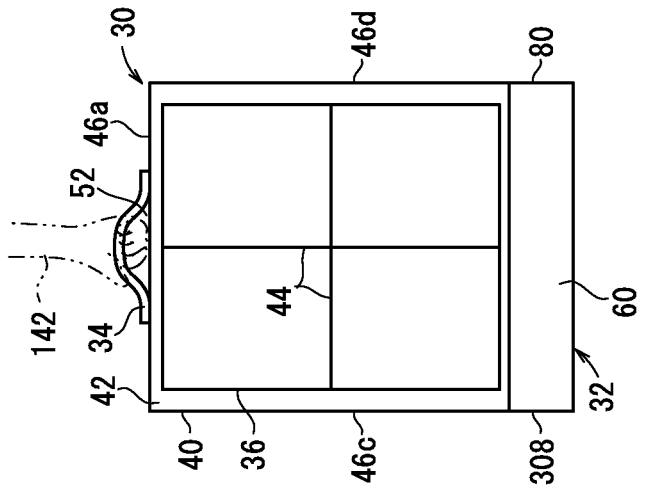
FIGS. 37A and 37B are plan views showing the manner in which the cassette is carried.
Figure 37B:
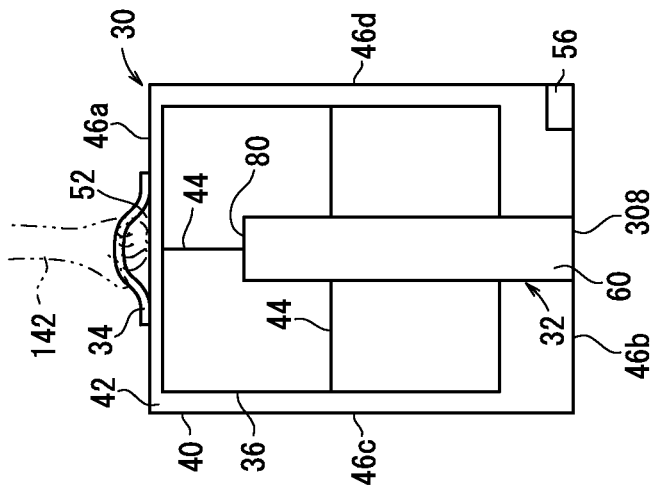

FIGS. 37A and 37B show the manner in which the electronic cassette 20B is carried by the user 142 such as a doctor or radiological technician.

In FIG. 37A, the portion of the controller 32 near the side surface 80 is disposed substantially centrally within the image capturing area 36, the side surface 308 is positioned so as to lie flush with the side surface 46b, and the grip 34 is placed in an uppermost position. Then, the user 142 grips the grip 34 and carries the electronic cassette 20B.

Among the components of the electronic cassette 20B, the power supply 68 (see FIGS. 29 and 32) is relatively heavy, so that the ratio of the weight of the controller 32 to the overall weight of the electronic cassette 20B is large. In the controller 32, the cassette controller 66, the power supply 68, and the communication unit 70 are centrally located in the housing 60 near the side surface 80. In FIGS. 27 through 32, the electronic cassette 20B is in an eccentric state in which the geometrically central position of the electronic cassette 20B (the central position of the image capturing area 36) and the center of gravity of the electronic cassette 20A (the position near the controller 32) do not coincide with each other, thereby making the entire electronic cassette 20B unbalanced in terms of the weight distribution thereof.

However, in FIG. 37A, since the portion of the housing 60 near the side surface 80, in which the cassette controller 66, the power supply 68, and the communication unit 70 are centrally located, is disposed in the central position of the image capturing area 36, the geometrically central position of the electronic cassette 20B and the center of gravity of the electronic cassette 20B coincide substantially with each other, thereby eliminating the eccentric state and making the entire electronic cassette 20B well balanced in terms of its weight distribution. As a result, the user 142 can carry the electronic cassette 20B in a stable manner.

In FIG. 37B, the controller 32 is disposed on the side surface 46b and in a lowermost position, and the grip 34 is disposed in an uppermost position. Then, the user 142 grips the grip 34 and carries the electronic cassette 20B.

In this case, the electronic cassette 20B also is in an eccentric state in which the geometrically central position thereof and the center of gravity thereof do not coincide with each other, thereby making the entire electronic cassette 20B unbalanced in terms of the weight distribution thereof. However, inasmuch as the user 142 carries the electronic cassette 20B with the controller 32 in a lowermost position, so as to lower the center of gravity of the electronic cassette 20B, the user 142 can carry the electronic cassette 20B stably even though the electronic cassette 20B has an unbalanced weight distribution.

According to the second embodiment, as shown in FIGS. 32 and 34A through 36B, inasmuch as the housing 60 can be positioned on the side surface 46b substantially centrally within the image capturing area 36, the user 142 can reliably carry the electronic cassette 20B, irrespective of whether the controller 32 is positioned with respect to the panel unit 30 in the position shown in FIG. 37A or in the position shown in FIG. 37B.

<Description of Operations of the Second Embodiment>

The radiographic image capturing system 10B, which incorporates the electronic cassette 20B according to the second embodiment, is basically constructed as described above. Operations of the radiographic image capturing system 10B will be described below with reference to the flowchart shown in FIG. 12.

The radiographic image capturing system 10B operates in the same manner as the radiographic image capturing system 10A, except for steps S1, S2, S8, and S9, which are changed in the following manner.

In step S1 shown in FIG. 12, the user 142, who may be a doctor or radiological technician, grips the grip 34 with the grip 34 in the uppermost position, and with the portion of the controller 32 near the side surface 80 being located substantially centrally in the image capturing area 36, and the side surface 308 of the controller 32 lying flush with the side surface 46b of the panel unit 30 (see FIG. 37A). The user 142 carries the electronic cassette 20B from a given storage location in the radiological department of the hospital to the image capturing base 12 (see FIG. 27). Since the connection terminal 76 and the connection terminal 78 are not held in contact with each other, the connected state detector 186 (see FIG. 11) detects that the connection terminal 76 and the connection terminal 78 are electrically disconnected from each other, and controls the power supply 68 to supply electric power only to the cassette controller 66. The electronic cassette 20B is placed in a sleep mode with only the cassette controller 66 operating.

In step S2, the user 142 places the electronic cassette 20B on the image capturing base 12 with the controller 32 and the irradiation surface 42 facing upwardly. Thereafter, the user 142 turns the housing 60 of the controller 32 from the substantially central position in the image capturing area 36 (see FIGS. 35B and 36B) to the position on the side surface 46b (see FIGS. 27 through 32 and 34).

In the case that the user 142 pushes the housing 60 of the controller 32 in the direction of the arrow X2, the tooth 114 abuts against the protrusion 102. Since the tooth 114 is elastic, the tooth 114 is compressed under pressure from the protrusion 102, and is displaced in unison with the movement limiting member 104 in the direction of the arrow X2. As a result, the housing 60 is moved with respect to the shaft 74 along the direction of the arrow X2 while being guided by the protrusion 102 and the movement limiting member 104.

If the user 142 further pushes the housing 60 in the direction of the arrow X2, the tooth 112 abuts against the protrusion 102. Since the tooth 112 also is elastic, the tooth 112 is compressed under pressure from the protrusion 102, and is displaced in unison with the movement limiting member 104 in the direction of the arrow X2. As a result, the shaft 74 and the protrusion 102 are positioned between the tooth 112 and the end of the hole 72 at the side surface 80. In other words, the housing 60 is positioned as shown in FIGS. 34B and 36A.

Upon the user 142 turning the housing 60 about the shaft 74 clockwise as viewed in plan in FIG. 34B, the end 106 become spaced away from the protrusion 102, whereas the other end 108 abuts against the protrusion 102. In other words, the housing 60 is turned 90° and positioned on the side surface 46b. As a consequence, the connection terminal 76 of the protrusion 56 and the connection terminal 78 in the recess 116 are brought into contact with each other.

At the time the connected state detector 186 detects that the connection terminal 76 and the connection terminal 78 are electrically connected to each other based on the contact between the connection terminal 76 and the connection terminal 78, the connected state detector 186 controls the power supply 68 to supply electric power to the communication unit 70 and the panel unit 30 in addition to the cassette controller 66. At this time, the power supply 68 starts to supply electric power to the communication unit 70 and the panel unit 30, whereupon the communication unit 70 becomes capable of sending signals to and receiving signals from the console 22 via a wireless communication link. Upon being supplied with electric power from the power supply 68, the driver circuit 98 of the panel unit 30 is activated. The biasing circuit 160 supplies a bias voltage to the pixels 150 to enable the pixels 150 to store electric charges therein. As a result, the electronic cassette 20B changes from the sleep mode into an active mode.

In step S8, the user 142 turns the housing 60 of the controller 32 from the present position on the side surface 46b (see FIGS. 27 through 32 and 34A) to the position substantially centrally in the image capturing area 36 (see FIGS. 35B and 36B).

More specifically, the user 142 turns the housing 60 about the shaft 74 counterclockwise as viewed in plan in FIGS. 34A and 34B. The other end 108 of the movement limiting member 104 is spaced away from the protrusion 102, and the end 106 thereof abuts against the protrusion 102. As a result, the housing 60 is turned 90° to the position shown in FIG. 34B, and the protrusion 102 and the hole 72 are placed on the guide line 44 toward the central position of the image capturing area 36.

Since the connection terminal 78 is spaced away from the connection terminal 76 if the housing 60 is turned counterclockwise, the connection terminal 76 and the connection terminal 78 are brought out of contact with each other, and hence become electrically disconnected from each other.

If the connected state detector 186 detects that the connection terminal 76 and the connection terminal 78 are electrically disconnected from each other, the connected state detector 186 controls the power supply 68 to supply electric power only to the cassette controller 66. The power supply 68 immediately stops supplying electric power to the communication unit 70 and the panel unit 30, and supplies electric power only to the cassette controller 66. As a result, the electronic cassette 20B changes from the active mode into the sleep mode in which only the cassette controller 66 is operable.

In the case that the user 142 pushes the housing 60 in the direction of the arrow X1, the tooth 112 abuts against the shaft 74. Since the tooth 112 is elastic, the tooth 112 is compressed under pressure from the shaft 74, and is displaced in unison with the movement limiting member 104 in the direction of the arrow X1. As a result, the housing 60 is moved linearly along the direction of the arrow X1 while being guided by the movement limiting member 104 and the protrusion 102.

In the case that the user 142 further pushes the housing 60 in the direction of the arrow X1, the tooth 114 abuts against the shaft 74. The tooth 114 is compressed under pressure from the shaft 74, and is displaced in unison with the movement limiting member 104 in the direction of the arrow X1. As a result, the shaft 74 and the protrusion 102 become positioned between the tooth 114 and the curved portion 118, thereby positioning the portion of the housing 60 near the side surface 80 substantially centrally in the image capturing area 36.

In step S9, the user 142 grips the grip 34 with the grip 34 in the uppermost position, and with the controller 32 positioned substantially centrally in the image capturing area 36, and the side surface 308 of the controller 32 lying flush with the side surface 46b of the panel unit 30. The user 142 carries the electronic cassette 20B to a given storage location in the radiological department of the hospital.

If the user 142 carries the electronic cassette 20B as shown in FIG. 37B in steps S1 and S9, then the operations in steps S2 and S8 are dispensed with.

<Description of Advantages of the Second Embodiment>

As described above, the electronic cassette 20B according to the second embodiment can have the center of gravity thereof changed easily by turning the controller 32, which is responsible for unbalanced weight distribution, with respect to the panel unit 30, using the moving mechanism 188, which includes the shaft 74, the protrusion 102, and the movement limiting member 104.

According to the second embodiment, the controller 32 is turned with respect to the panel unit 30 to bring the central position and the center of gravity into substantial agreement with each other, thereby easily eliminating any unbalanced weight distribution.

More specifically, after the housing 60 of the controller 32 on the side surface 80 is turned with respect to the panel unit 30 to a substantially central position in the image capturing area 36 as shown in FIGS. 35B and 36B, using the shaft 74, the protrusion 102, and the movement limiting member 104, the user 142 carries the electronic cassette 20B with the grip 34 in an uppermost position, as shown in FIG. 37A. Since the cassette controller 66, the power supply 68, and the communication unit 70 are located centrally in the housing 60 near the side surface 80, the center of gravity is brought close to the central position by positioning the portion of the housing 60 near the side surface 80 thereof substantially centrally within the image capturing area 36.

Inasmuch as the electronic cassette 20B feels light upon being carried by the user 142, the user 142 can carry the electronic cassette 20B stably and easily. As a result, the user 142 can carry the electronic cassette 20B without dropping the electronic cassette 20B or causing the controller 32 to hit other objects. The user 142 experiences a reduced burden upon carrying the electronic cassette 20B.

According to the second embodiment, as described above, since any unbalanced weight distribution of the electronic cassette 20B is easily eliminated by turning the controller 32 with respect to the panel unit 30 using the moving mechanism 188, the user 142 can carry the electronic cassette 20B in a stable manner.

As the controller 32 is turned about the shaft 74, the controller 32 is turned with respect to the panel unit 30 by a simple mechanism. Even though the controller 32 may be disposed over the image capturing area 36 while the electronic cassette 20B is being carried, the controller 32 can be retracted away from the image capturing area 36 during the image capturing process. Therefore, the controller 32 and the shaft 74 do not present an obstacle to capturing of radiographic images.

The controller 32 is turned about the shaft 74 with respect to the panel unit 30, and is moved along the oblong hole 72 with respect to the panel unit 30. Consequently, the central position and the center of gravity referred to above can easily be brought into agreement with each other, thereby reliably eliminating the unbalanced weight distribution.

The shaft 74 is disposed in a location outside of the image capturing area 36 of the irradiation surface 42, and the oblong hole 72 is defined in the bottom surface of the housing 60 of the controller 32 near the irradiation surface 42 along the longitudinal direction of the housing 60. Therefore, the controller 32 can be moved stably and reliably along the longitudinal direction.

The other end 108, the end 106 of the opening of the movement limiting member 104, and the protrusion 102 jointly define an angular range of the controller 32 with respect to the shaft 74. The movement limiting member 104, the distal end of the shaft 74, and the protrusion 102 jointly set the direction along which the controller 32 is moved with respect to the shaft 74. The distance that the controller 32 moves along the direction (direction along the hole 72) is determined depending on the length of the oblong hole 72. Due to the movement limiting member 104 and the protrusion 102, it is possible to turn the controller 32 with respect to the panel unit 30 accurately and with high precision.

Since the teeth 112, 114 are provided in the hole 72 of the movement limiting member 104 for stopping the controller 32 from moving along the hole 72 by coming into contact with the protrusion 102, the controller 32 can reliably be stopped at any desired position with respect to the panel unit 30.

If the controller 32 is turned, the power supply 68 stops supplying electric power to the communication unit 70 and the panel unit 30. Therefore, wasteful electric power consumption is minimized.

More specifically, if the controller 32 is turned, the connection terminal 76 and the connection terminal 78 are brought out of contact with each other, thereby electrically disconnecting the panel unit 30 and the controller 32 from each other. At this time, the power supply 68 stops supplying electric power to the communication unit 70 and the panel unit 30 in order to reliably minimize wasteful electric power consumption.

The connected state detector 186 detects whether or not the connection terminals 76, 78 are electrically connected to each other, and therefore, the connected state detector 186 can easily grasp the timing at which to control the panel unit 30, as well as the timing at which radiographic images are read from the radiation conversion panel 92. The connected state detector 186 indicates the detection result to the power supply 68, so as to enable the power supply 68 to supply electric power efficiently.

According to the second embodiment, as described above, since the controller 32 can be turned using the moving mechanism 188, which includes the shaft 74, the protrusion 102, and the movement limiting member 104, after the controller 32 has been moved to the position shown in FIGS. 27 through 32 and 34A with respect to the panel unit 30, the user 142 can carry the electronic cassette 20B with the grip 34 in an uppermost position and with the controller 32 in a lowermost position, as shown in FIG. 37B.

Even though the electronic cassette 20B has an unbalanced weight distribution, the same advantages as those discussed in relation to FIG. 9A can be achieved upon the user 142 carrying the electronic cassette 20B with the center of gravity thereof made low.

According to the second embodiment, similar to the first embodiment, it has been described that the housing 60 of the controller 32, which is thicker than the housing 40 of the panel unit 30, is disposed on the housing 40. However, the second embodiment is not limited to such a description. Alternatively, the controller 32 may be disposed so as to protrude from the housing 40, insofar as the controller 32 can be turned with respect to the panel unit 30.

According to the second embodiment, similar to the first embodiment, the controller 32 may be disposed in a location outside of an area of the panel unit 30 that is irradiated with radiation 16 having passed through the subject 14. In such a case, the console 22 trims a portion of the radiographic image acquired from the electronic cassette 20B, which corresponds to the area irradiated with radiation 16, thereby obtaining a desired image corresponding to the irradiated area.

<Description of Modifications of the Second Embodiment>

The electronic cassette 20B according to the second embodiment is not limited to the above description, but may be implemented according to the embodiments shown in FIGS. 38 through 51.

FIG. 38 is a perspective view showing a process of charging the power supply 68 with a cradle 190. The electronic cassette 20B and the cradle 190 are electrically connected to each other by the USB cable 192 having the connectors 194, 196, thereby achieving the same advantages as those discussed in relation to FIG. 13.

FIG. 39A shows the housing 60 of the controller 32, which is covered entirely with the cushioning member 200. FIG. 39B shows the housing 60, the side surface 308 of which is covered with the cushioning member 202.

If the user 142 carries the electronic cassette 20B with the controller 32 being disposed with respect to the panel unit 30 as shown in FIG. 37B, the side surface 308 of the housing 60 of the controller 32 is disposed in a lowermost position on the electronic cassette 20B. The housing 60 of the controller 32 is covered entirely by the cushioning member 200, or partially by the cushioning member 202, so that the controller 32 is effectively protected from impacts if the electronic cassette 20B is dropped or if the controller 32 hits against other objects, similar to the case of the modifications shown in FIGS. 14A and 14B.

FIGS. 40A through 42B show grips that are disposed in locations other than the side surface 46a.

In FIG. 40A, in addition to the grip 34, a grip 290 is disposed on the upper surface of the housing 60 of the controller 32.

After the controller 32 has been placed in the position shown in FIG. 40A with respect to the panel unit 30, for example, the user 142 may grip the grip 290, which is held in an uppermost position, and carry the electronic cassette 20B. Similar to the case of the modification shown in FIG. 20A, the user 142 can carry the electronic cassette 20B with a well-balanced weight distribution. Since the user 142 directly grips the heavy controller 32 through the grip 290, the electronic cassette 20B feels light to the user 142, and the user 142 can carry the electronic cassette 20B easily and in a stable manner.

For turning the controller 32 with respect to the panel unit 30, the user 142 may do so by gripping the grip 290, and hence the user 142 can turn the controller 32 easily.

With the structure shown in FIG. 40A, therefore, the grip 290 allows the user 142 to feel comfortable in handling the electronic cassette 20B upon carrying the same and turning the controller 32.

The structure shown in FIG. 40B differs from the structure shown in FIG. 40A, in that the foldable grip 300 is disposed on an upper surface of the housing 60.

The structure shown in FIG. 40B provides the same advantages as offered by the structure shown in FIG. 40A. In addition, since the user 142 can pull out the grip 300 only when the electronic cassette 20B is carried or if the controller 32 is to be turned, the grip 300 does not present an obstacle to capturing of radiographic images, similar to the case of the structure shown in FIG. 20B. Therefore, the user 142 finds it easier to handle the electronic cassette 20B.

Figure 41A:
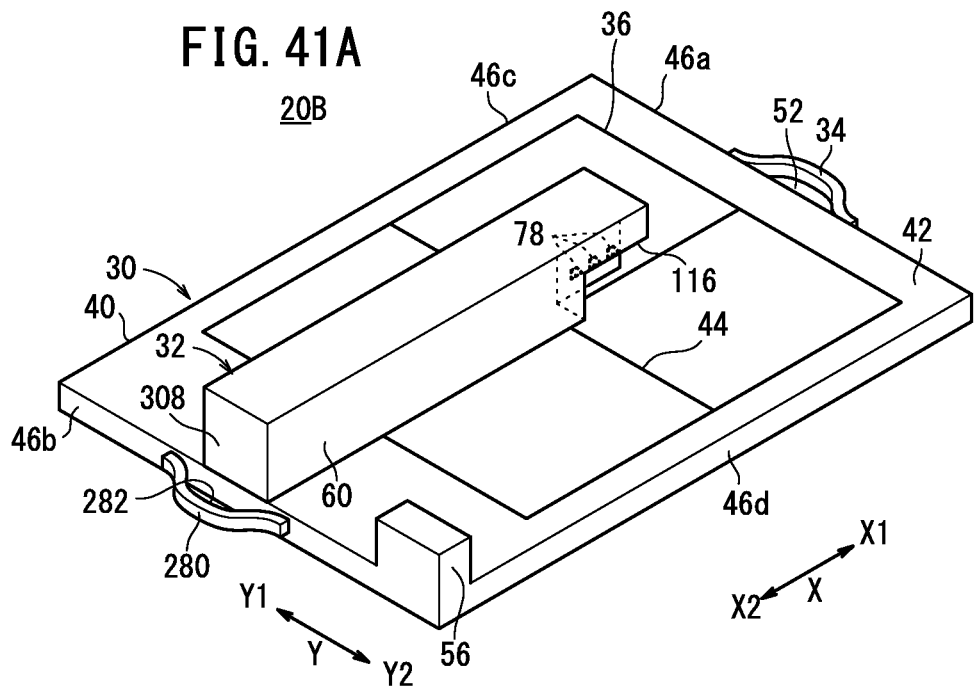
FIGS. 41A and 41B are perspective views of cassettes, which include two grips provided on panel units.

In FIG. 41A, similar to FIG. 19A, in addition to the grip 34, a grip 280 is disposed on the side surface 46b.

After having turned the controller 32 to the position shown in FIG. 41A with respect to the panel unit 30, for example, the user 142 may carry the electronic cassette 20B by gripping the grip 34 with one hand and gripping the grip 280 with the other hand. The structure shown in FIG. 41A provides the same advantages as those of the structure shown in FIG. 19A.

Figure 41B:
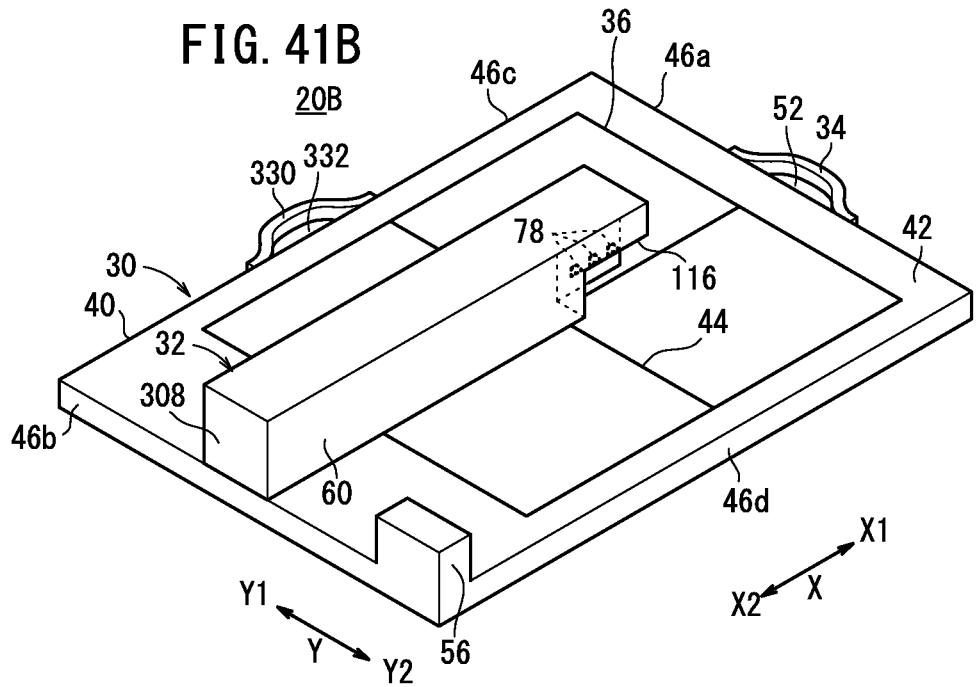

In FIG. 41B, in addition to the grip 34, a grip 330 is disposed on the side surface 46c.

After having turned the controller 32 to the position shown in FIG. 41B with respect to the panel unit 30, for example, the user 142 may carry the electronic cassette 20B by gripping the grip 330 held in an uppermost position. The structure shown in FIG. 41B provides the same advantages as those of the structure shown in FIG. 19B.

The structure shown in FIG. 42A differs from the structure shown in FIG. 40A, in that the grip 310 is disposed on the side surface 308 of the housing 60.

The structure shown in FIG. 42B differs from the structure shown in FIG. 40B, in that the foldable grip 320 is disposed on the side surface 308 of the housing 60.

The structures shown in FIGS. 42A and 42B provide the same advantages as those of the structures shown in FIGS. 40A and 40B.

Figure 43A:
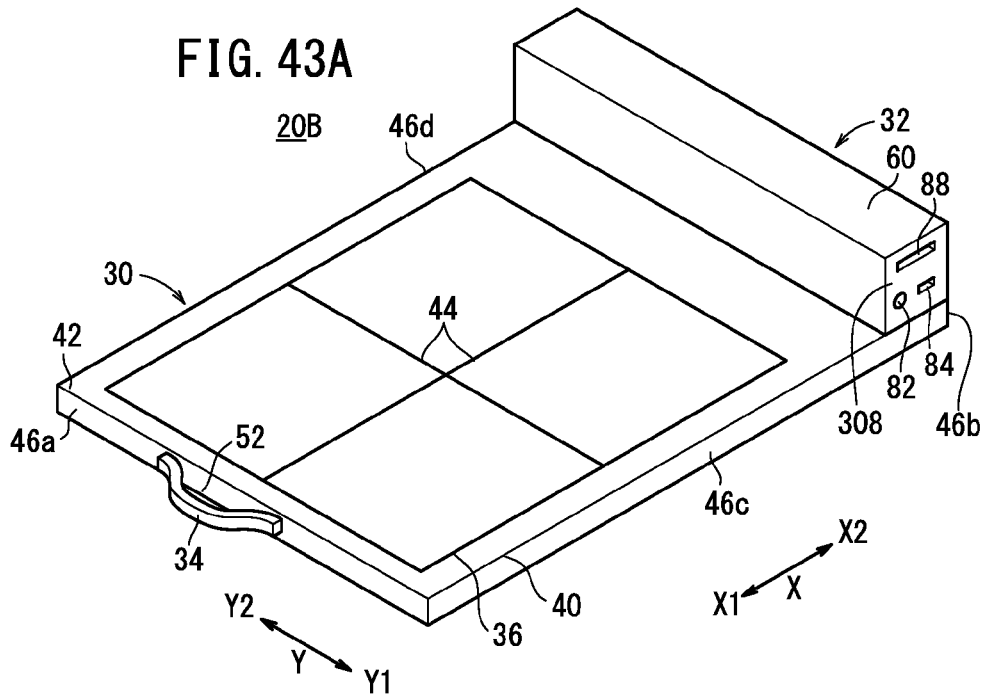
FIGS. 43A and 43B are perspective views of cassettes, which include grips provided respectively on controllers and panel units.
Figure 43B:
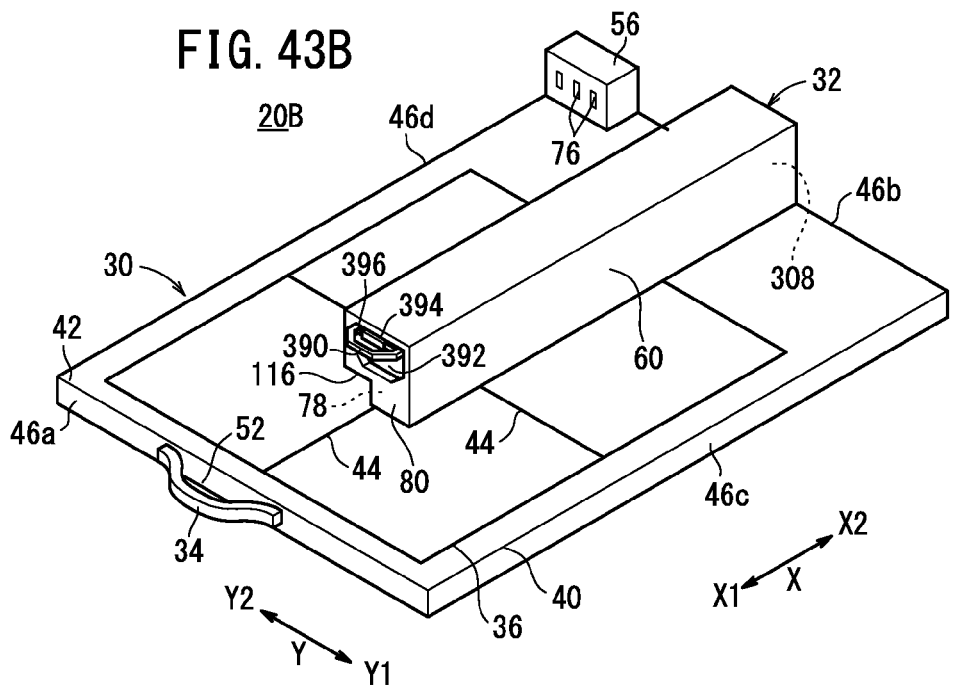

FIGS. 43A and 43B show the input terminal 82, the USB terminal 84, and the card slot 88, which are provided on the side surface 308 of the housing 60, together with a foldable grip 390, which is provided on the side surface 80.

The side surface 80 has a substantially hexagonal recess 392 defined therein, and the grip 300 has opposite ends disposed in the recess 392. The recess 392 houses a rectangular support 394 therein. Opposite ends of a shaft 396, which extends through the support 394, are coupled to respective opposite ends of the grip 390.

The structures shown in FIGS. 43A and 43B provide the same advantages as those of the structures shown in FIGS. 40B and 42B. The structures shown in FIGS. 43A and 43B may or may not include the grip 34.

FIG. 44 shows a structure which differs from the structures shown in FIGS. 43A and 43B, in that the input terminal 82, the USB terminal 84, and the card slot 88 are provided on the side surface 308 of the housing 60, and a grip 400 is provided on the side surface 80. The grip 400 includes a handle that cooperates with the side surface 80 of the housing 60 in defining a hole 402 therebetween, which is large enough for a hand of the user 142 to be placed therein.

The structure shown in FIG. 44 provides the same advantages as those of the structures shown in FIGS. 40A and 42A. The structure shown in FIG. 44 may or may not include the grip 34.

FIGS. 45A through 47 show other arrangements of the moving mechanism 188.

In FIGS. 45A through 47, the moving mechanism 188 includes a shaft 348, which is vertically mounted on the irradiation surface 42 near the side surface 308 of the housing 60, a hole 350 defined in the bottom surface of the housing 60 near the side surface 308 with the shaft 348 extending through the hole 350, a protrusion 352, which extends through the hole 350 and extends in a radial direction of the shaft 348 from a distal end of the shaft 348 that is inserted in the housing 60, and a substantially arcuate rotation limiting member 354, which substantially surrounds the hole 350 as viewed in plan and which is partially open.

The protrusion 352 has a width that is substantially the same as the diameter of the shaft 348. The opening of the rotation limiting member 354 is defined between one end 356 and another end 358 thereof, which abut against side surfaces of the protrusion 352 if the housing 60 is turned about the shaft 348. The housing 60 can be turned about the shaft 348 within an angular range, which is represented by the angle (90°) defined between the one end 356 and the other end 358.

As shown in FIGS. 45A through 47, the moving mechanism 188 only turns the housing 60 about the shaft 348, and does not move the housing 60 along the directions of the arrow X.

Figure 45A:
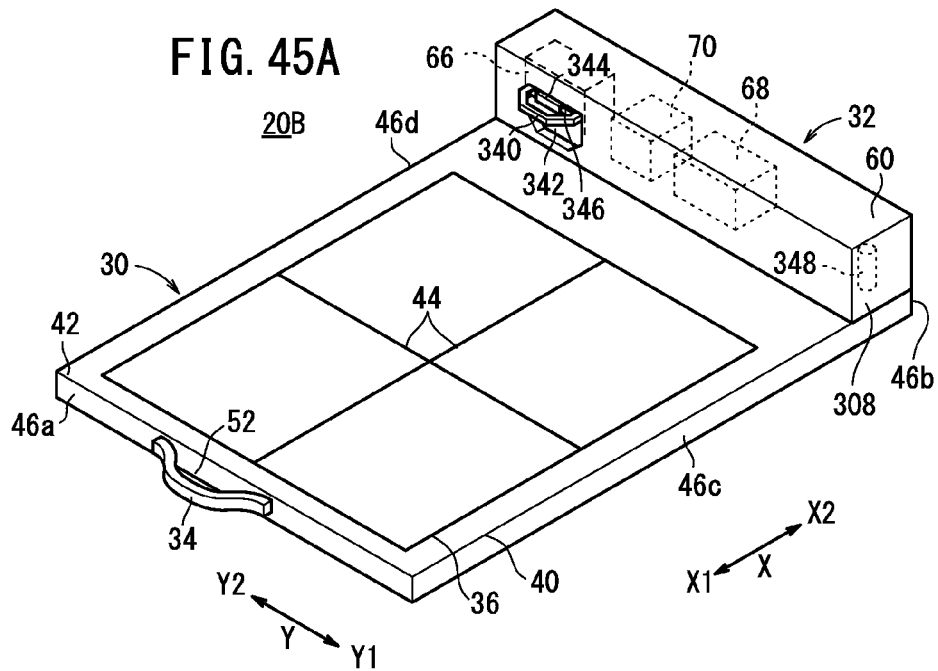
FIGS. 45A and 45B are perspective views showing the manner in which a controller is turned with respect to a panel unit.
Figure 45B:
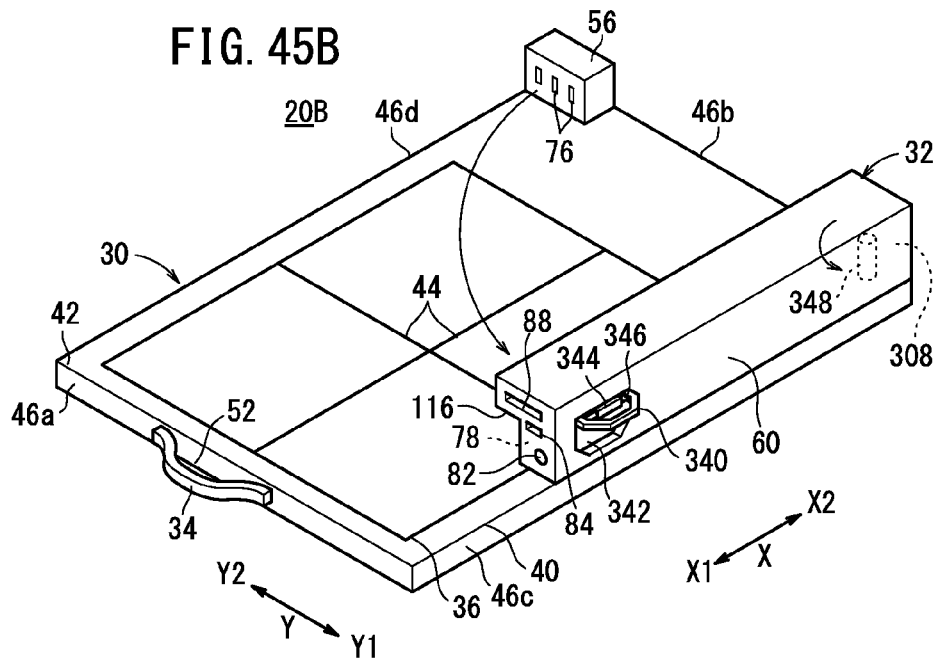
Figure 46A:
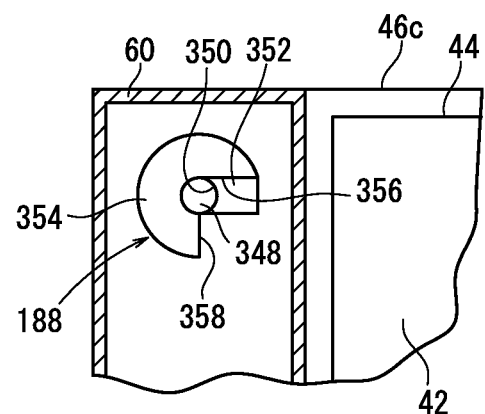
FIGS. 46A and 46B are enlarged plan views of a shaft, a protrusion, and a movement limiting member shown in FIGS. 45A and 45B.
Figure 46B:
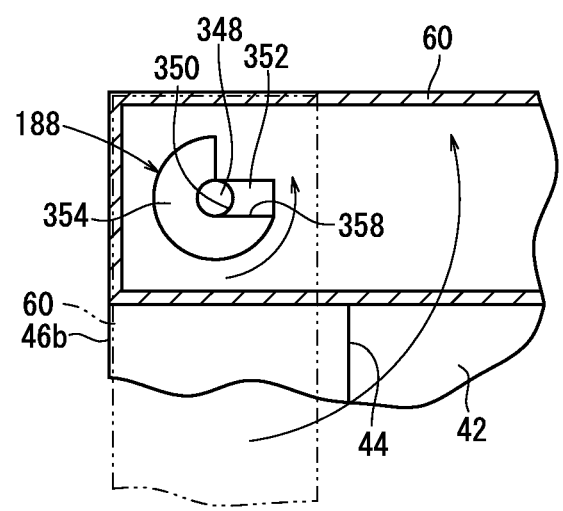

For turning the housing 60 from the position on the side surface 46b, as shown in FIG. 45A, to the position on the side surface 46c, as shown in FIG. 45B, the user 142 turns the housing 60 counterclockwise about the shaft 348 by 90°, as shown in FIGS. 46A and 46B. The end 356 of the rotating limiting member 354 is spaced away from the protrusion 352, whereas the other end 358 of the rotating limiting member 354 abuts against the protrusion 352, thereby positioning the housing 60 at the side surface 46c. At this time, the connection terminal 76 and the connection terminal 78 are taken out of contact with each other and become electrically disconnected.

Since the controller 32 is turned about the shaft 348 as shown in FIGS. 45A through 47, it is possible to bring the center of gravity close to the central position, for thereby minimizing the unbalanced weight distribution.

The shaft 348 is disposed in a location on the irradiation surface 42 that lies outside of the image capturing area 36 (a location near the side surface 308). The hole 350 through which the shaft 348 extends is defined in a bottom surface of the housing 60 near the irradiation surface 42. Therefore, the controller 32 can be turned more stably and reliably.

The one end 356 and the other end 358, which define the opening of the rotation limiting member 354, and the protrusion 352 cooperate to define an angular range within which the controller 32 can be turned about the shaft 348. Therefore, the controller 32 can be turned accurately and with good precision with respect to the panel unit 30.

As shown in FIGS. 45A and 45B, a foldable grip 340 is mounted on a side surface of the housing 60. The side surface of the housing 60 has a substantially hexagonal recess 342 defined therein, and opposite ends of the grip 340 are disposed in the recess 342. The recess 342 houses a rectangular support 344 therein, and a shaft 346, which extends through the support 344, has opposite ends coupled to the respective opposite ends of the grip 340.

In the case that the user 142 does not grip the grip 340, the grip 340 is placed in the recess 342. If the user 142 intends to grip the grip 340 (i.e., to turn the housing 60 about the shaft 348), the user 142 turns the central portion of the grip 340 about the shaft 346, pulls the grip 340 out of the recess 342, and grips the grip 340. If the user 142 intends to place the grip 340 back into the recess 342, the user 142 turns the central portion of the grip 340 about the shaft 346 so that the grip 340 is accommodated in the recess 342. This arrangement offers the same advantages as those of the structures shown in FIGS. 40B and 42B.

If the grip 330 is disposed on the side surface 46c as shown in FIG. 47, then the resultant structure offers the same advantages as those of the structure shown in FIG. 41B.

The electronic cassette 20B according to the second embodiment may also employ the arrangements shown in FIGS. 48 through 51.

Figure 48:
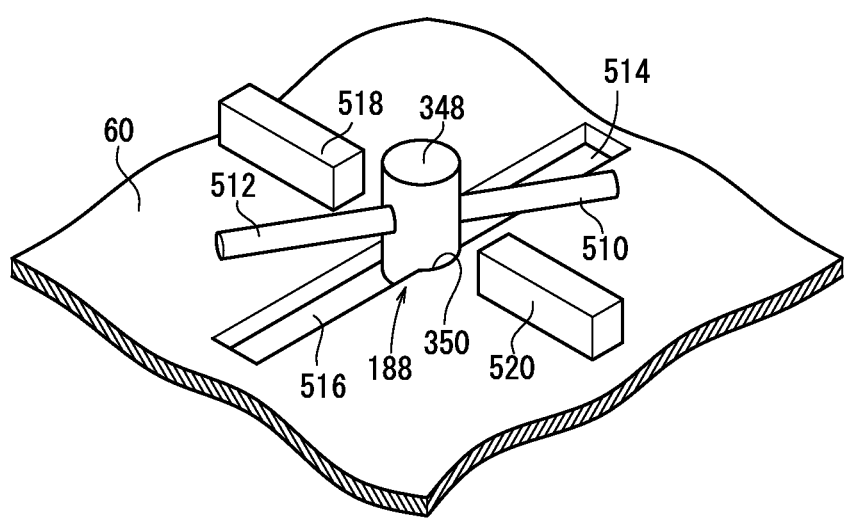
FIG. 48 is an enlarged perspective view of a shaft, a protrusion, and a movement limiting member of a cassette.

FIG. 48 shows another arrangement of the moving mechanism 188.

Unlike the arrangements shown in FIGS. 45A through 47, the moving mechanism 188 shown in FIG. 48 includes two cylindrical arms 510, 512 that extend radially in opposite directions from a distal end of the shaft 348, which is inserted through the hole 350 into the housing 60. The moving mechanism 188 also includes rotation limiting members 518, 520, which are disposed on the bottom surface of the housing 60, as substantially rectangular blocks along radial directions of the shaft 348.

As shown in FIG. 48, slots 514, 516 are defined in the bottom surface of the housing 60 at angular positions located between the angular positions of the rotation limiting members 518, 520 and the angular positions of the arms 510, 512. The slots 514, 516 have a size large enough for the respective arms 510, 512 to pass therethrough, and the slots 514, 516 are held in communication with the hole 350.

In the case that the housing 60 is turned about the shaft 348, if the rotation limiting members 518, 520 are turned by 90° in unison with the housing 60, then the rotation limiting members 518, 520 are brought into abutment against the arms 510, 512, respectively. In a case where the housing 60 is turned about the shaft 348 and the rotation limiting members 518, 520 are aligned respectively with the slots 514, 516, if the user 142 lifts the housing 60, the rotation limiting members 518, 520 pass through the slots 514, 516, respectively. Therefore, the user 142 can easily remove the controller 32 from the panel unit 30. Consequently, in addition to the advantages of the structures shown in FIGS. 45A through 47, the structure shown in FIG. 48 offers another advantage in that the electronic cassette 20B can easily be serviced for maintenance or replacement of parts.

The electronic cassette 20B, which includes the hole 72 and the shaft 74, provides the above advantage as a result of having the rotation limiting members 518, 520 and the slots 514, 516.

Figure 29:
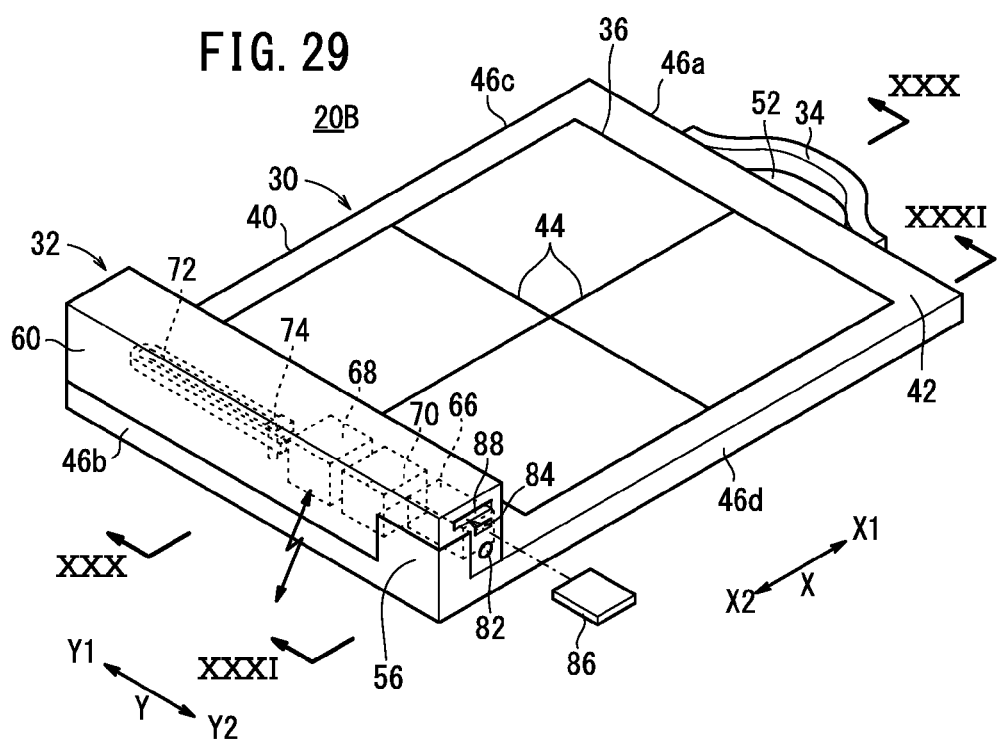
FIG. 29 is a perspective view of the cassette shown in FIG. 27.
Figure 30:
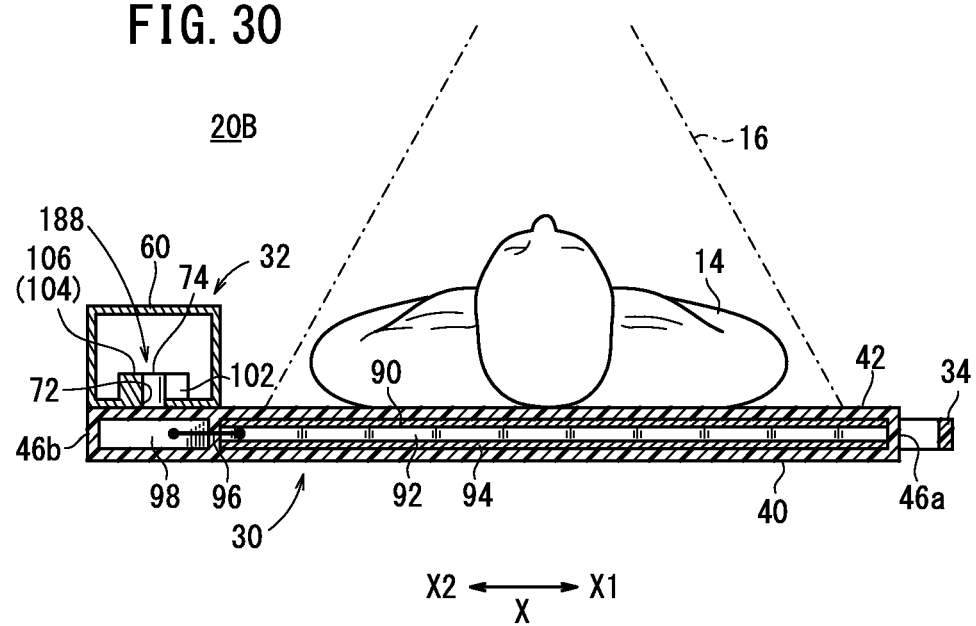
FIG. 30 is a cross-sectional view taken along line XXX-XXX of FIG. 29.

FIGS. 49A through 50B show an electronic cassette 20B that differs from the electronic cassette 20B shown in FIGS. 29 and 32, in that the shaft 74 is disposed at a corner of the panel unit 30, which faces in the direction of the arrow Y1 and the direction of the arrow X2 (the position where the shaft 348 is disposed).

Figure 49A:
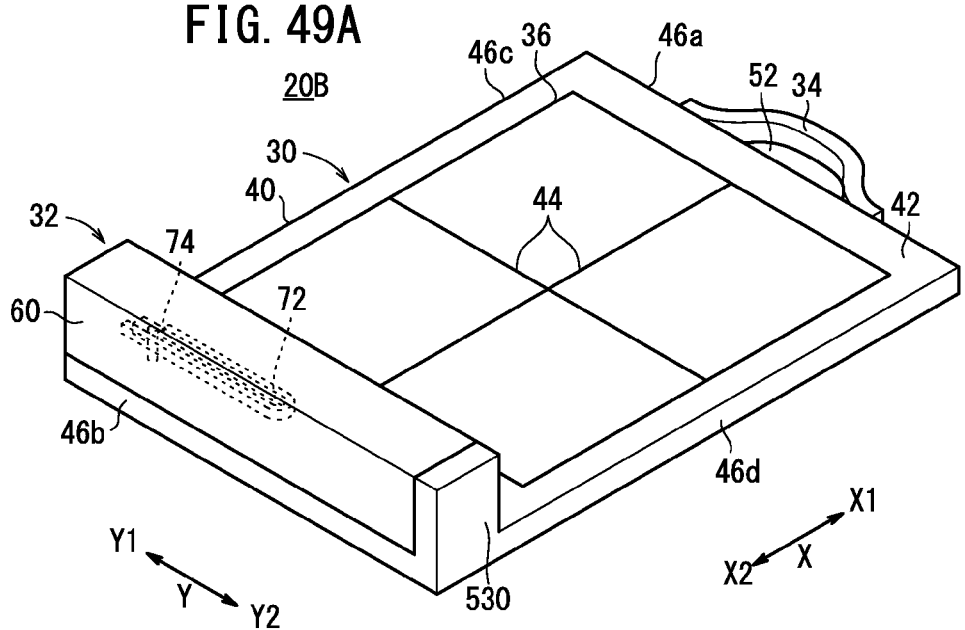
FIG. 49A is a perspective view of a cassette with a shaft disposed in a position different from the positions shown in FIGS. 29 and 32.

In FIG. 49A, the panel unit 30 has a block 530, which is thin along the directions of the arrow Y. The hole 72 in the housing 60 is defined laterally inversely along the directions of the arrow Y, in comparison to the electronic cassette 20B shown in FIGS. 29 and 32. Therefore, the curved portion 118 is disposed substantially centrally in the housing 60. The input terminal 82, the USB terminal 84, and the card slot 88 are disposed on the side surface 308, whereas the connection terminal 78 is disposed on the side surface 80.

Figure 49B:
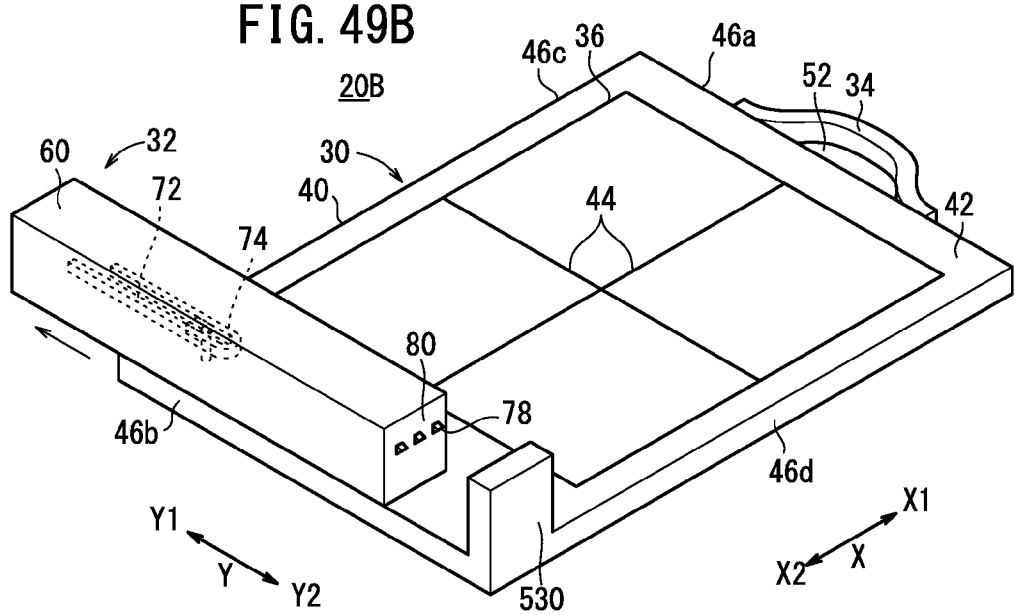
FIG. 49B is a perspective view showing the manner in which a controller is moved with respect to a panel unit of the cassette shown in FIG. 49A.

If the controller 32 is disposed in the position shown in FIG. 49A (i.e., the position on the side surface 46b), then if the user 142 pushes the housing 60 in the direction of the arrow Y1, the housing 60 is moved to the position shown in FIG. 49B along the direction of the arrow Y1 while being guided by the hole 72 and the shaft 74. The connection terminal 76 on the block 530 and the connection terminal 78 on the side surface 80 are brought out of contact with each other, and hence become electrically disconnected.

Figure 50A:
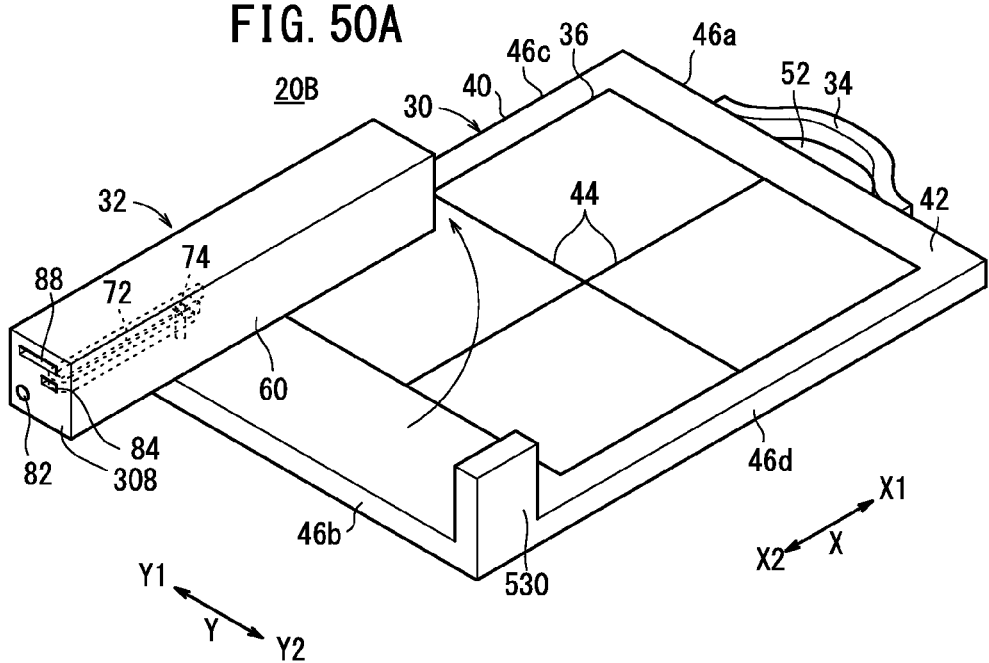
FIG. 50A is a perspective view showing the manner in which the controller is turned with respect to the panel unit of the cassette shown in FIG. 49B.
Figure 50B:
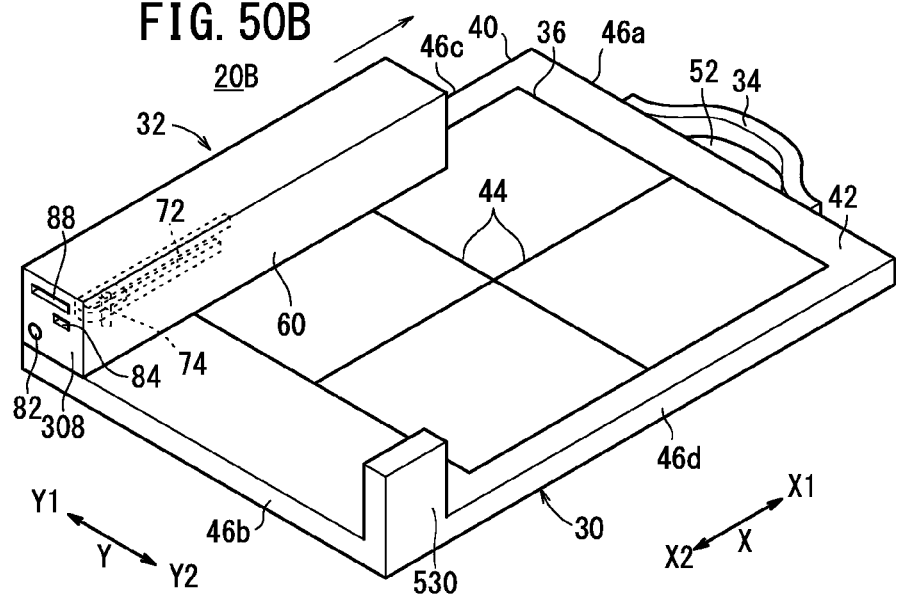
FIG. 50B is a perspective view showing the manner in which the controller is moved with respect to the panel unit after being turned as shown in FIG. 50A.

Then, as viewed in FIG. 26B, the user 142 turns the housing 60 counterclockwise about the shaft 74. The housing 60 is turned 90° and is disposed along the side surface 46c, as shown in FIG. 50A. If the user 142 pushes the housing 60 in the direction of the arrow X1, the housing 60 is moved to the position shown in FIG. 50B along the direction of the arrow X1 while being guided by the hole 72 and the shaft 74. As a result, the housing 60 is positioned on the side surface 46c, and the side surface 80 of the housing 60 is positioned in the vicinity of the geometrically central position of the electronic cassette 20B.

The electronic cassette 20B shown in FIGS. 49A through 50B offers the same advantages as those of the structures shown in FIGS. 45A through 47.

According to the second embodiment, as shown in FIG. 51, if a double-sided image capturing electronic cassette 20B is employed, then the subject 14 may be imaged after the electronic cassette 20B has been turned upside down and placed on the image capturing base 12. Such a modification offers the same advantages as those of the structures shown in FIG. 24 and according to the second embodiment.

The second invention is not limited to the above embodiment, but various alternative arrangements may be adopted without departing from the scope of the second invention.

For example, if a scintillator 608 made of CsI is used in the second embodiment, then, similar to the case of the first embodiment, the grips 290, 300, 310, 320, 340, 390, 400 (see FIGS. 40A, 40B, 42A, 42B, 43B, and 44 through 45B) may be made of a material having a high coefficient of thermal conductivity and used as a heat radiating member for radiating the heat generated by the controller 32. A wavy or rectangular member, which functions as a heat sink, may be mounted on the grips 290, 300, 310, 320, 340, 390, 400 for increasing the heat radiating area. Since the grips 290, 300, 310, 320, 340, 390, 400 are mounted directly on the housing 60 of the controller 32, the grips 290, 300, 310, 320, 340, 390, 400 can directly radiate heat generated by the controller 32. Furthermore, inasmuch as the grips 290, 300, 310, 320, 340, 390, 400 are gripped by the user 142, the grips 290, 300, 310, 320, 340, 390, 400 must be capable of radiating heat in a manner that does not cause the user 142 to suffer a low temperature burn.

The housing 60 of the controller 32 houses therein components that generate a large amount of heat, such as the power supply 68, etc. Therefore, the components that generate a large amount of heat may be positioned in the housing 60 near the grips 290, 300, 310, 320, 340, 390, 400 for efficiently radiating heat generated by the controller 32 through the grips 290, 300, 310, 320, 340, 390, 400.

3. Description of Third Embodiment:

A radiographic image capturing apparatus according to a preferred embodiment of a third invention (third embodiment) will be described in detail below with reference to FIGS. 52 through 60.

<Description of Arrangement of the Third Embodiment>

A radiographic image capturing system 10C incorporates therein an electronic cassette 20C, which serves as the radiographic image capturing apparatus according to the third embodiment. The electronic cassette 20C has a grip 280 provided on a side surface of the panel unit 30.

More specifically, the grip 280 is disposed on the side surface 46b of the housing 40, which faces in the direction of the arrow X2. The grip 280 includes a handle that cooperates with the side surface 46b in defining a hole 282 therebetween, which is large enough for a hand of the doctor or radiological technician (user) to be placed therein.

Figure 58:
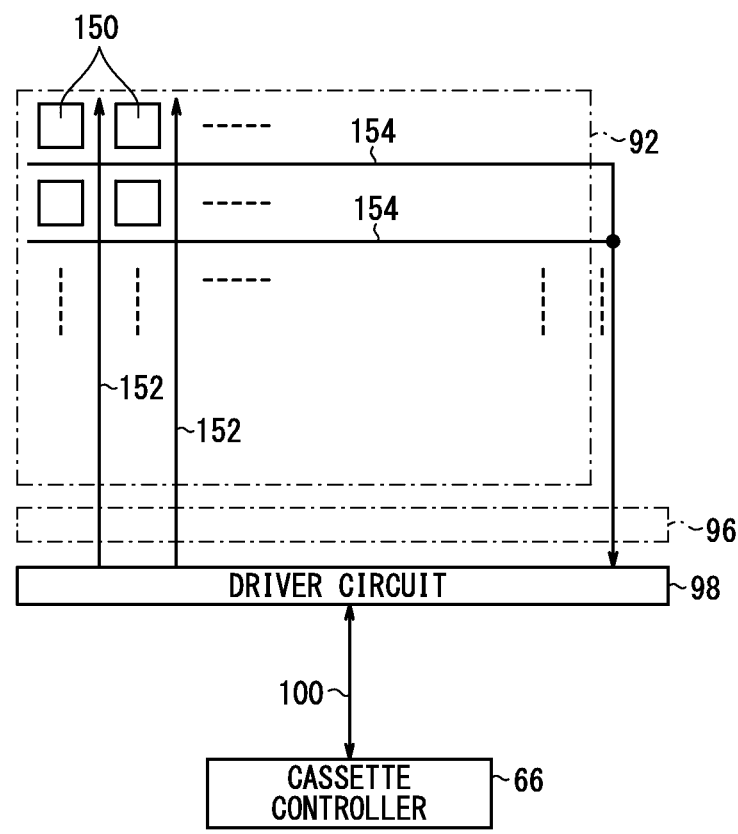
FIG. 58 is a diagram schematically showing an array of pixels in a radiation conversion panel, and electric connections between the pixels and a cassette controller.
Figure 59:
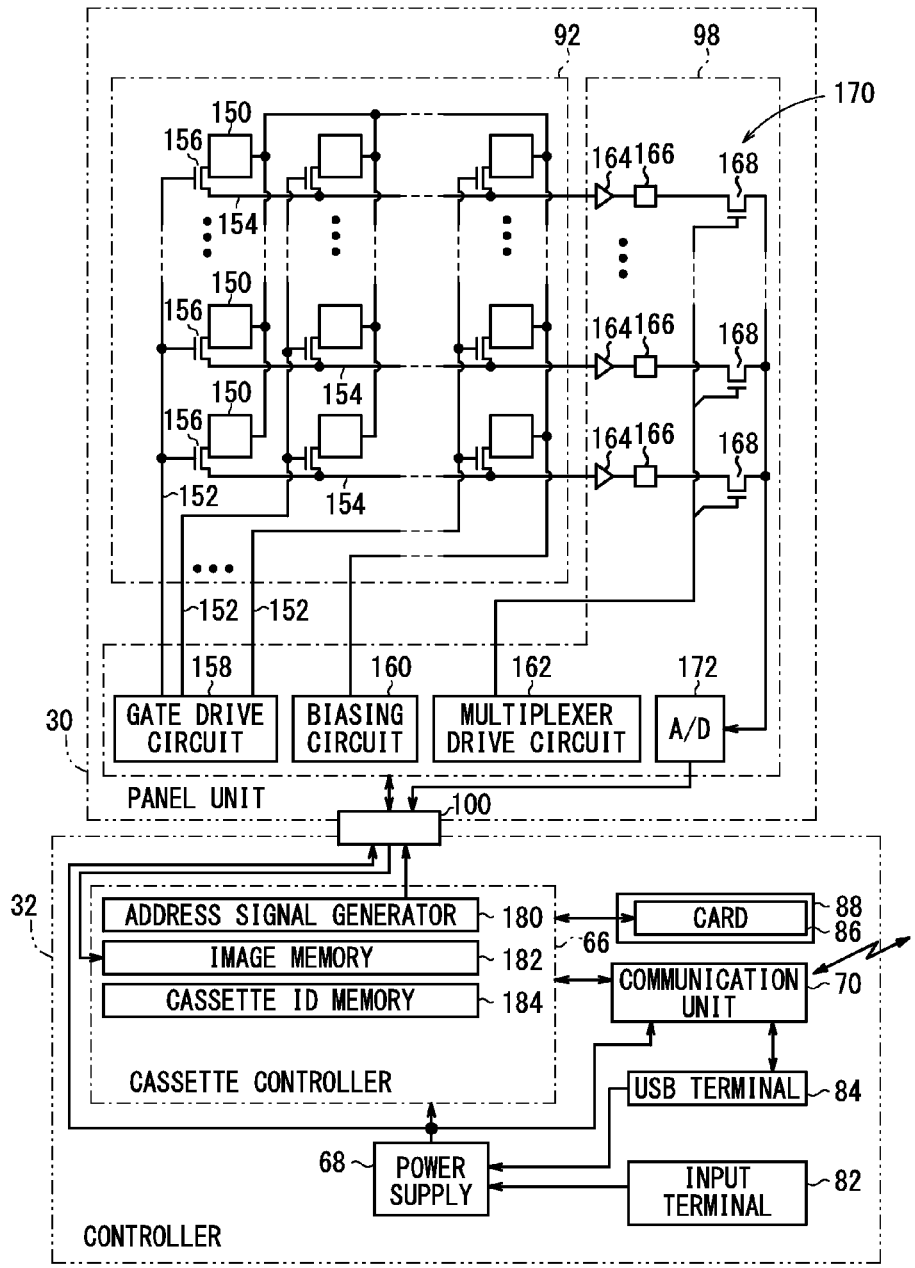
FIG. 59 is a block diagram of the cassette shown in FIG. 52.

In the panel unit 30, the driver circuit 98 is electrically connected to the cassette controller 66 through the flexible board 100, which extends through a hole 360 defined in the bottom surface of the housing 60 (see FIGS. 58 and 59). The power supply 68 supplies electric power through the flexible board 100 to the driver circuit 98, which drives the radiation conversion panel 92 through the flexible board 96.

Figure 57:
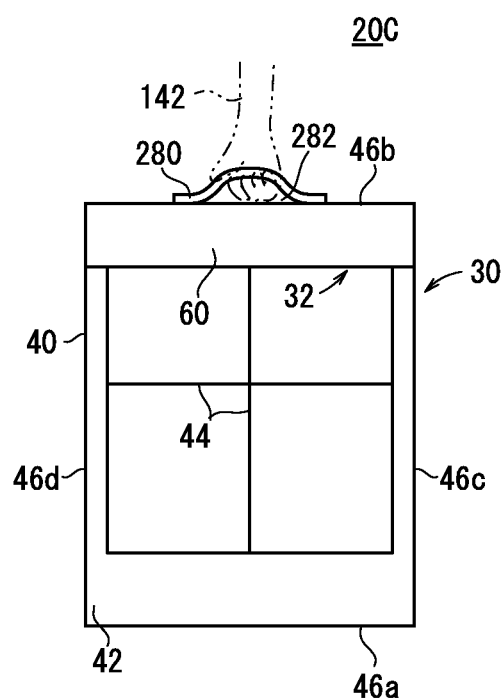
FIG. 57 is a plan view showing the manner in which the cassette shown in FIG. 52 is carried.

FIG. 57 shows the manner in which the user 142, such as a doctor or radiological technician, carries the electronic cassette 20C.

Since the controller 32 is disposed on the side surface 46b, as described above, the user 142 grips the grip 280 and carries the electronic cassette 20C with the controller 32 and the grip 280 in an uppermost position.

Among the components of the electronic cassette 20C, the power supply 68 (see FIGS. 53 and 56) is relatively heavy, so that the ratio of the weight of the controller 32 to the overall weight of the electronic cassette 20C is large. In the controller 32, the cassette controller 66, the power supply 68, and the communication unit 70 are located centrally in the housing 60. In FIG. 57, the electronic cassette 20C is in an eccentric state, in which the geometrically central position of the electronic cassette 20C (the central position of the image capturing area 36) and the center of gravity of the electronic cassette 20C (the position near the controller 32) do not coincide with each other, thereby making the entire electronic cassette 20C unbalanced in terms of the weight distribution thereof.

However, in FIG. 57, the electronic cassette 20C has the center of gravity thereof located in an upper portion, and the user 142 carries the electronic cassette 20C, which is heavy, through the grip 280. Therefore, the user 142 can carry the electronic cassette 20C in a stable manner.

<Description of Operations of the Third Embodiment>

The radiographic image capturing system 10C, which incorporates the electronic cassette 20C according to the third embodiment, is basically constructed as described above. Operations of the radiographic image capturing system 10C will be described below with reference to the flowchart shown in FIG. 12.

The radiographic image capturing system 10C operates in the same manner as the radiographic image capturing systems 10A and 10B, except that steps S2, S8 are dispensed with, and steps S1, S3, S9 are changed in the following manner.

Figure 52:
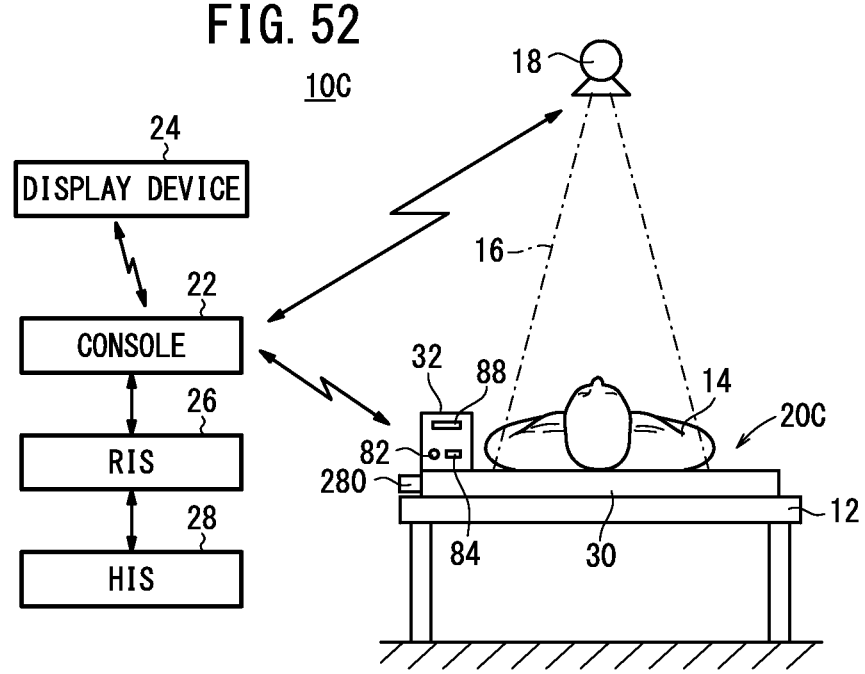
FIG. 52 is a schematic view of a radiographic image capturing system incorporating therein a cassette according to a third embodiment of the present invention.
Figure 53:
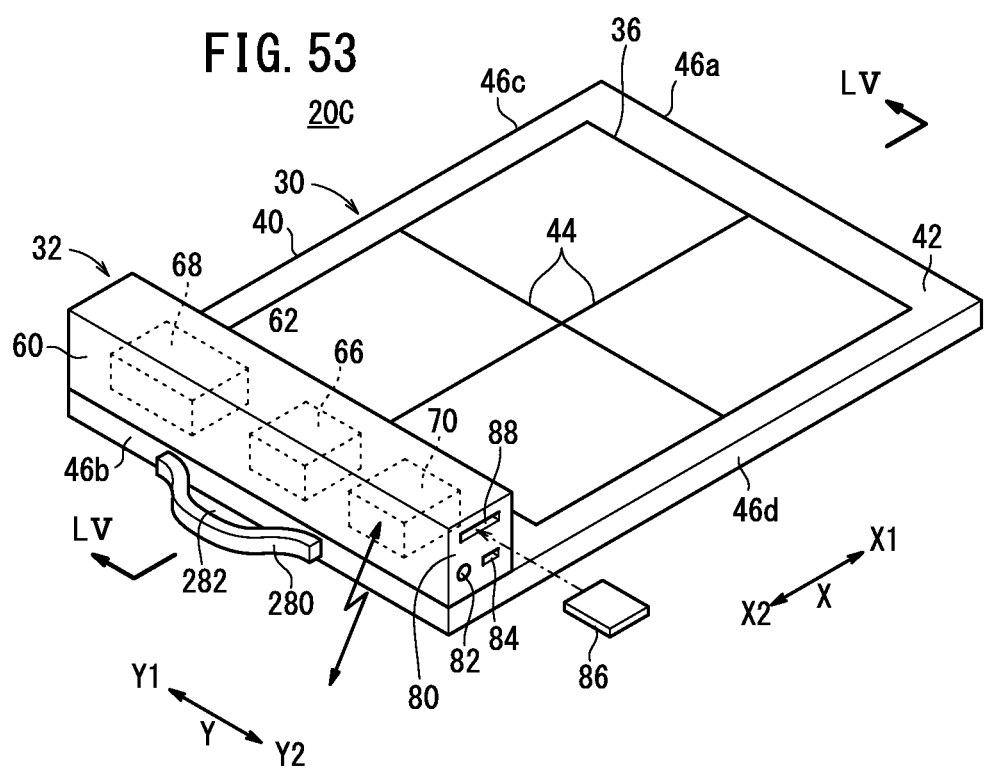
FIG. 53 is a perspective view of the cassette shown in FIG. 52.
Figure 54:
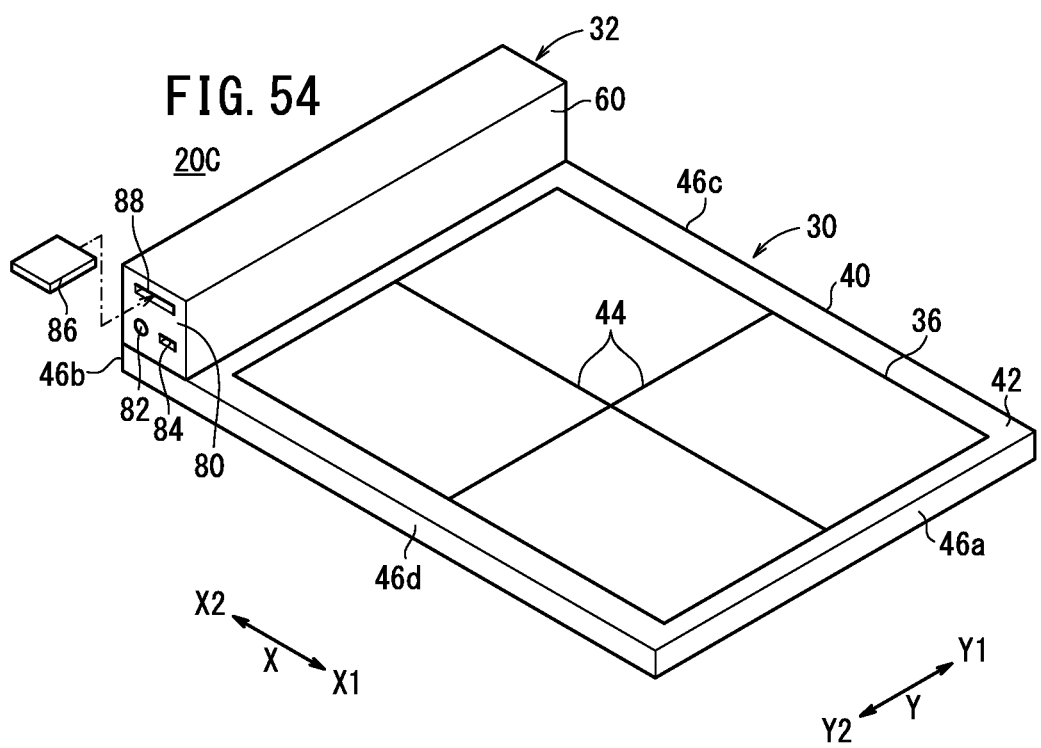
FIG. 54 is a perspective view of the cassette shown in FIG. 52.
Figure 55:
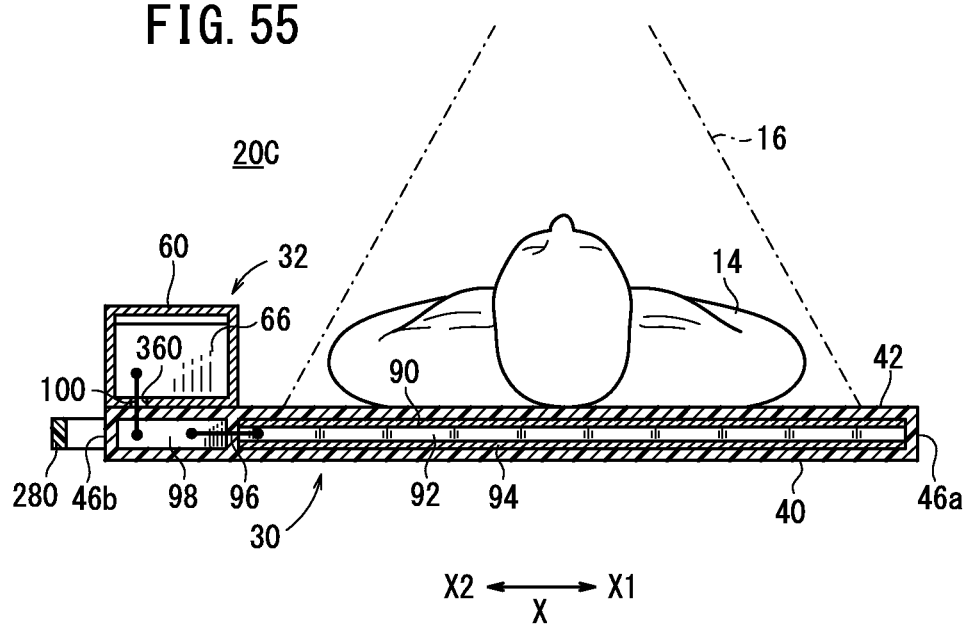
FIG. 55 is a cross-sectional view taken along line LV-LV of FIG. 53.
Figure 56:
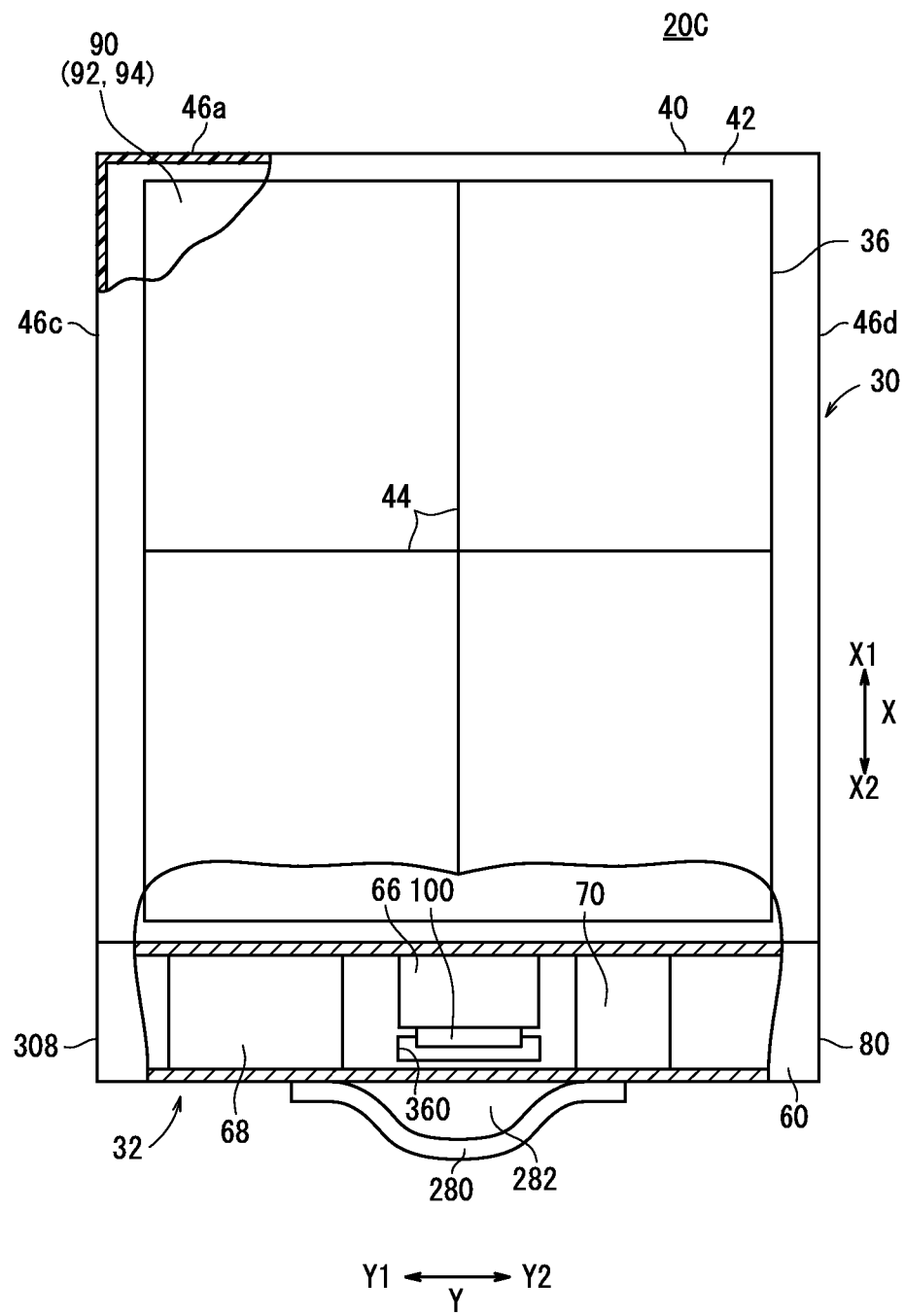
FIG. 56 is a plan view, partially cut away, of the cassette shown in FIG. 52.

In step S1 shown in FIG. 12, the user 142, who may be a doctor or radiological technician, grips the grip 280 with the grip 280 and the controller 32 in an uppermost position (see FIG. 57), and carries the electronic cassette 20C from a given storage location in the radiological department of the hospital to the image capturing base 12 (see FIG. 52). At this time, the power supply 68 (FIGS. 53, 56, and 59) supplies electric power only to the cassette controller 66, and the electronic cassette 20B is placed in a sleep mode with only the cassette controller 66 operating.

In step S3, after the user 142 has placed the electronic cassette 20C on the image capturing base 12 with the controller 32 and the irradiation surface 42 facing upwardly, the user 142 turns on a power supply switch (not shown) of the electronic cassette 20C. The cassette controller 66 controls the power supply 68 to supply electric power to the communication unit 70 and the panel unit 30, in addition to the cassette controller 66. At this time, the power supply 68 starts to supply electric power to the communication unit 70 and the panel unit 30, and the communication unit 70 becomes capable of sending signals to and receiving signals from the console 22 via a wireless communication link. If supplied with electric power from the power supply 68, the driver circuit 98 of the panel unit 30 is activated. The biasing circuit 160 supplies a bias voltage to the pixels 150 to enable the pixels 150 to store electric charges therein. As a result, the electronic cassette 20C changes from a sleep mode into an active mode.

In step S9, the user 142 turns off the power supply switch of the electronic cassette 20C, whereupon the cassette controller 66 controls the power supply 68 to supply electric power only to the cassette controller 66. The power supply 68 immediately stops supplying electric power to the communication unit 70 and the panel unit 30, and supplies electric power only to the cassette controller 66. As a result, the electronic cassette 20C changes from the active mode into a sleep mode in which only the cassette controller 66 is operable.

Then, the user 142 grips the grip 280 with the grip 280 and the controller 32 in an uppermost position, and user 142 carries the electronic cassette 20C to a given storage location in the radiological department of the hospital.

<Description of Advantages of the Third Embodiment>

As described above, the user 142 carries the electronic cassette 20C according to the third embodiment by gripping the grip 280 on the controller 32, which is heavy, and is responsible for the unbalanced weight distribution.

According to the third embodiment, more specifically, in the electronic cassette 20C, the weight distribution of which is shifted toward the controller 32, the grip 280 is disposed on the panel unit 30 in the vicinity of the controller 32 (on the side surface 46b). The user 142 carries the electronic cassette 20C by gripping the grip 280 with the controller 32 and the grip 280 disposed in an upper portion (uppermost position) of the electronic cassette 20C.

Since the user 142 grips the controller 32, which is heavy, through the grip 280, the electronic cassette 20C feels light if the user 142 carries the same. Therefore, the user 142 can carry the electronic cassette 20C stably and easily. Consequently, the user 142 can carry the electronic cassette 20C without dropping the electronic cassette 20C or causing the controller 32 to hit other objects. Therefore, the user 142 experiences a reduced burden upon carrying the electronic cassette 20C.

According to the third embodiment, since the grip 280 is disposed near the controller 32, the user 142 grips the heavy controller 32 through the grip 280, and hence the user 142 can carry the electronic cassette 20C in a stable manner.

With the grip 280, which is disposed on the side surface 46b of the housing 40 of the panel unit 30 in the vicinity of the controller 32, the grip 280 and the controller 32 are located in an uppermost position of the electronic cassette 20C at times that the user 142 carries the electronic cassette 20C. Therefore, the electronic cassette 20C can be carried with increased stability.

According to the third embodiment, similar to the first and second embodiments, it has been described that the housing 60 of the controller 32, which is thicker than the housing 40 of the panel unit 30, is disposed on the housing 40. However, the third embodiment is not limited to this description, and the controller 32 may be disposed so as to protrude from the housing 40.

According to the third embodiment, similar to the first and second embodiments, the controller 32 may be disposed in a location outside of an area of the panel unit 30 that is irradiated with radiation 16 having passed through the subject 14. In such a case, the console 22 trims a portion of the radiographic image acquired from the electronic cassette 20C, which corresponds to the area irradiated with radiation 16, thereby obtaining a desired image corresponding to the irradiated area.

<Description of Modifications of the Third Embodiment>

Figure 62:
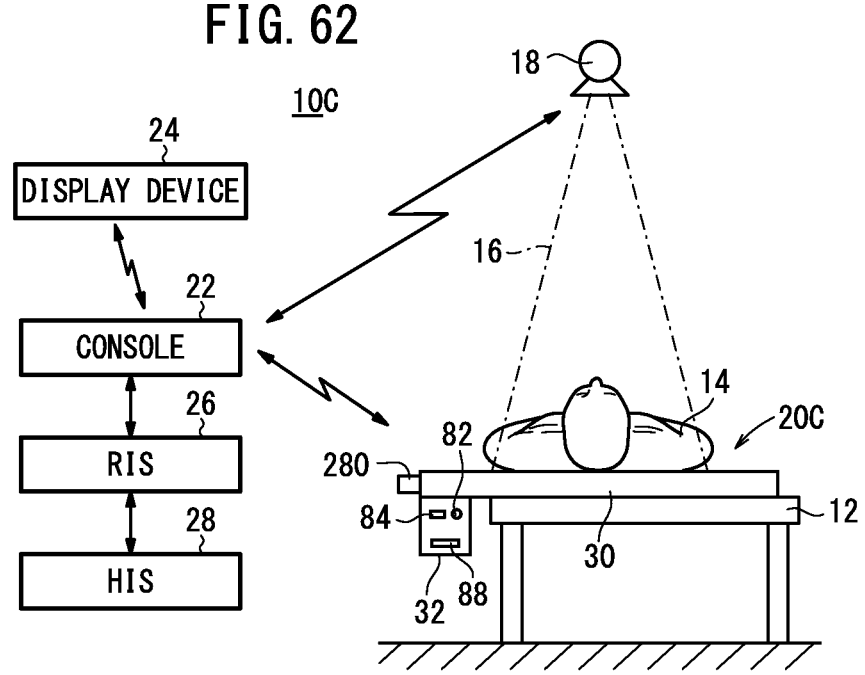
FIG. 62 is a schematic view of a radiographic image capturing system incorporating therein a double-sided image capturing cassette.
Figure 63:
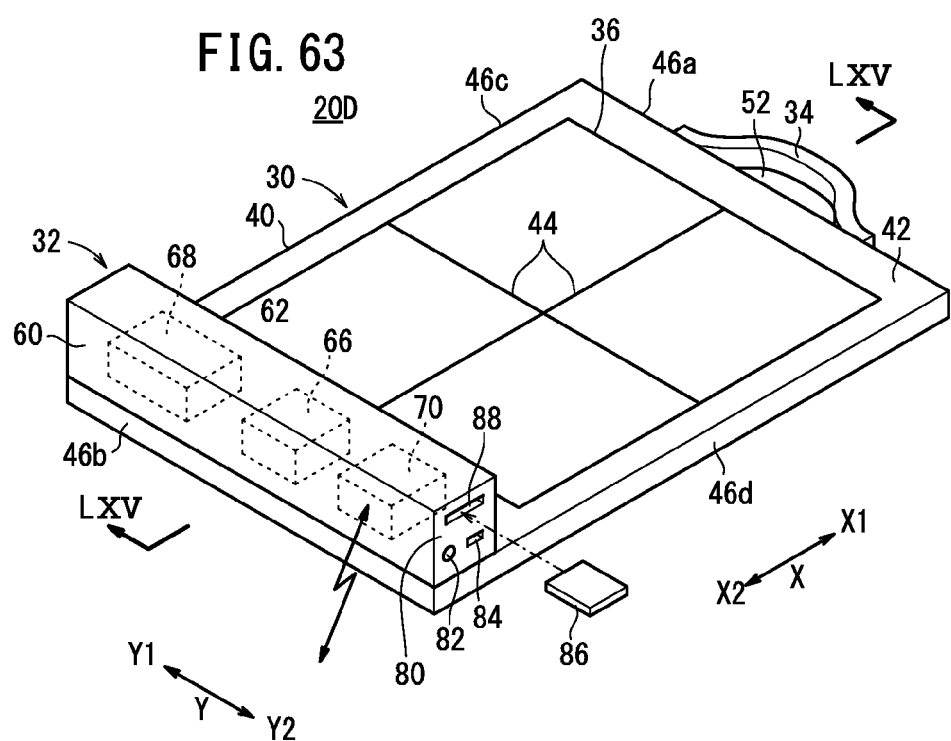
FIG. 63 is a perspective view of the cassette shown in FIG. 1.
Figure 64:
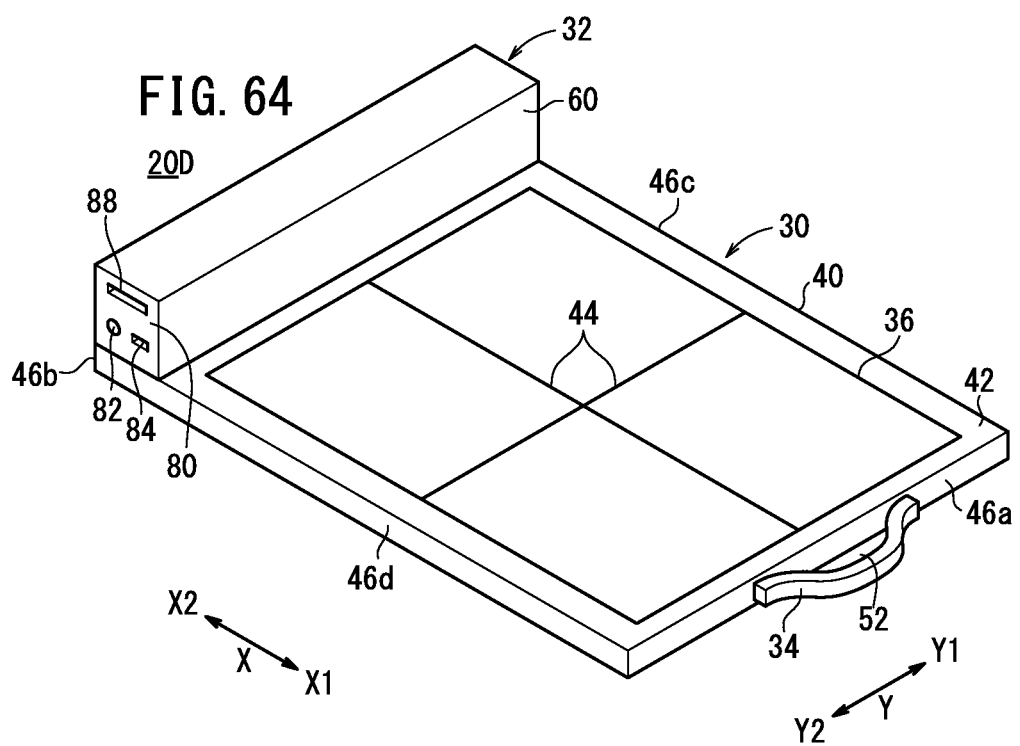
FIG. 64 is a perspective view of the cassette shown in FIG. 1.
Figure 65:
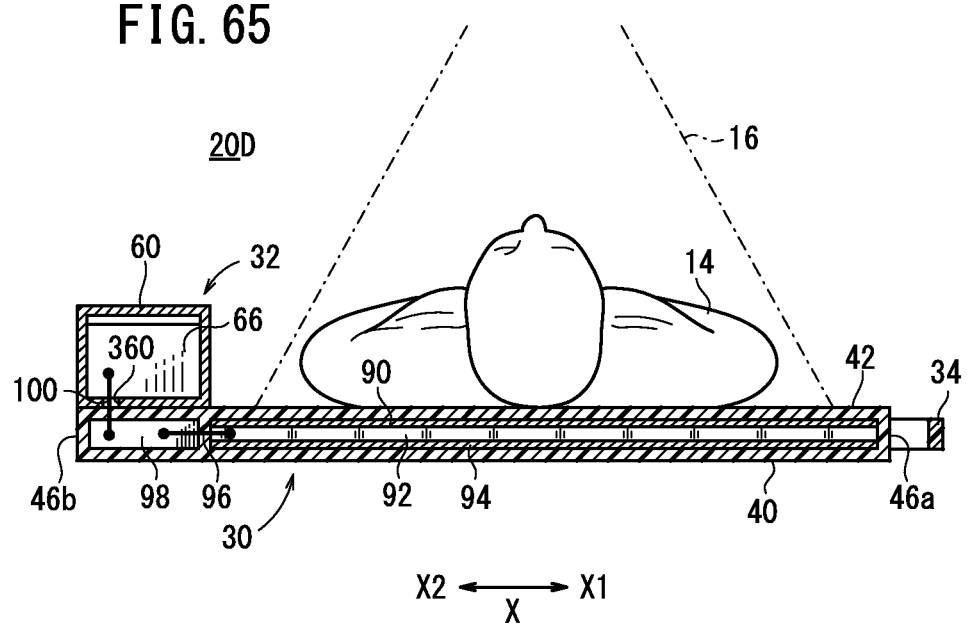
FIG. 65 is a cross-sectional view taken along line LXV-LXV of FIG. 63.
Figure 66:
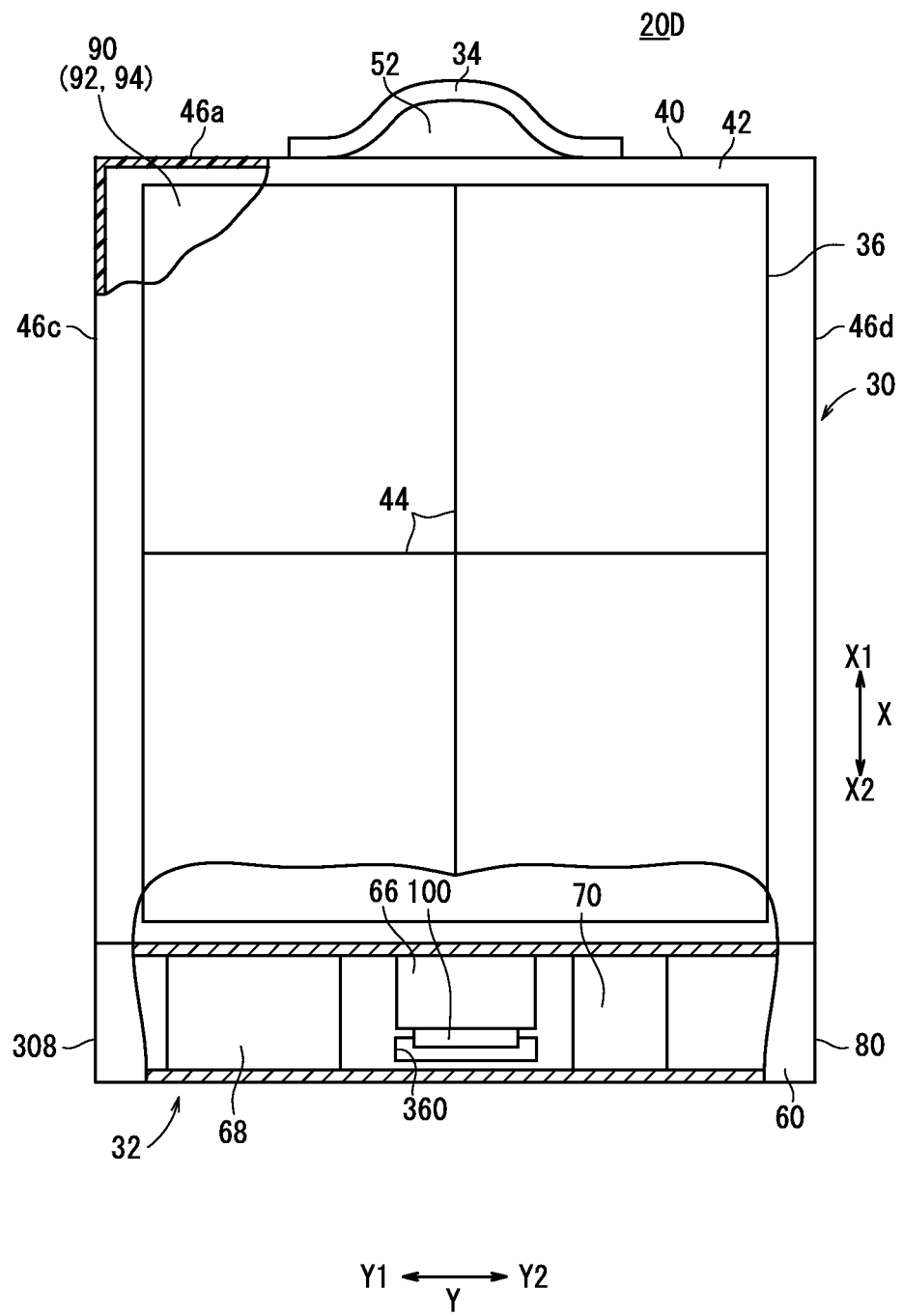
FIG. 66 is a plan view, partially cut away, of the cassette shown in FIG. 1.

The electronic cassette 20C according to the third embodiment is not limited to the above description, but may be implemented according to the embodiments shown in FIGS. 60 through 62.

FIG. 60 is a perspective view showing a process of charging the power supply 68 with the cradle 190. The electronic cassette 20C and the cradle 190 are electrically connected to each other through the USB cable 192 having the connectors 194, 196, thereby achieving the same advantages as those discussed in connection with FIGS. 13 and 38.

FIG. 61A shows a grip 370 disposed on a side surface of the housing 60 of the controller 32, which faces in the direction of the arrow X2. The grip 370 includes a handle that cooperates with the side surface of the housing 60 in defining a hole 372, which is large enough for a hand of the user 142 to be placed therein.

The user 142 may grip the grip 370 and carry the electronic cassette 20C while the grip 370 and the controller 32 are in an uppermost position. Since the user 142 directly grips the controller 32 through the grip 370, the user 142 can carry the electronic cassette 20A with increased stability.

The structure shown in FIG. 61B differs from the structure shown in FIG. 61A, in that a foldable grip 380 is disposed on a side surface of the housing 60.

The side surface of the housing 60 has a substantially hexagonal recess 382 defined therein, and opposite ends of the grip 380 are disposed in the recess 382. The recess 382 houses a rectangular support 384 therein, and opposite ends of a shaft 386, which extends through the support 384, are coupled to respective opposite ends of the grip 380.

If the user 142 does not grip the grip 380, the grip 380 is placed in the recess 382. If the user 142 intends to grip the grip 380, the user 142 turns the central portion of the grip 380 about the shaft 386, pulls the grip 380 out of the recess 382, and grips the grip 380. To place the grip 380 back into the recess 382, the user 142 turns the central portion of the grip 380 about the shaft 386 into the recess 382.

The structure shown in FIG. 61B provides the same advantages as those offered by the structure shown in FIG. 61A. In addition, since the user 142 can pull out the grip 380 only at times that the electronic cassette 20C is to be carried, the grip 380 does not present an obstacle to capturing of radiographic images. Therefore, the user 142 finds it easier to handle the electronic cassette 20C.

According to the third embodiment, as shown in FIG. 62, if a double-sided image capturing electronic cassette 20C is employed, then the subject 14 may be imaged after the electronic cassette 20C has been turned upside down and placed on the image capturing base 12. Such a modification offers the same advantages as those of the structures shown in FIGS. 24, 51 and according to the third embodiment.

According to the third embodiment, the controller 32 is disposed on the housing 40 of the panel unit 30 on the side surface 46b of the irradiation surface 42. The grip 280 also is disposed on the side surface 46b.

However, the third embodiment is not limited to such a description. The controller 32 may be disposed in any position insofar as the controller 32 is positioned on a side surface (side surface 46b) of the housing 40 and remains in contact with the housing 40.

For example, the controller 32 may be disposed on the housing 40 on the side surface of the irradiation surface 42 (face side), the side surface 46b of the housing 40, or the side surface of the bottom surface (reverse side) of the housing 40. The grip 280, 370, 380 may be disposed in the vicinity of the controller 32 on the side surface 46b of the housing 40 and/or on the controller 32.

At times that the user 142 carries the electronic cassette 20C, the grip 280, 370, 380 and the controller 32 are reliably positioned on the upper portion of the electronic cassette 20C. Therefore, the user 142 can carry the electronic cassette 20C with increased stability.

With the controller 32 disposed on the irradiation surface 42 of the housing 40, as shown in FIGS. 52 through 61B, the grip 280, 370, 380 and the controller 32 are positioned on an upper portion of the electronic cassette 20C at times that the user 142 carries the electronic cassette 20C. The electronic cassette 20C is placed on the image capturing base 12 with the irradiation surface 42 and the controller 32 facing upwardly during capturing of radiographic images. As a consequence, the electronic cassette 20C can be carried and placed with ease, and can be handled easily.

The third embodiment may be applied to the electronic cassette 20A according to the first embodiment. In this case, if the user 142 grips the grip 34 and carries the electronic cassette 20A with the grip 34 and the controller 32 in an uppermost position, then the electronic cassette 20A can offer the same advantages as those of the third embodiment.

The third embodiment may also be applied to the electronic cassette 20B according to the second embodiment. In this case, if the user 142 grips the grip 34 and carries the electronic cassette 20B with the grip 34 in an uppermost position, and the side surface 80 of the controller 32 being located above the substantially central portion of the image capturing area 36, then the electronic cassette 20B can offer the same advantages as those of the third embodiment.

The third invention is not limited to the above embodiment, but various alternative arrangements may be adopted without departing from the scope of the third invention.

For example, if a scintillator 608 made of CsI is used in the third embodiment, then, similar to the case of the first and second embodiments, the grips 370, 380 may be made of a material having a high coefficient of thermal conductivity, whereby the grips 370, 380 are used as a heat radiating member for radiating heat generated by the controller 32, so as to prevent heat generated by the controller 32 from being transmitted to the radiation conversion panel 92 in the panel unit 30. A wavy or rectangular member, which functions as a heat sink, may be mounted on the grips 370, 380 for increasing the heat radiating area thereof. Since the grips 370, 380 are mounted directly on the housing 60 of the controller 32, the grips 370, 380 can directly radiate heat generated by the controller 32. Furthermore, inasmuch as the grips 370, 380 are gripped by the user 142, the grips 370, 380 must be capable of radiating heat in a manner so as not to cause the user 142 to suffer a low temperature burn.

If the controller 32 is disposed in the vicinity of the grip 280, the grip 280, which is mounted on the panel unit 30, may be made of a material having a high coefficient of thermal conductivity and used as a heat radiating member. A wavy or rectangular member may be mounted on the grip 280, which is constructed in this manner, for thereby increasing the heat radiating area thereof. The grip 280 must radiate heat in a manner so as not to cause the user 142 to suffer a low temperature burn.

Since the housing 60 of the controller 32 houses therein components that generate a large amount of heat, such as the power supply 68, etc., such components, which generate a large amount of heat, may be positioned in the housing 60 near the grips 370, 380, for thereby efficiently radiating heat generated by the controller 32 through the grips 370, 380.

4. Descriptions of Fourth and Fifth Embodiments:

Radiographic image capturing apparatus according to preferred embodiments (fourth and fifth embodiments) of the fourth invention will be described in detail below with reference to FIGS. 63 through 69B.

First, an electronic cassette 20D, which serves as a radiographic image capturing apparatus according to the fourth embodiment, will be described below with reference to FIGS. 63 through 68B.

<Description of Arrangement of the Fourth Embodiment>

In a radiographic image capturing system 10D, which incorporates the electronic cassette 20D according to the fourth embodiment, the grip 34 is disposed on a side surface of the panel unit 30 of the electronic cassette 20D. More specifically, the grip 34 is disposed on a side surface 46a of the housing 40, which faces in the direction of the arrow X1.

For carrying the electronic cassette 20D, since as shown in FIG. 37B, the controller 32 is disposed on the side surface 46b, the user 142 grips the grip 34 with the controller 32 being in a lowermost position and the grip 34 in an uppermost position, whereupon the user 142 carries the electronic cassette 20D.

Among the components of the electronic cassette 20D, the power supply 68 (see FIGS. 63 and 66) is relatively heavy, so that the ratio of the weight of the controller 32 to the overall weight of the electronic cassette 20D is large. In the controller 32, the cassette controller 66, the power supply 68, and the communication unit 70 are centrally located in the housing 60. In FIG. 37B, the electronic cassette 20D is in an eccentric state, in which the geometrically central position of the electronic cassette 20D (the central position of the image capturing area 36) and the center of gravity of the electronic cassette 20D (the position near the controller 32) do not coincide with each other, thereby making the entire electronic cassette 20D unbalanced in terms of weight distribution.

However, in FIG. 37B, the electronic cassette 20D has the center of gravity thereof located in a lowermost position, and the user 142 carries the electronic cassette 20D having a low center of gravity. Therefore, despite the unbalanced weight distribution, the user 142 can carry the electronic cassette 20D in a stable manner.

<Description of Operations of the Fourth Embodiment>

The radiographic image capturing system 10D, which incorporates the electronic cassette 20D according to the fourth embodiment, is basically constructed as described above. Operations of the radiographic image capturing system 10D will be described below with reference to the flowchart shown in FIG. 12.

The radiographic image capturing system 10D operates in the same manner as the radiographic image capturing system 10C, except for steps S1 and S9, which are changed in the following manner.

In step S1, the user 142, who may be a doctor or radiological technician, grips the grip 34 with the grip 34 being in an uppermost position and the controller 32 in a lowermost position (see FIG. 37B). The user 142 carries the electronic cassette 20D from a given storage location in the radiological department of the hospital to the image capturing base 12 (see FIG. 1). At this time, the power supply 68 (see FIGS. 63 and 66) supplies electric power only to the cassette controller 66, while the electronic cassette 20D remains in a sleep mode with only the cassette controller 66 operating.

In step S9, the user 142 turns off the power supply switch of the electronic cassette 20D. The cassette controller 66 controls the power supply 68 to supply electric power only to the cassette controller 66. The power supply 68 immediately stops supplying electric power to the communication unit 70 and the panel unit 30, and supplies electric power only to the cassette controller 66. As a result, the electronic cassette 20D changes from an active mode to a sleep mode, in which only the cassette controller 66 is operable.

Then, the user 142 grips the grip 34 with the grip 34 in an uppermost position and the controller 32 in a lowermost position, and carries the electronic cassette 20D to a given storage location in the radiological department of the hospital.

<Description of Advantages of the Fourth Embodiment>

As described above, the user 142 carries the electronic cassette 20D according to the fourth embodiment by gripping the grip 34, which is disposed in an uppermost position opposite to the controller 32 in the lowermost position, which is heavy and is responsible for the unbalanced weight distribution.

According to the fourth embodiment, more specifically, in the electronic cassette 20C, the weight distribution of which is shifted toward the controller 32, the grip 34 is disposed in a position opposite to the controller 32, and the user 142 carries the electronic cassette 20D by gripping the grip 34 with the grip 34 in an uppermost position (upper portion), and the controller 32, which is heavy and responsible for the unbalanced weight distribution, in a lowermost position (lower portion).

Since the user 142 grips the grip 34 with the entire electronic cassette 20D having a low center of gravity, the electronic cassette 20D feels light upon being carried by the user 142. Therefore, the user 142 can carry the electronic cassette 20D easily and in a stable manner. Consequently, the user 142 can carry the electronic cassette 20D without dropping the electronic cassette 20D or causing the controller 32 to hit other objects. Thus, the user experiences a reduced burden upon carrying the electronic cassette 20D.

The controller 32 includes the cassette controller 66 having electronic components for controlling the radiation conversion panel 92, the power supply 68 such as a battery or the like, and the communication unit 70 for performing communications with external circuits. The temperature of the controller 32 tends to be increased due to heat generated by the cassette controller 66, the power supply 68, and the communication unit 70. According to the fourth embodiment, since the controller 32 and the grip 34 are disposed opposite to each other, heat from the controller 32 is reliably prevented from being transmitted to the grip 34. Therefore, the user 142 can grip the grip 34 and carry the electronic cassette 20D without having to worry about heat.

According to the fourth embodiment, as described above, inasmuch as the grip 34 and the controller 32 are disposed opposite to each other on the panel unit 30, the user 142 can grip the grip 34 with the entire electronic cassette 20D having a low center of gravity. Therefore, the user 142 can carry the electronic cassette 20D in a stable manner.

The controller 32 is disposed on the side surface 46b of the housing 40 of the panel unit 30 (one side of the irradiation surface 42 of the housing 40), and the grip 34 is disposed on the side surface 46a of the housing 40 (the other side of the irradiation surface 42). At times that the electronic cassette 20D is carried, the grip 34 is disposed in an uppermost position of the electronic cassette 20D, whereas the controller 32 is disposed in a lowermost position of the electronic cassette 20D. Therefore, the user 142 can carry the electronic cassette 20D with increased stability.

According to the fourth embodiment, similar to the first through third embodiments, it has been described that the housing 60 of the controller 32, which is thicker than the housing 40 of the panel unit 30, is disposed on the housing 40. However, the fourth embodiment is not limited to such a description, and the controller 32 may be disposed so as to protrude from the housing 40.

According to the fourth embodiment, similar to the first through third embodiments, the controller 32 may be disposed in a location outside of an area of the panel unit 30 that is irradiated with radiation 16 having passed through the subject 14. In such a case, the console 22 trims a portion of the radiographic image acquired from the electronic cassette 20D, which corresponds to the area irradiated with radiation 16, thereby obtaining a desired image corresponding to the irradiated area.

<Description of Modifications of the Fourth Embodiment>

Figure 68A:
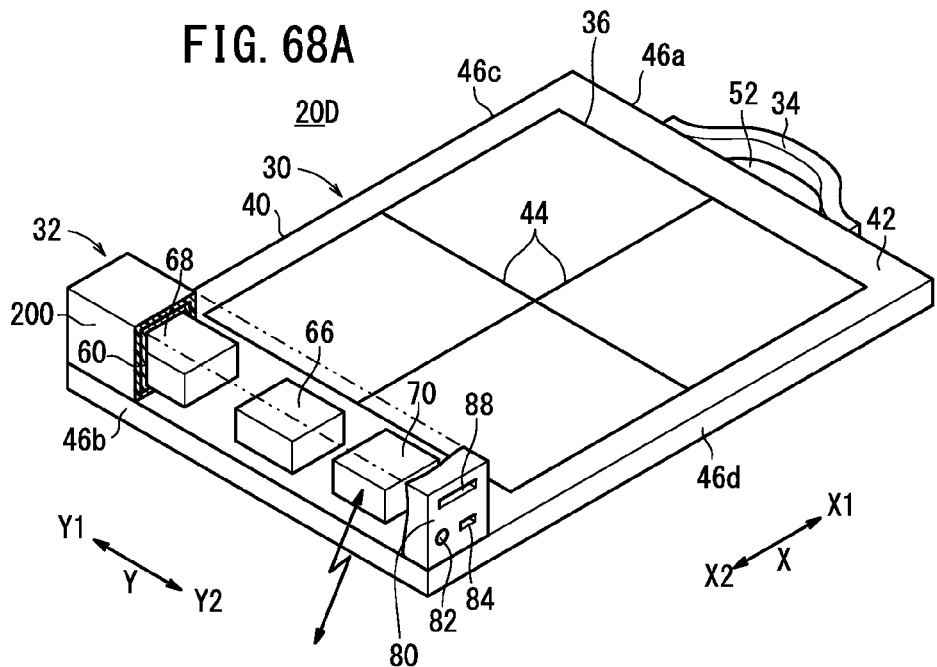
FIGS. 68A and 68B are perspective views of cassettes, which include respective cushioning members provided on controllers.
Figure 68B:
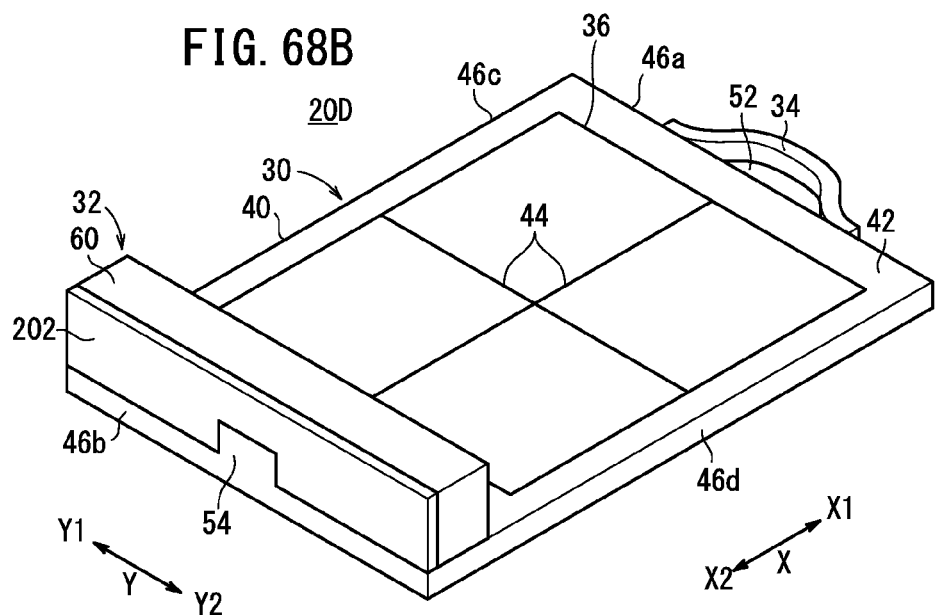

The electronic cassette 20D according to the fourth embodiment is not limited to the above description, but may be implemented according to the embodiments shown in FIGS. 67 through 68B.

FIG. 67 is a perspective view showing a process of charging the power supply 68 with the cradle 190. The electronic cassette 20C and the cradle 190 are electrically connected to each other by a USB cable 192 having connectors 194, 196, thus achieving the same advantages as those of the embodiments shown in FIGS. 13, 38, and 60.

FIG. 68A shows the housing 60 of the controller 32, which is entirely covered with the cushioning member 200. FIG. 68B shows the housing 60, the side surface 46b of which is covered with the cushioning member 202.

In the case that the user 142 carries the electronic cassette 20D, the controller 32 is disposed in a lowermost position on the electronic cassette 20D, as shown in FIG. 37B. The housing 60 of the controller 32 is covered entirely with the cushioning member 200, or is covered partially with the cushioning member 202, so that the controller 32 is effectively protected from impacts if the electronic cassette 20D is dropped or if the controller 32 hits other objects.

According to the fourth embodiment, the irradiation surface 42 is irradiated with radiation 16. However, as shown in FIG. 24, if a double-sided image capturing electronic cassette 20D is employed, then the subject 14 may be imaged after the electronic cassette 20D has been turned upside down and placed on the image capturing base 12. Such a modification offers the same advantages as those of the structures shown in FIG. 24 according to the fourth embodiment.

According to the fourth embodiment, the controller 32 is disposed on the housing 40 of the panel unit 30 at a side surface 46b of the irradiation surface 42, and the grip 34 is disposed on the side surface 46a opposite to the side surface 46b.

However, the fourth embodiment is not limited to such a description. Alternatively, the controller 32 may be disposed in any position insofar as the controller 32 is positioned on an end surface (side surface 46b) of the housing 40. The grip 34 may be disposed in any position insofar as the grip 34 is positioned on the other end surface (side surface 46a) of the housing 40.

For example, the controller 32 may be disposed on the housing 40 at any of the end surface of the irradiation surface 42 (face side), the end surface of the side surfaces 46b through 46d of the housing 40, or the end surface of the bottom surface (reverse side) of the housing 40. The grip 34 may be disposed on the housing 40 at any of the other surface of the irradiation surface 42, the other end surface of the side surfaces 46a, 46c, 46d of the housing 40, or the other end surface of the bottom surface of the housing 40.

With the controller 32 and the grip 34 being provided in the above positions on the housing 40, upon the user 142 carrying the electronic cassette 20D, the grip 34 is reliably positioned on the upper portion of the electronic cassette 20D, and the controller 32 is reliably positioned on the lower portion of the electronic cassette 20D. Therefore, the user 142 can carry the electronic cassette 20D with increased stability.

The fourth embodiment may be applied to the electronic cassettes 20A, 20B according to the first and second embodiments. In this case, if the user 142 grips the grip 34 and carries the electronic cassettes 20A, 20B with the side surface 80 of the controller 32 located in a lowermost position of the electronic cassettes 20A, 20B, or substantially centrally in the image capturing area 36 positioned below the grip 34, then the electronic cassettes 20A, 20B offer the same advantages as those of the fourth embodiment.

<Description of Fifth Embodiment>

An electronic cassette 20E according to a fifth embodiment will be described below with reference to FIGS. 69A and 69B.

The electronic cassette 20E according to the fifth embodiment is incorporated in a radiographic image capturing system 10E. The electronic cassette 20E according to the fifth embodiment differs from the fourth embodiment, in that the housing 60 is turned by a moving mechanism 188 (see FIGS. 46A and 46B) of the electronic cassette 20B, similar to the case of the second embodiment.

The moving mechanism 188 includes the shaft 348, which is mounted vertically on the irradiation surface 42 near the side surface 308 of the housing 60, the hole 350, which is defined in the bottom surface of the housing 60 near the side surface 308 with the shaft 348 extending through the hole 350, the protrusion 352, which extends through the hole 350 and extends in the radial direction of the shaft 348 from the distal end of the shaft 348 that is inserted in the housing 60, and the substantially arcuate rotation limiting member 354, which is partially open and substantially surrounds the hole 350 as viewed in plan.

The moving mechanism 188 only turns the housing 60 about the shaft 348, but does not move the housing 60 along the directions of the arrow X.

Figure 69A:
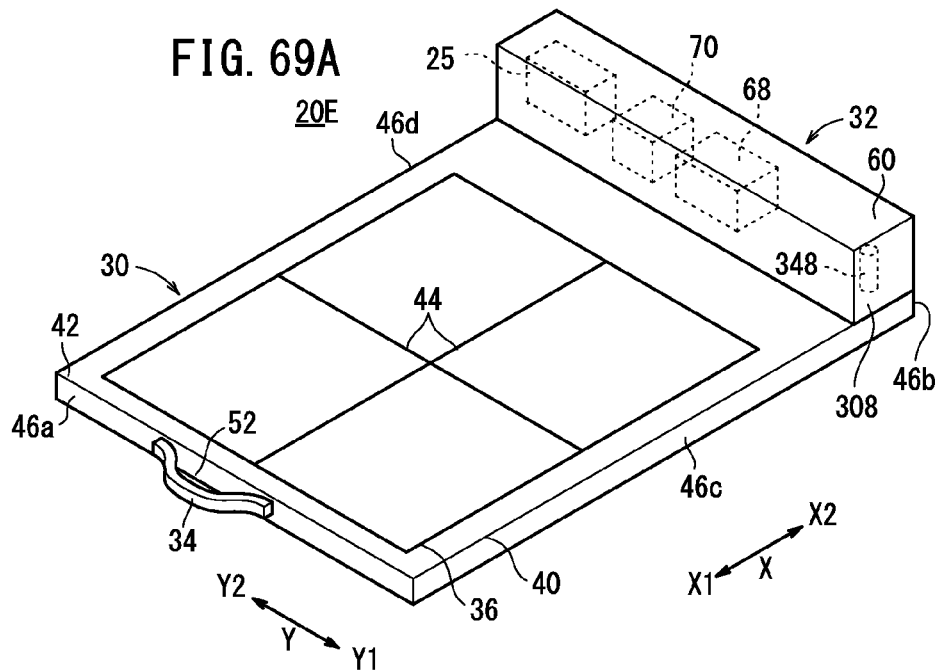
Figure 69B:
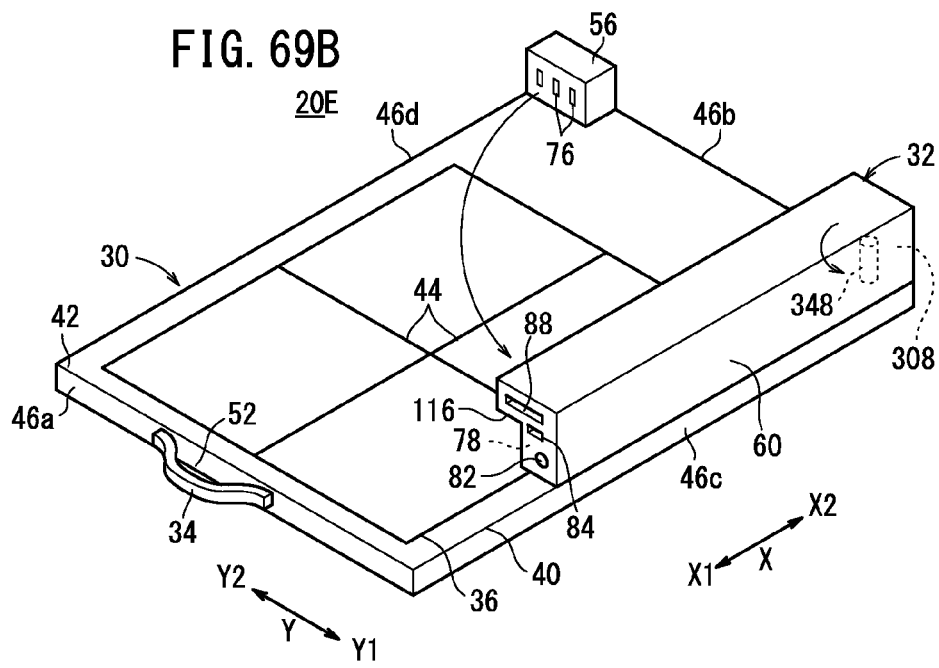

For turning the housing 60 from the position on the side surface 46b, as shown in FIG. 69A, to the position on the side surface 46c, as shown in FIG. 69B, the user 142 turns the housing 60 counterclockwise about the shaft 348 by 90°, as shown in FIGS. 46A and 46B. The end 356 of the rotating limiting member 354 is spaced away from the protrusion 352, whereas the other end 358 of the rotating limiting member 354 abuts against the protrusion 352, thereby positioning the housing 60 on the side surface 46c. At this time, the connection terminal 76 and the connection terminal 78 are taken out of contact and hence are electrically disconnected from each other.

Since the controller 32 is turned about the shaft 348 as shown in FIGS. 69A and 69B, it is possible to bring the center of gravity close to the geometrically central position of the electronic cassette 20E, thereby minimizing the unbalanced weight distribution, even if the user 142 carries the electronic cassette 20E with the grip 34 in an uppermost position. Inasmuch as the controller 32 remains disposed below the grip 34, the user 142 can carry the electronic cassette 20E in a stable manner.

The shaft 348 is disposed at a location on the irradiation surface 42 outside of the image capturing area 36 (a location near the side surface 308). The hole 350 through which the shaft 348 extends is defined in a bottom surface of the housing 60 near the irradiation surface 42. Therefore, the controller 32 can be turned more stably and reliably.

The one end 356 and the other end 358, which define therebetween the opening of the rotation limiting member 354, and the protrusion 352 define an angular range within which the controller 32 can be turned about the shaft 348. The controller 32 can be turned accurately and with high precision with respect to the panel unit 30.

The fourth invention is not limited to the above embodiment, but various arrangements may be adopted without departing from the scope of the fourth invention.

The invention claimed is:

1. A radiographic image capturing apparatus comprising:
a panel unit housing therein a radiation conversion panel for converting radiation into a radiographic image; and
a controller disposed on the panel unit, including:
a panel controller configured to drive control the radiation conversion panel and read the radiographic image from the radiation conversion panel; and
a power supply configured to supply electric power to the panel controller and the radiation conversion panel,
wherein
the panel unit includes a substantially rectangular first housing permeable to the radiation, the radiation conversion panel being housed in the first housing,
one side surface of the first housing is an irradiation surface that is irradiated with the radiation,
the controller is housed in a substantially rectangular second housing which is thicker than the first housing or protrudes from the first housing, and
the second housing is slidable on the irradiation surface.

2. The radiographic image capturing apparatus according to claim 1, wherein the second housing is disposed in a location outside of an area of the irradiation surface that is irradiated with radiation having passed through a subject at least during an image capturing process.

3. The radiographic image capturing apparatus according to claim 1, wherein the second housing is disposed in a location outside of an image capturing area of the irradiation surface, which is capable of being irradiated with radiation at least during an image capturing process.

4. The radiographic image capturing apparatus according to claim 3, further comprising a moving mechanism for translating the second housing along the irradiation surface with respect to the first housing.

5. The radiographic image capturing apparatus according to claim 4, wherein the moving mechanism includes a substantially straight guide disposed on the irradiation surface other than the image capturing area, and a moving member, which is capable of being translated in unison with the second housing along the guide.

6. The radiographic image capturing apparatus according to claim 3, further comprising a moving mechanism for turning the second housing along the irradiation surface with respect to the first housing.

7. The radiographic image capturing apparatus according to claim 6, wherein the moving mechanism includes a shaft disposed on the irradiation surface other than the image capturing area for turning the second housing about the shaft.

8. The radiographic image capturing apparatus according to claim 3, wherein the controller further comprises communication unit configured to communicate with an external circuit, and the power supply supplies electric power to the communication unit.

9. The radiographic image capturing apparatus according to claim 8, wherein the power supply stops supplying electric power to the communication unit and the radiation conversion panel if the second housing slides.

10. The radiographic image capturing apparatus according to claim 9, wherein the panel unit includes a connector configured to electrically connect the radiation conversion panel and the controller to each other; and the power supply stops supplying electric power to the communication unit and the radiation conversion panel if the connector and the controller are spaced away from each other and are electrically disconnected from each other during sliding of the second housing.

11. The radiographic image capturing apparatus according to claim 10, wherein the panel controller includes a connection detector configured to detect whether or not the connector and the controller are electrically connected to each other.

12. The radiographic image capturing apparatus according to claim 3, wherein the first housing and/or the second housing has a grip that is gripped by a user.

13. The radiographic image capturing apparatus according to claim 12, wherein the second housing is disposed in a location outside of the image capturing area on the irradiation surface at least during the image capturing process; and the grip is disposed on a side surface of the first housing, an upper surface of the second housing, and/or a side surface of the second housing.

14. The radiographic image capturing apparatus according to claim 13, wherein if the second housing is disposed on the irradiation surface near a side surface thereof at least during the image capturing process, the grip is disposed on a side surface of the first housing, another side surface of the first housing, another surface thereof interconnecting the side surface and the other side surface, the upper surface of the second housing, and/or the side surface of the second housing.

15. The radiographic image capturing apparatus according to claim 1, wherein the radiation conversion panel comprises a scintillator configured to convert the radiation into visible light, solid-state detectors configured to convert the visible light into an electric signal representing the radiographic image, switching elements configured to read electric signals from the solid-state detectors, and a substrate on which the solid-state detectors and the switching elements are disposed; and the substrate comprises a flexible plastic substrate, the solid-state detectors are made of an organic photoconductor, and the switching elements are made of an organic semiconductor material.

16. The radiographic image capturing apparatus according to claim 15, wherein the substrate, the switching elements, the solid-state detectors, and the scintillator, which is made of CsI, are arranged in this order along a direction in which the radiation is applied.

\* \* \* \* \*